United States Patent
Chorev et al.

(10) Patent No.: US 9,417,248 B2
(45) Date of Patent: Aug. 16, 2016

(54) SURROGATES OF POST-TRANSLATIONALLY MODIFIED PROTEINS AND USES THEREOF

(75) Inventors: Michael Chorev, Chestnut Hill, MA (US); Jose A. Halperin, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 302 days.

(21) Appl. No.: 13/984,423

(22) PCT Filed: Feb. 10, 2012

(86) PCT No.: PCT/US2012/024645
§ 371 (c)(1),
(2), (4) Date: Oct. 1, 2013

(87) PCT Pub. No.: WO2012/109538
PCT Pub. Date: Aug. 16, 2012

(65) Prior Publication Data
US 2014/0024056 A1    Jan. 23, 2014

Related U.S. Application Data

(60) Provisional application No. 61/441,575, filed on Feb. 10, 2011.

(51) Int. Cl.
| | | |
|---|---|---|
| *G01N 33/68* | (2006.01) | |
| *C07K 16/28* | (2006.01) | |
| *C07K 14/705* | (2006.01) | |
| *C07K 16/44* | (2006.01) | |
| *G01N 33/564* | (2006.01) | |

(52) U.S. Cl.
CPC ...... *G01N 33/6872* (2013.01); *C07K 14/70596* (2013.01); *C07K 16/2896* (2013.01); *C07K 16/44* (2013.01); *G01N 33/564* (2013.01); *G01N 33/6893* (2013.01); *G01N 2440/00* (2013.01); *G01N 2800/042* (2013.01)

(58) Field of Classification Search
None
See application file for complete search history.

(56) References Cited

U.S. PATENT DOCUMENTS

| | | | |
|---|---|---|---|
| 9,068,006 B2 * | 6/2015 | Halperin | C07K 14/70596 |
| 2005/0032128 A1 * | 2/2005 | Halperin | G01N 33/66 435/7.2 |
| 2006/0246524 A1 | 11/2006 | Bauer et al. | |
| 2008/0081038 A1 | 4/2008 | Cho et al. | |
| 2008/0267980 A1 * | 10/2008 | Tomlinson | C07K 14/705 424/178.1 |
| 2009/0023157 A1 | 1/2009 | Lee et al. | |
| 2009/0028884 A1 | 1/2009 | Schwabe | |
| 2009/0162875 A1 * | 6/2009 | Dattwyler | G01N 33/569 435/7.32 |
| 2010/0331200 A1 | 12/2010 | Gordon et al. | |

FOREIGN PATENT DOCUMENTS

| | | |
|---|---|---|
| WO | WO-2004/045520 A2 | 6/2004 |
| WO | WO-2005/037989 A2 | 4/2005 |
| WO | WO-2008-137165 A1 | 11/2008 |

OTHER PUBLICATIONS

The European Search Opinion issued for a European counterpart EP EP2673293 A1, Application No. 12744613.6, on Dec. 3, 2014.*
A print-out retrieved from http://www.quantabiodesign.com/products/dpeg-based-crosslinking-reagents/heterobifunctional-reagents-amine-and-thiol-reactive/mal-dpegx-nhs-ester/ on Dec. 1, 2015.*
Acosta et al. "Molecular basis for a link between complement and the vascular complications of diabetes" Proc Natl Acad Sci U S A. 97(10):5450-5 (2000).
Extended European Search Report for European Patent Application No. 12744613.6, mailed Dec. 3, 2014 (9 pages).
International Preliminary Report on Patentability and Written Opinion for International Application No. PCT/US2012/024645, mailed Aug. 13, 2013 (8 pages).
International Search Report for International Application No. PCT/US2012/024645, mailed Sep. 19, 2012 (5 pages).

* cited by examiner

*Primary Examiner* — Galina Yakovleva
(74) *Attorney, Agent, or Firm* — Clark & Elbing LLP

(57) ABSTRACT

The present invention provides compounds that are surrogates of post-translationally modified proteins and uses thereof. Numerous diseases are associated with post-translationally modified proteins that are difficult to obtain in homogenous form and in quantities needed for immunization and use as convenient standards, calibrators, and/or reference compounds that facilitate the detection and analysis of endogenous post-translationally modified proteins. The surrogate compounds of the invention typically comprise antigenic epitopes (one of which carries a post-translational modification) that are tethered by a flexible and hydrophilic linker. The resulting compound behaves like a surrogate of the post-translationally modified protein because it preserves the character of the included antigens and allows recognition by specific antibodies targeting the individual antigens. The surrogate compounds may be prepared by covalently joining two or more polypeptide epitopes using one or more linkers, wherein at least one of the epitopes comprises a post-translational modification. In one aspect, the surrogate compounds of the invention comprise a C-terminal epitope and a glycated epitope of human CD59. The inventive methods allow quantification of the levels of glycated CD59 in the serum in human subjects, particularly those with diabetes or pre-diabetes. This technological platform of post-translationally modified protein surrogates can be applied to other diseases associated with post-translationally modified proteins (e.g., autoimmune diseases such as multiple sclerosis, rheumatoid arthritis, and systemic lupus erythematosus). In another aspect, the invention provides antibodies that bind specifically to the compounds of the invention and methods for producing such antibodies.

15 Claims, 29 Drawing Sheets

| sample code | Experimental code | HbA1c | serum glucose (mg/dl) |
|---|---|---|---|
| LTR-01 | N1 | 4.8 | 92 |
| LTR-02 | N2 | 4.5 | 78 |
| LTR-03 | N3 | 4.7 | 94 |
| LTR-04 | N4 | 4.2 | 77 |
| LTR-05 | N5 | 4.7 | 90 |
| LTR-06 | N6 | 5.3 | 105 |
| LTR-07 | N7 | 5.5 | 79 |
| LTR-08 | N8 | 6.1 | 117 |
| LTR-09 | N9 | 4.5 | 86 |
| LTR-10 | N10 | 6 | 107 |
| 02-55-1 | D1 | 8 | 365 |
| 02-55-2 | D2 | 10.5 | 213 |
| 02-55-3 | D3 | 8.8 | 194 |
| 02-55-4 | D4 | 5.8 | 158 |
| 02-55-5 | D5 | 7.7 | 91 |
| 02-55-6 | D6 | 5.2 | 100 |
| 02-55-7 | D7 | 6.5 | 109 |
| 02-55-8 | D8 | 9.5 | 87 |
| 02-55-9 | D9 | 8.9 | 214 |
| 02-55-10 | D10 | 7.2 | 141 |
| DBB4062001 | D11 | 7.6 | 248 |

Fig. 24

Ac-NKAWK(Deoxyfructospyranosyl)-FEHANFNDC-OH (SEQ ID NO: 18)
Fig. 26A
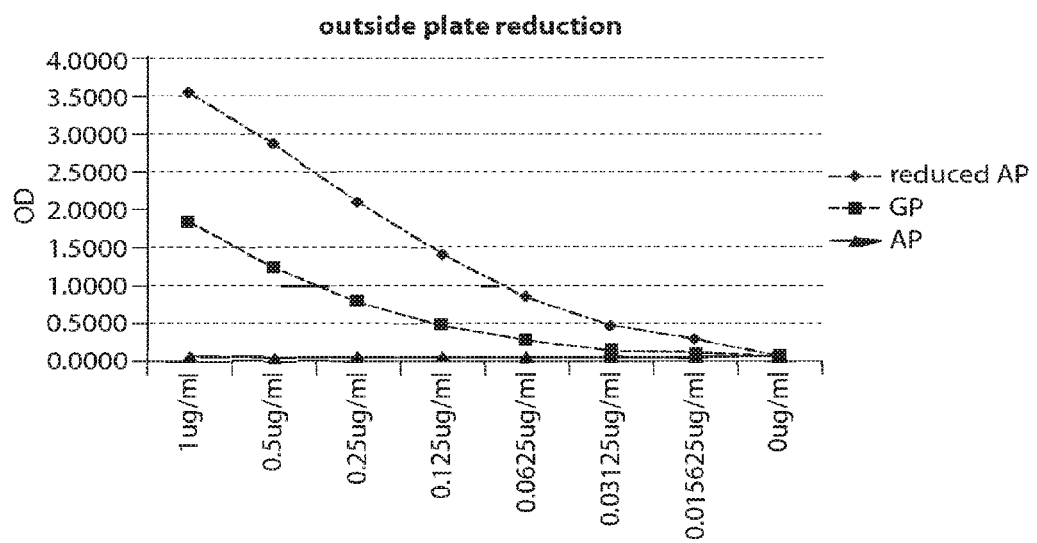
Fig. 26B
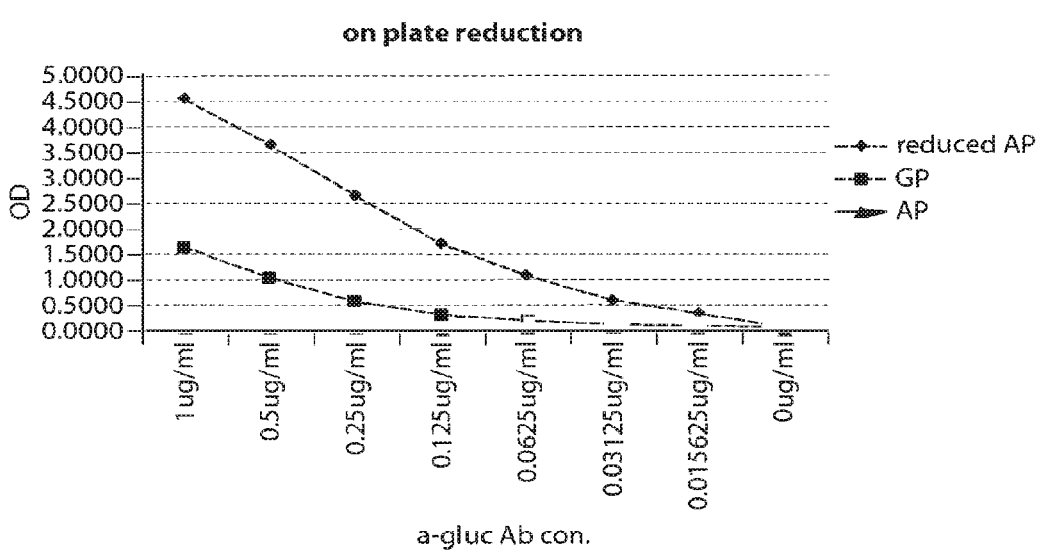
Fig. 26C

SURROGATES OF POST-TRANSLATIONALLY MODIFIED PROTEINS AND USES THEREOF

RELATED APPLICATIONS

The present application is the U.S. National Stacie of International Application No. PCT/US2012/24645, filed on Feb. 10, 2012, which claims priority under 35 U.S.C. §119(e) to U.S. provisional application, U.S. Ser. No. 61/441,575, filed Feb. 10, 2011, both of which are incorporated herein by reference.

BACKGROUND OF THE INVENTION

Post-translational modifications are chemical changes to a protein that occur after ribosomes have translated its primary structure. Post-translational modifications include, but are not limited to, glycation, phosphorylation, lipoylation, citrullination (e.g., in rheumatoid arthritis), hypusination (e.g., in diabetic inflammation), transglutamination (e.g., in celiac disease), and sumoylation (e.g., in cancer, neurodegenerative disease, and heart disease). Post-translational modifications influence protein behavior. For example, the post-translational addition or removal of phosphate moieties from proteins plays a regulatory role in many biochemical pathways and signal transduction pathways.

Numerous diseases inflicted or associated with post-translationally modified (PTM) proteins that are difficult to obtain in homogenous form. As such, PTM proteins could be used as biomarkers, namely diagnostic, prognostic and treatment monitoring tools in assessing the disease state of patients. Shortages of such endogenous PTM proteins can impede or prevent a convenient means to analyze PTM proteins. Thus, there is an unmet need to obtain synthetic constructs that can function as effective surrogates of endogenous PTM proteins. Such surrogates could be prepared in homogenous form to replace endogenous PTM proteins and serve as convenient standards, calibrators, and/or reference compounds that facilitate the detection and analysis of endogenous PTM proteins. Such surrogates could further be used to diagnose or monitor the progression of and/or efficacy of treatment of diseases associated with PTM proteins.

Diabetes mellitus (diabetes) is one such disease for which PTM proteins are well characterized. Diabetes is a leading cause of morbidity and mortality in the adult population. This is primarily because diabetic patients tend to develop vascular complications that involve the kidneys (diabetic nephropathy), the retina (diabetic retinopathy), as well as large and small blood vessels in other organs (macro- and microvascular disease) including nerves (diabetic neuropathy). It is well established that the vascular complications of diabetes are caused by elevated blood glucose levels over long periods of time. Elevated blood glucose levels contribute to the glycation of proteins. Glycation, the non-enzymatic covalent attachment of glucose to proteins, is considered a major post-translational modification causing tissue damage in diabetic subjects. Glycation involves the reaction of glucose and/or other reducing sugars with amino groups in proteins resulting in the formation of a Schiff's base or aldimine. This labile Schiff's base can cyclize to a more stable glycosylamine or rearrange and cyclize to Amadori adducts as shown below.

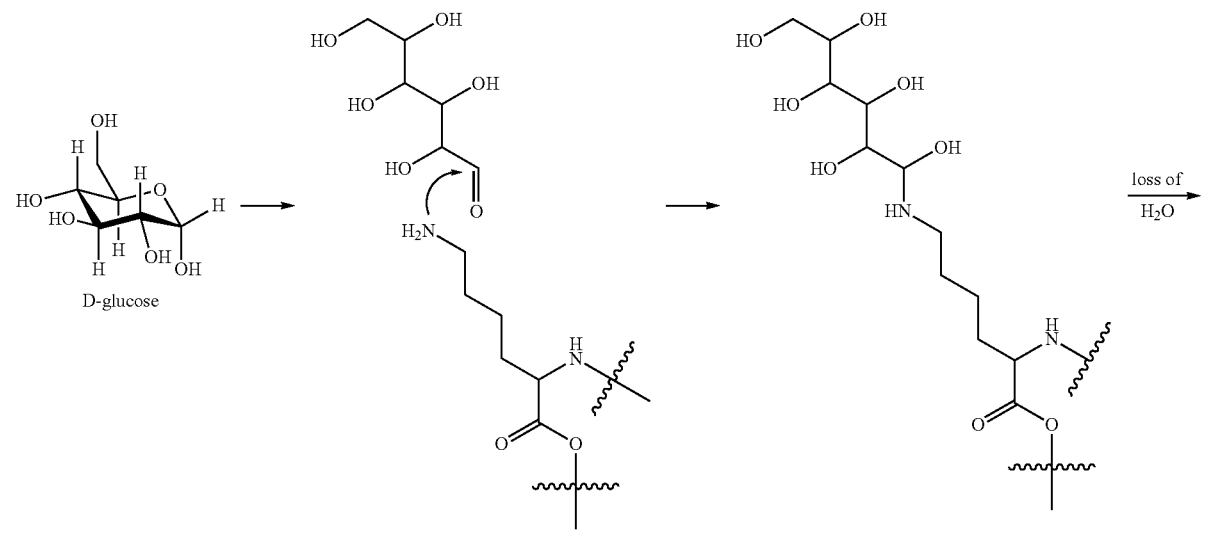

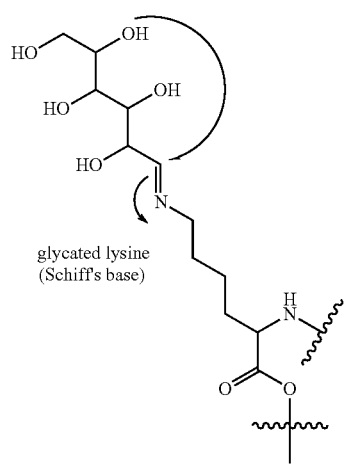

glycated lysine
(Schiff's base)

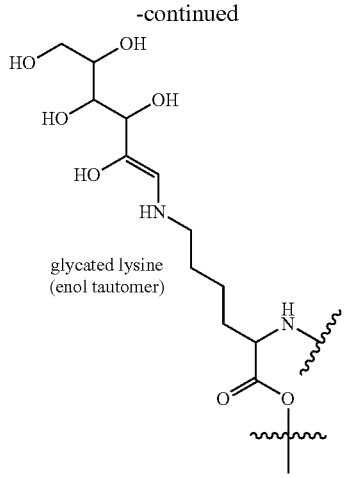

glycated lysine
(enol tautomer)

-continued

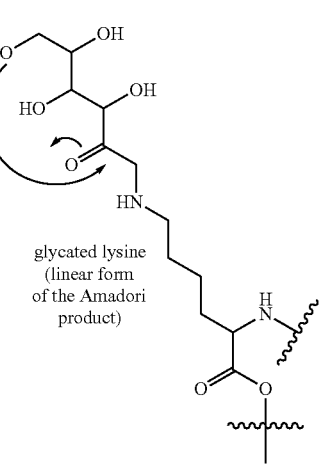

glycated lysine
(linear form
of the Amadori
product)

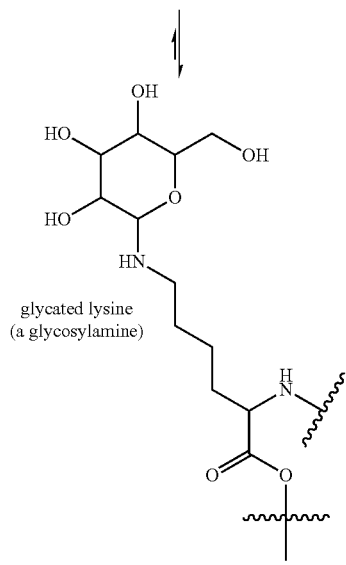

glycated lysine
(a glycosylamine)

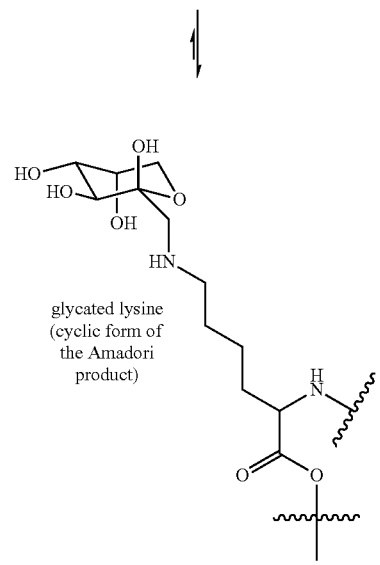

glycated lysine
(cyclic form of
the Amadori
product)

The function of the glycated protein may be impaired, depending on the location of the amino groups affected. Glycation of key regulatory proteins, such as those which prevent activation of the complement system (e.g., CD59), is believed to contribute to the clinical complications of diabetes mellitus. Thus, compositions and methods which help measure the extent of protein glycation of key regulatory proteins of the complement system such as CD59 are considered valuable clinical tools to detect prediabetics and diabetics, assess glycemic control and the efficacy of diabetes treatment.

SUMMARY OF THE INVENTION

The present invention provides compounds that are surrogates of post-translationally modified proteins and uses thereof. The inventive surrogate compounds may be prepared by covalently joining two or more polypeptide epitopes with one or more linkers, wherein at least one of the epitopes comprises a post-translational modification.

Thus, in one aspect, the present invention provides a compound comprising two or more antigenic epitopes of a protein joined by one or more linkers wherein:

each epitope is, independently, 1-100 amino acids in length;

at least one epitope comprises a post-translational modification;

the compound optionally comprises a label, wherein the label is a fluorogenic, phosphoregenic, chemiluminogenic, chromogenic, affinity-based, or radioactive;

each of the linkers is independently selected from the group consisting of cyclic or acyclic, substituted or unsubstituted, branched or unbranched aliphatic moiety; a cyclic or acyclic, substituted or unsubstituted, branched or unbranched heteroaliphatic moiety; substituted or unsubstituted, branched or unbranched acyl; substituted or unsubstituted, branched or unbranched aryl; substituted or unsubstituted, branched or unbranched heteroaryl; wherein each substituent is independently selected from the group consisting of branched and unbranched alkyl, branched and unbranched alkenyl, branched and unbranched alkynyl, heterocyclic, $-OR^A$; $-C(=O)R^A$; $-CO_2R^A$; $-SR^A$; $-SOR^A$; $-SO_2R^A$; $=O$; $=N(R^A)$; $=S$; $-N(R^A)_2$; $-NHC(=O)R^A$; $-NR^AC(=O)N(R^A)_2$; $-OC(=O)OR^A$; $-OC(=O)R^A$; $-OC(=O)N(R^A)_2$; or $-NR^AC(=O)OR^A$; wherein each occurrence of $R^A$ is independently a hydrogen, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In one embodiment each linker is, independently, of the formula:

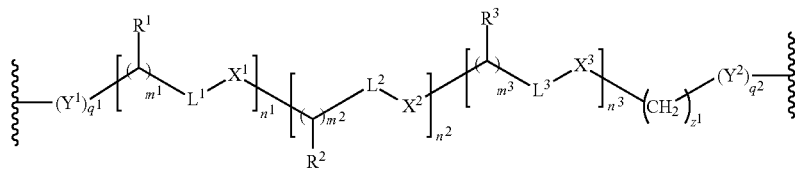

wherein
each of $R^1$, $R^2$, $R^3$, $L^1$, $L^2$, $L^3$, $X^1$, $X^2$, $X^3$, $m^1$, $m^2$, $m^3$, $n^1$, $n^2$, $n^3$, $q^1$, $q^2$, and $z^1$ is described herein.

In further embodiments, the linker is of the formula:

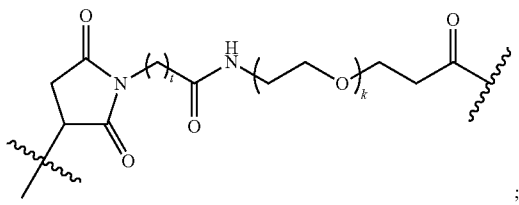

wherein
t is an integer from 1 to 12, inclusive, and
k is 0 or an integer from 1 to 100, inclusive.

In further embodiments, the linker is covalently bound to each antigenic epitope, independently, at either the C-terminus, N-terminus, or a side chain of an amino acid or an amino acid derivative of each antigenic epitope.

In one aspect, the present invention provides a method for detecting in a sample the presence of a protein with a post-translational modification motif, said method comprising obtaining a biological sample from a subject; measuring the amount of the reference compound in a reference sample using an antibody that detects the post-translationally modified motif; measuring the amount of post-translationally modified protein in the biological sample using the antibody; and comparing the amount of the reference compound in the reference sample with the amount of the protein in the biological sample.

In another aspect, the present invention provides a method for determining in a subject the regression, progression, or onset of a condition characterized by abnormal levels of a post-translationally modified protein with a post-translationally modified epitope, said method comprising obtaining a biological sample from the subject; measuring the amount of the reference compound in a reference sample using an antibody; measuring the amount, if any, of the post-translationally modified protein in the biological sample using the antibody; and comparing the amount of the reference compound in the reference sample with the amount of the protein in the biological sample.

In certain embodiments, the amount of the reference compound in the reference sample is determined by detecting a reporter signal generated by the reference compound. In further embodiments, the condition is selected from the group consisting of diabetes, an autoimmune disease, multiple sclerosis, rheumatoid arthritis, systemic lupus erythematosus, primary bilary cirrhosis, celiac disease, Crohn's disease, and other diseases associated with the presence of abberent PTM proteins.

In still further embodiments, the step of measuring the amount of the reference compound in the reference sample is determined by contacting a first capture antibody immobilized to a surface with the reference sample, said capture antibody targeting an antigenic epitope common to the apoprotein and the PTM version of it, which is not overlapping with the post-translationally modified epitope of the reference compound in the reference sample; contacting the reference compound that is immobilized on the surface by the capture antibody with a primary detecting antibody, said primary detecting antibody targeting the post-translationally modified epitope of the reference compound; and contacting the reference compound that is immobilized on the surface by the capture antibody with a secondary detecting antibody that can quantify the PTM antigen, said quantifying antibody targeting said detecting antibody.

In another aspect, the invention provides an antibody or antibody fragment that binds specifically to the compounds of the invention and methods for producing such antibodies. In some embodiments, the antibody or antibody fragment binds specifically to post-translationally modified epitopes of the compounds of the invention, wherein the post-translational modification is selected from the group consisting of glycation, phosphorylation, lipoylation, citrullination, hypusination, transglutamination, and sumoylation.

In another aspect, the present invention provides a kit for detecting the presence of a post-translationally modified protein in a biological sample, said kit comprising a first container with a reference sample comprising a reference compound of the invention, and instructional material for use of said kit. The kit may further comprise: a capture antibody, said capture antibody binding to an epitope other than the post-translationally modified epitope of the reference compound; a primary detecting antibody, said detection antibody directed to the post-translationally modified epitope of the reference compound; a quantifying secondary detecting antibody, said quantifying antibody binding to said primary detecting antibody. A kit may comprise any of a number of additional reagents, buffering agents, containers, and/or controls in any combination. All of the various combinations are not set forth explicitly but each combination is included in the scope of the invention.

In certain embodiments, the present invention provides compounds prepared from a synthetic precursor of the linker of the formula:

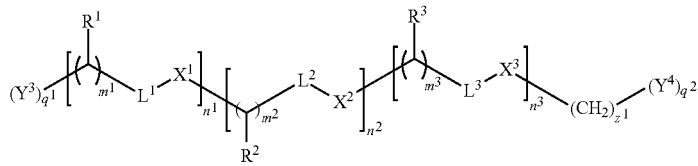

wherein each of $R^1$, $R^2$, $R^3$, $L^1$, $L^2$, $L^3$, $X^1$, $X^2$, $X^3$, $m^1$, $m^2$, $m^3$, $n^1$, $n^2$, $n^3$, $q^1$, $q^2$, and $z^1$ is described herein.

In certain embodiments, an epitope of the compound is derived from human CD59. In still further embodiments, the compound comprises two epitopes of human CD59 joined by a linker. In further embodiments, one of the epitopes comprises a glycation motif. In still further embodiments, the second epitope is a peptide segment selected from residues 44-66 of human CD59. In still further embodiments, the glycation motif is $R^1$—$K_{41}$—$R^2$, wherein $R^1$ is absent or a peptide sequence which is identical or homologous to a peptide sequence selected from residues 30-40 of human CD59; $R^2$ is absent or a peptide sequence which is identical or homologous to a peptide sequence selected from residues 42-60 of human CD59. In certain embodiments, the glycation motif is $NKAWK_{41}FEHANFNDC$. In further embodiments, $K_{41}$ is glycated. In certain preferred embodiments, $K_{41}$ is modified with the linear Schiff or Amadori glycated product that are reduced to $N^\epsilon$-(1-deoxy-D-glucitol-1-yl)L-lysine (the glucitollysine moiety), as shown below.

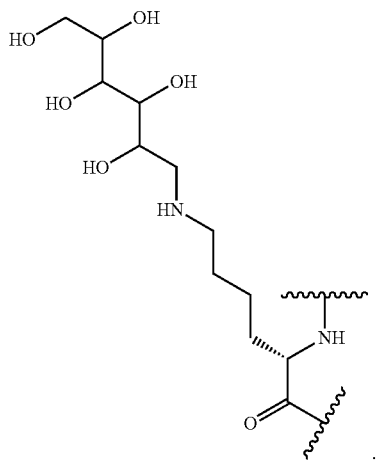 [SMILES: *N[C@@H](CCCCNCC(O)C(O)C(O)C(O)CO)C(*)=O]

This application refers to various issued patents, published patent applications, journal articles, and other publications, all of which are incorporated herein by reference. If there is a conflict between any of the incorporated references and the instant specification, the specification shall control. The details of one or more embodiments of the invention are set forth in the accompanying "Figures" and the "Detailed Description of Certain Embodiments of the Invention," as described below. Other features, objects, and advanlabeles of the invention will be apparent from the description, the figures, and from the claims.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3rd Edition, Cambridge University Press, Cambridge, 1987.

The compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

Where an isomer/enantiomer is preferred, it may, in certain embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of diastereomeric salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substitutents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

One of ordinary skill in the art will appreciate that the synthetic methods, as described herein, utilize a variety of protecting groups. By the term "protecting group," as used herein, it is meant that a particular functional moiety, e.g., O, S, or N, is temporarily blocked so that a reaction can be carried out selectively at another reactive site in a multifunctional compound. "Protecting groups," as used herein, are well known in the art and include those described in detail in *Protective Groups in Organic Synthesis*, Fourth Ed., Greene, T. W. and Wuts, P. G., Eds., John Wiley & Sons, New York: 2007, the entire contents of which are hereby incorporated by reference.

A "suitable amino protecting group," as used herein, is well known in the art and include those described in detail in Greene et al. Suitable amino protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group" or "protected carboxylic acid," as used herein, are well known in the art and include those described in detail in Greene et al. Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group," as used herein, is well known in the art and include those described in detail in Greene et al. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl) benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N, N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in Greene et al. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers.

Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxycrotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

As used herein, substituent names which end in the suffix "-ene" refer to a biradical derived from the removal of two hydrogen atoms from the substituent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula $—C(=O)R^{X1}$, $—C(=O)OR^{X1}$, $—C(=O)—O—C(=O)R^{X1}$, $—C(=O)SR^{X1}$, $—C(=O)N(R^{X1})_2$, $—C(=S)R^{X1}$, $—C(=S)N(R^{X1})_2$, and $—C(=S)S(R^{X1})$, $—C(=NR^{X1})R^{X1}$, $—C(=NR^{X1})OR^{X1}$, $—C(=NR^{X1})SR^{X1}$, and $—C(=NR^{X1})N(R^{X1})_2$, wherein $R^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein R$^i$ is an optionally substituted acyl group, as defined herein, and the oxygen moiety is directly attached to the parent molecule.

The term "aliphatic," as used herein, includes both saturated and unsaturated, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In certain embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-6 carbon atoms. Examples of alkyl radicals include, but are not limited to, methyl, ethyl, n-propyl, isopropyl, cyclopropyl, —CH$_2$-cyclopropyl, vinyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which may bear one or more sustitutents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In certain embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In certain embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkoxy" refers to a "substituted hydroxyl" of the formula (—$OR^i$), wherein $R^i$ is an optionally substituted alkyl group, as defined herein, and the oxygen moiety is directly attached to the parent molecule. Examples of alkoxy, include but are not limited to, methoxy, ethoxy, propoxy, isopropoxy, n-butoxy, tert-butoxy, neopentoxy, and n-hexoxy.

The term "alkylthioxy" refers to a "substituted thiol" of the formula (—$SR^r$), wherein $R^r$ is an optionally substituted alkyl group, as defined herein, and the sulfur moiety is directly attached to the parent molecule. Examples of alkylthioxy include, but are not limited to, methylthio, ethylthio, propylthio, isopropylthio, n-butylthio, and the like.

The term "amino," as used herein, refers to a group of the formula (—$NH_2$). A "substituted amino" refers either to a mono-substituted amine (—$NHR^h$) of a disubstitued amine (—$NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the di-substituted amino group (—$NR^h_2$) form a 5- to 6-membered hetereocyclic ring.

The term "alkylamino" refers to a "substituted amino" of the formula (—$NR^h_2$), wherein $R^h$ is, independently, a hydrogen or an optionally substituted alkyl group, as defined herein, and the nitrogen moiety is directly attached to the parent molecule. In certain embodiments, the aliphatic group contains 1-20 aliphatic carbon atoms. In certain other embodiments, the aliphatic group contains 1-10 aliphatic carbon atoms. In yet other embodiments, the aliphatic group employed in the invention contain 1-8 aliphatic carbon atoms. In still other embodiments, the aliphatic group contains 1-6 aliphatic carbon atoms. In yet other embodiments, the aliphatic group contains 1-4 aliphatic carbon atoms. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each an aliphatic group, as defined herein. R and R' may be the same or different in an dialkyamino moiety. In certain embodiments, the aliphatic groups contains 1-20 aliphatic carbon atoms. In certain other embodiments, the aliphatic groups contains 1-10 aliphatic carbon atoms. In yet other embodiments, the aliphatic groups employed in the invention contain 1-8 aliphatic carbon atoms. In still other embodiments, the aliphatic groups contains 1-6 aliphatic carbon atoms. In yet other embodiments, the aliphatic groups contains 1-4 aliphatic carbon atoms. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limted to, aziridinyl, pyrrolidinyl, piperidinyl, morpholinyl, pyrrolyl, imidazolyl, 1,3,4-trianolyl, and tetrazolyl.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "haloaryl," as used herein, refers to a halo substituted aryl group, with one or more halo substituents, wherein the terms "aryl" and "halo" are defined herein, and wherein the aryl group is attached to the parent molecule. An exemplary haloaryl group includes the pentachlorophenyl group.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "arylamino," refers to a "substituted amino" of the formula (—$NR^h_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula (—$SR^r$), wherein $R^r$ is an optionally substituted aryl group, as defined herein, and the sulfur moiety is directly attached to the parent molecule.

The term "azido," as used herein, refers to a group of the formula (—$N_3$).

The term "cyano," as used herein, refers to a group of the formula (—CN).

The terms "halo" and "halogen" as used herein refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkylamino" refers to a "substituted amino" of the formula (—$NR^h_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—$OR^i$), wherein $R^i$ is an optionally substituted heteroalkyl group, as defined herein, and the oxygen moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocyclyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the (—NR$^h{}_2$), wherein R$^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula (—OR$^i$), wherein R$^i$ is an optionally substituted heteroaryl group, as defined herein, and the oxygen moiety is directly attached to the parent molecule.

The term "hydroxy" or "hydroxyl," as used herein, refers to a group of the formula (—OH). A "substituted hydroxyl" refers to a group of the formula (—OR$^i$), wherein R$^i$ can be any substituent which results in a stable moiety (e.g., a suitable hydroxyl protecting group, aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula (=NR$^r$), wherein R$^r$ corresponds to hydrogen or any substitutent as described herein, that results in the formation of a stable moiety (for example, a suitable amino protecting group, aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted). In certain embodiments, imino refers to =NH wherein R$^r$ is hydrogen.

The term "independently selected" is used herein to indicate that the R groups can be identical or different.

As used herein, the term "label" is intended to mean that a compound has at least one element, isotope, or chemical compound attached to enable the detection of the compound. In general, labels typically fall into five classes: a) isotopic labels, which may be radioactive or heavy isotopes, including, but not limited to, $^2$H, $^3$H, $^{13}$C, $^{14}$C, $^{15}$N, $^{31}$P, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; c) colored, luminescent, phosphorescent, or fluorescent dyes; d) photoaffinity labels; and e) ligands with known binding partners (such as biotin-streptavidin, FK506-FKBP, etc.). It will be appreciated that the labels may be incorporated into the compound at any position that does not interfere with the biological activity or characteristic of the compound that is being detected. In certain embodiments, hydrogen atoms in the compound are replaced with deuterium atoms ($^2$H) to slow the degradation of the compound in vivo. Due to isotope effects, enzymatic degradation of the deuterated compounds may be slowed thereby increasing the half-life of the compound in vivo. In other embodiments such as in the identification of the biological target(s) of a natural product or derivative thereof, the compound is labeled with a radioactive isotope, preferably an isotope which emits detectable particles, such as β particles. In certain other embodiments of the invention, photoaffinity labeling is utilized for the direct elucidation of intermolecular interactions in biological systems. A variety of known photophores can be employed, most relying on photoconversion of diazo compounds, azides, or diazirines to nitrenes or carbenes (see, Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to, 4-azido-2,3,5,6-tetrafluorobenzoic acid. In other embodiments, a biotin label is utilized.

The term "nitro," as used herein, refers to a group of the formula (—NO$_2$).

The term "oxo," as used herein, refers to a group of the formula (=O).

The term "stable moiety," as used herein, preferably refers to a moiety which possess stability sufficient to allow manufacture, and which maintains its integrity for a sufficient period of time to be useful for the purposes detailed herein.

As used herein, the term "tautomers" are particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

The term "thio" or "thiol," as used herein, refers to a group of the formula (—SH). A "substituted thiol" refers to a group of the formula (—SR'), wherein R' can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "thiooxo," as used herein, refers to a group of the formula (═S).

The term "subject," as used herein, refers to any animal. In certain embodiments, the subject is a mammal. In certain embodiments, the term "subject," as used herein, refers to a human (e.g., male, female, adult, or child). The subject may be at any stage of development.

The term animal, as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). The animal may be male or female and at any stage of development. A non-human animal may be a transgenic animal.

The terms "protein," "peptide," and "polypeptide" as used herein, refer to a string of at least three amino acids linked together by peptide bonds. The terms "protein," "peptide," and "polypeptide" may be used interchangeably. Peptide may refer to an individual peptide or a collection of peptides. Peptides typically contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modifications.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$, and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

As used herein, the term "buffering agent" includes, but is not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

[M+3H]$^{+3}$ molecular ion peaks associated with glycated and reduced human CD59[37-50] antigen.

Figure 9:
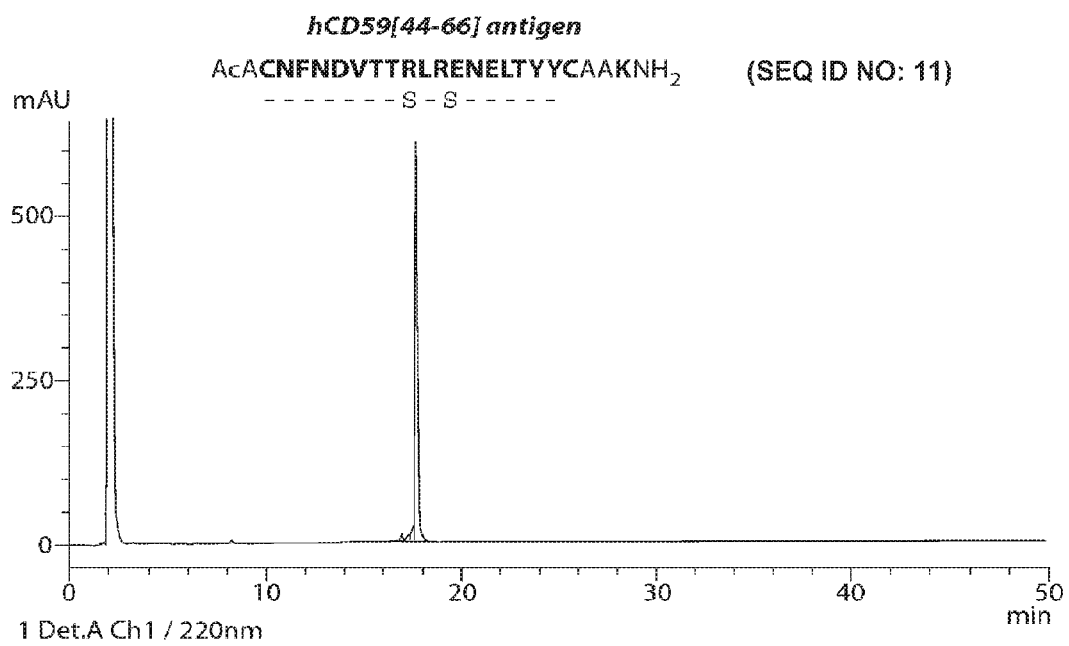

FIG. 9 depicts a HPLC trace for the human CD59[44-66] antigen. Conditions: 0.12 mg in 5 μL AcOH+29 μL MeCN/TFA/H$_2$O degassed; Injection Volume: 6 μL; Gradient: 10-60% in 50 min.; Column: Vydac C18, 218TP54 (4.6 mm i.d., 250 mL); Buffer: A: 0.05% TFA in H$_2$O; B: 0.05% TFA in MeCN; Flow: 1 mL/min.

Figure 10:
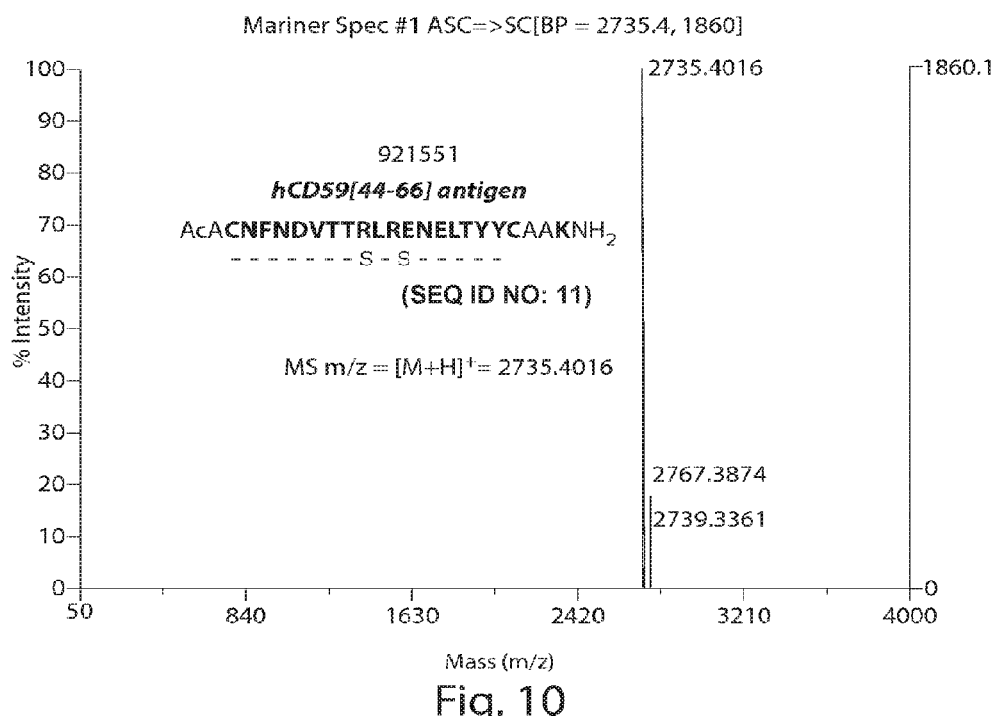
Figure 11:
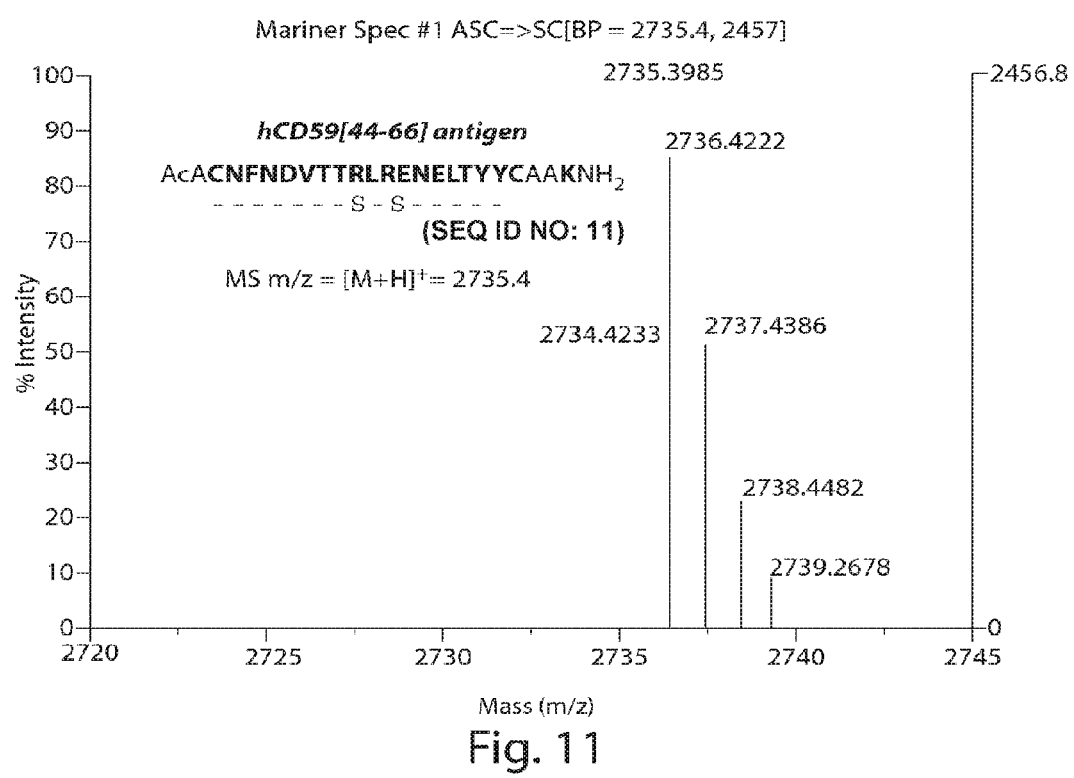

FIGS. 10-11 depict electrospray ionization mass spectrum m/z=2735.40 [M+H]$^+$ molecular ion peaks associated with human CD59[44-66] antigen.

Figure 12:
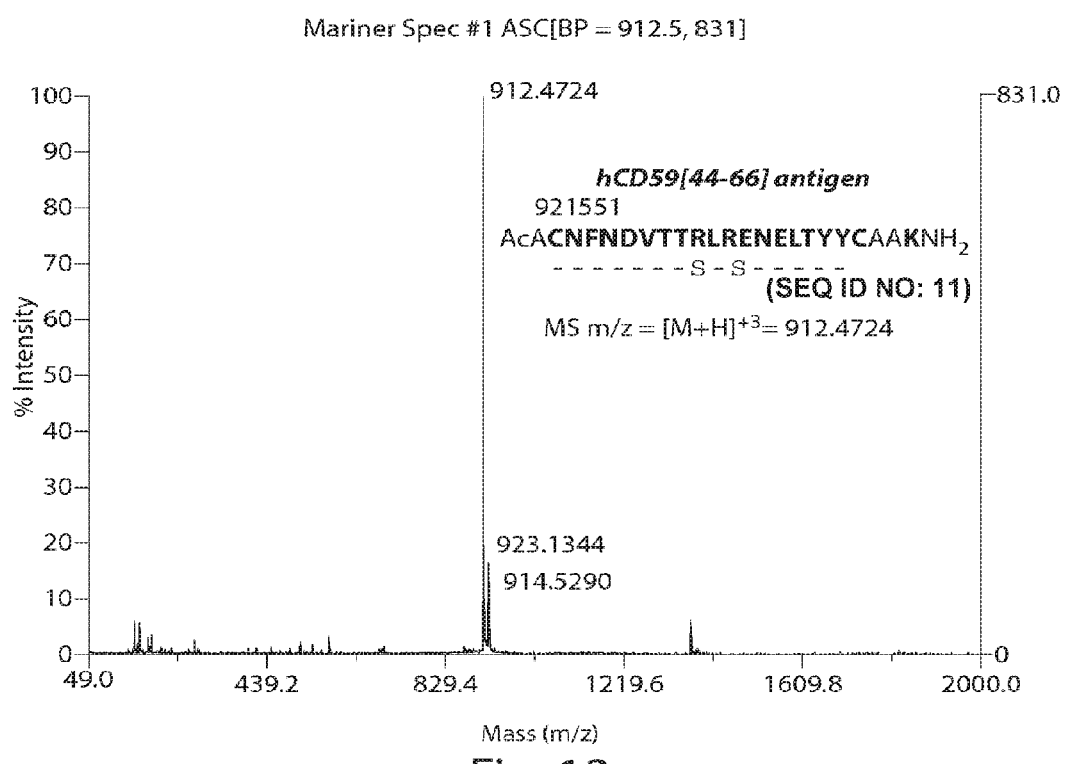

FIG. 12 depicts an electrospray ionization mass spectrum m/z=912.47 [M+3H]$^{+3}$ molecular ion peak associated with human CD59[44-66] antigen.

Figure 13:
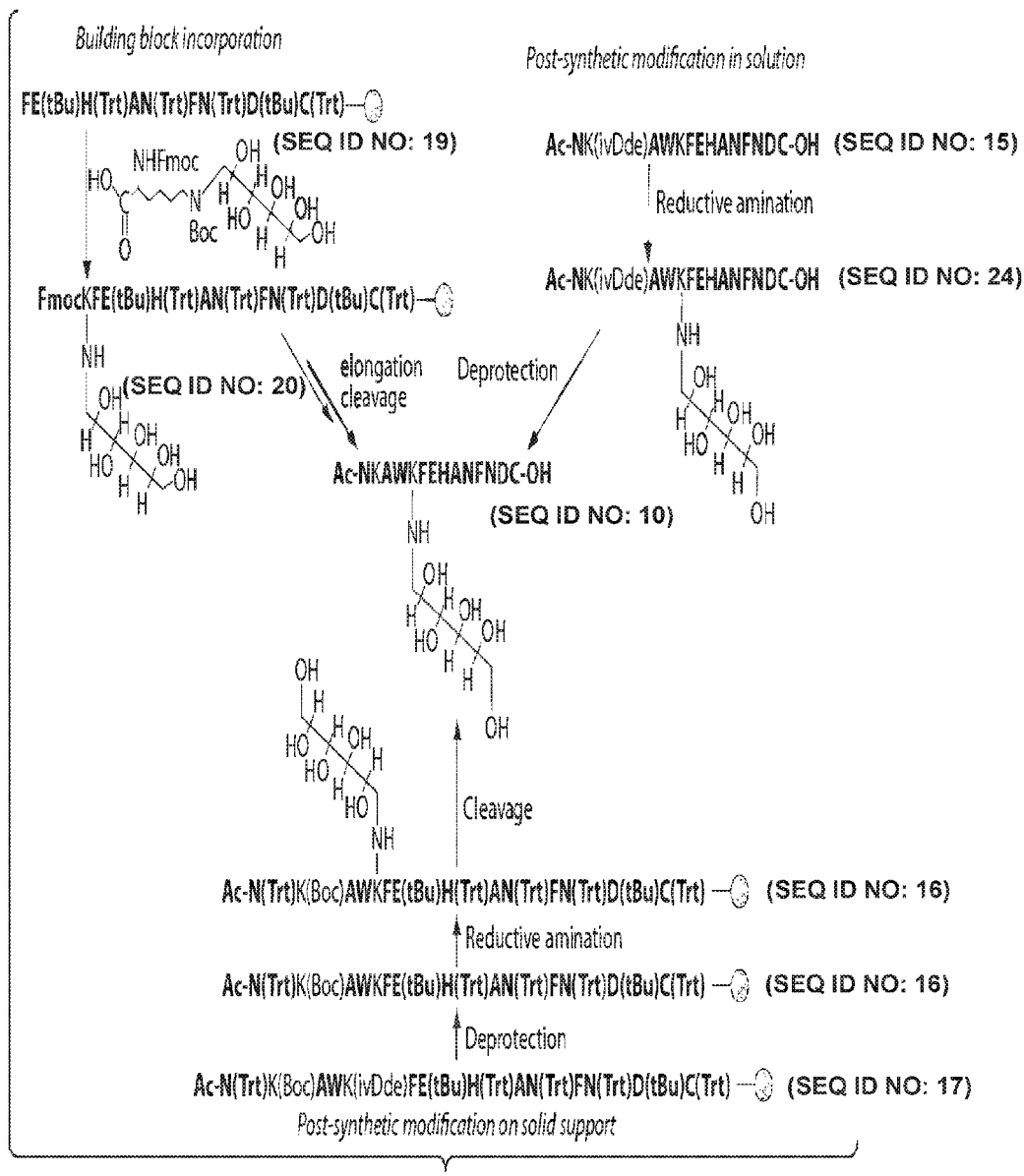

FIG. 13 depicts synthetic approaches for generating the site specific-glycated and reduced human CD59 antigen Ac[Ala$^{39,45}$, Lys$^{41}$ (N$^\epsilon$-1-deoxy-D-glucitol-1-yl), Cys$^{50}$] CD59(37-50).

Figure 14:
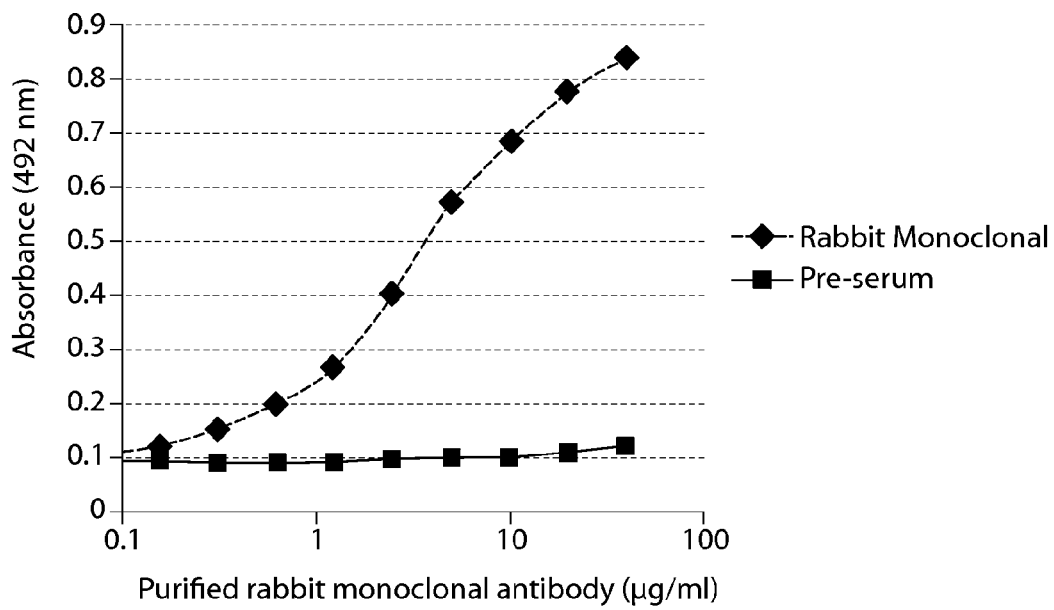

FIG. 14 depicts purified rabbit monoclonal antibody that was titrated against glycated-BSA. The purified rabbit monoclonal antibody was initially diluted to 40 mg/ml and then further diluted on ELISA plate. Pre-immune serum form the same rabbit was used as control. The pre-immune serum was initially diluted 1:100 and then diluted further on ELISA plate.

Figure 15:
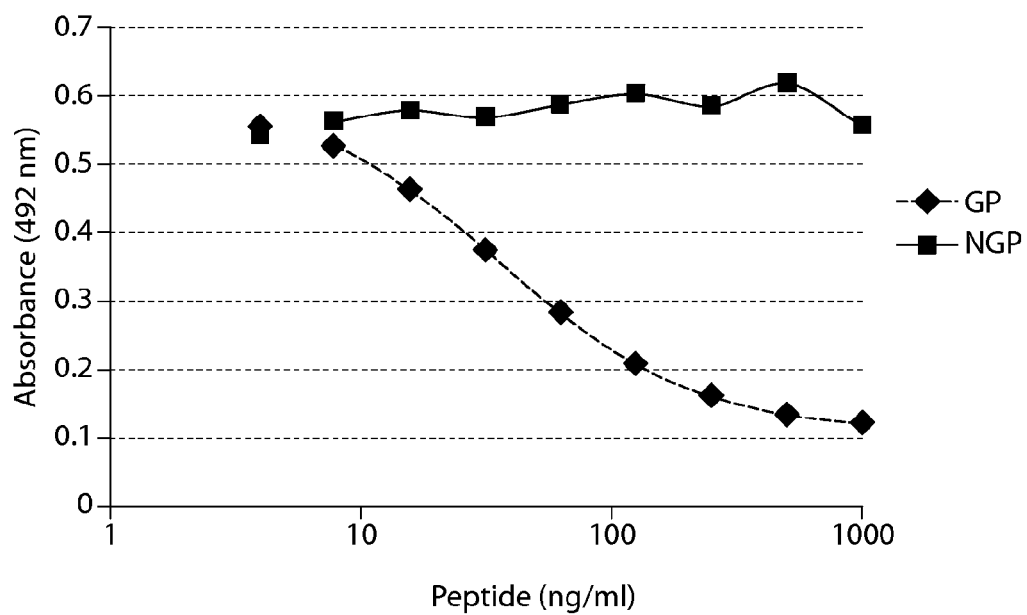

FIG. 15 depicts a competition ELISA assay in which the free peptide present in solution competes with the glycated-BSA bound to the plate. The peptide-monoclonal antibody complex remains in solution and gets washed away in subsequent washes, whereas the monoclonal antibody bound to glycated-BSA remains bound to the ELISA plate well and contributes to the color which is read at 492 nm. Because the non-glycated peptide does not contain any glucitolysine moiety, it does not competes with the glycated-BSA and hence increasing concentration of non-glycated peptide does not result in any drop in color production.

Figure 16:
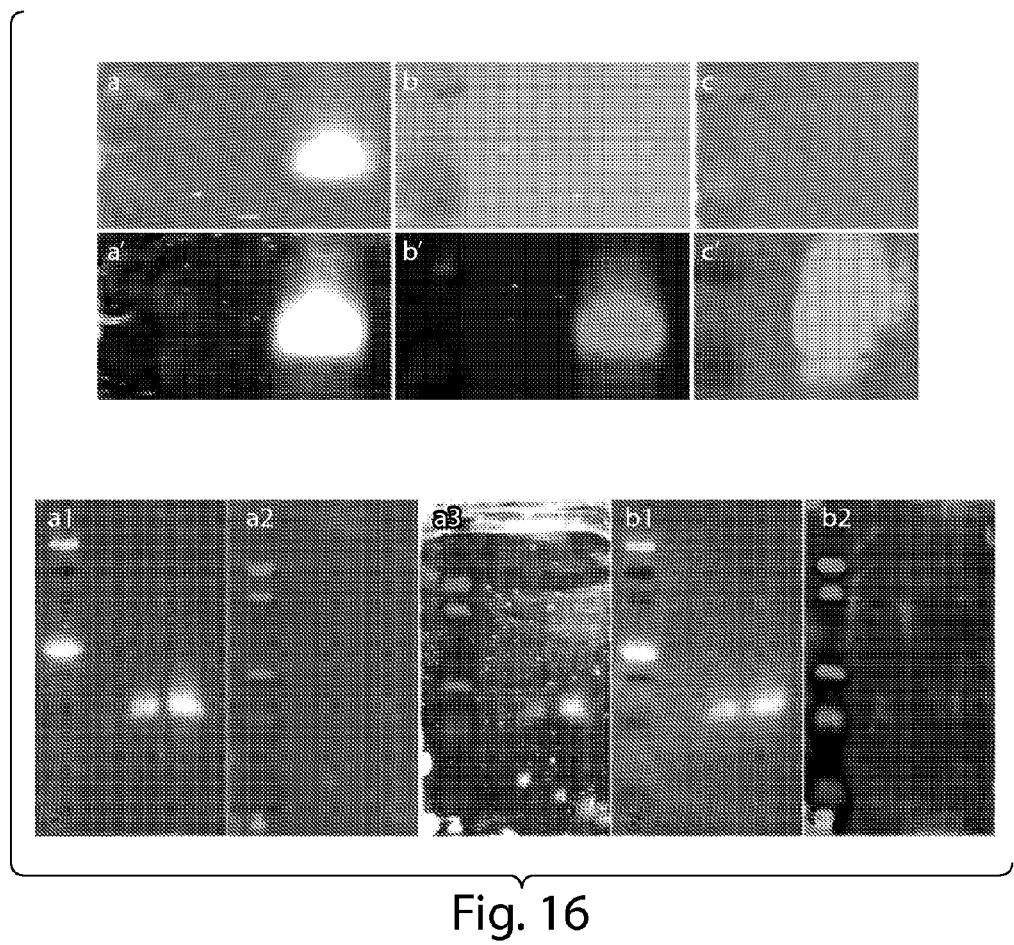

FIG. 16 depicts purified urine hCD59 (2 and 4 μg) that was separated on a 15% SDS-PAGE gel and trans-blotted onto a PVDF membrane. One such blot was reduced with sodium borohydride and then stained with Sypro ruby to confirm transfer of proteins (a1). A similar blot (b1) that was not reduced with sodium borohydride served as a control. After blocking, the blot that was reduced with sodium borohydride was first exposed to anti-rabbit antibody labeled with IRDye-800 to rule out any irrelevant binding (a2). The two blots were then exposed to rabbit monoclonal at a concentration of 1 μg/ml for two hours at room temperature followed by exposure to anti-rabbit antibody labeled with IRDye-800 (a3 and b2).

Figure 17A:
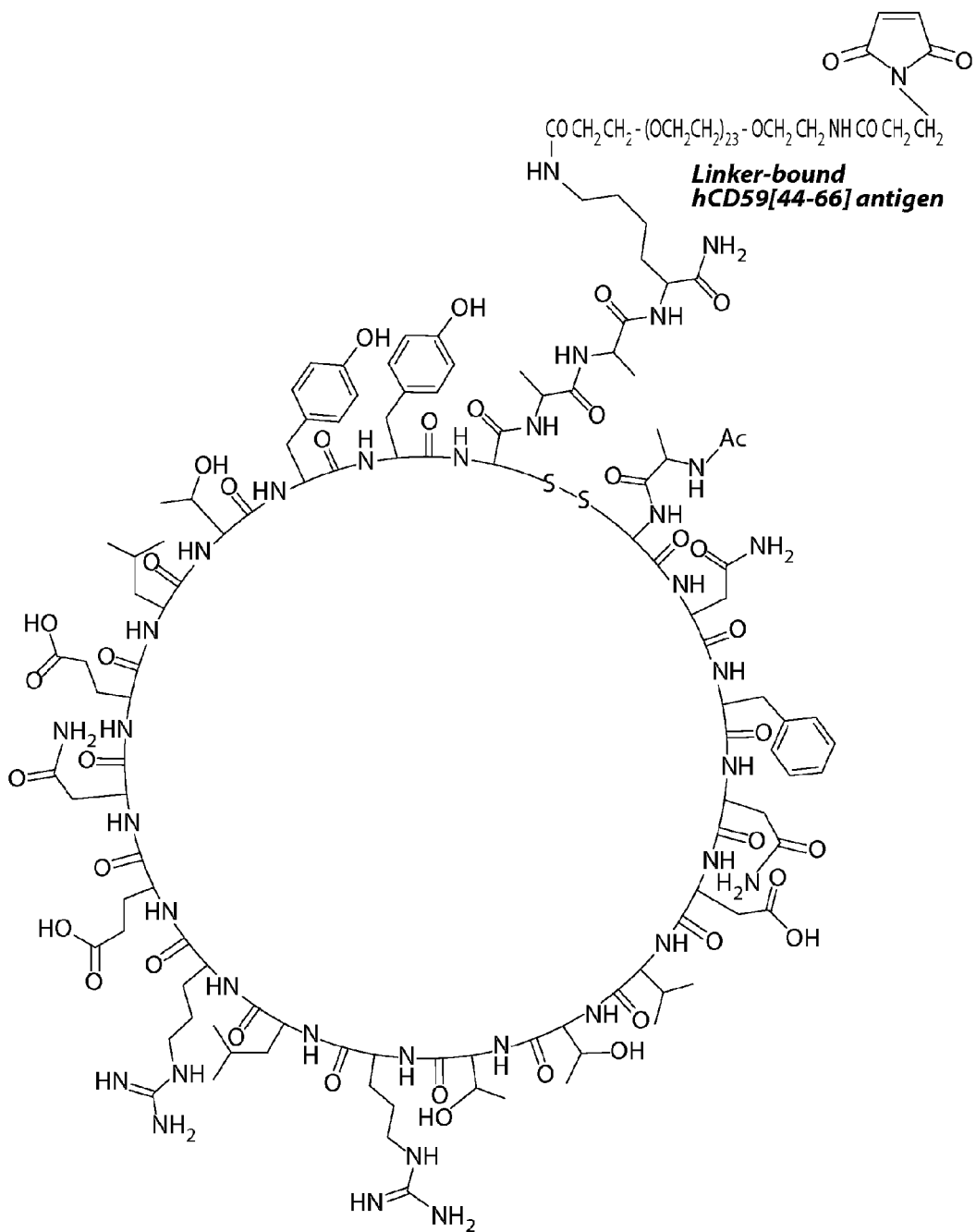
Figure 17B:
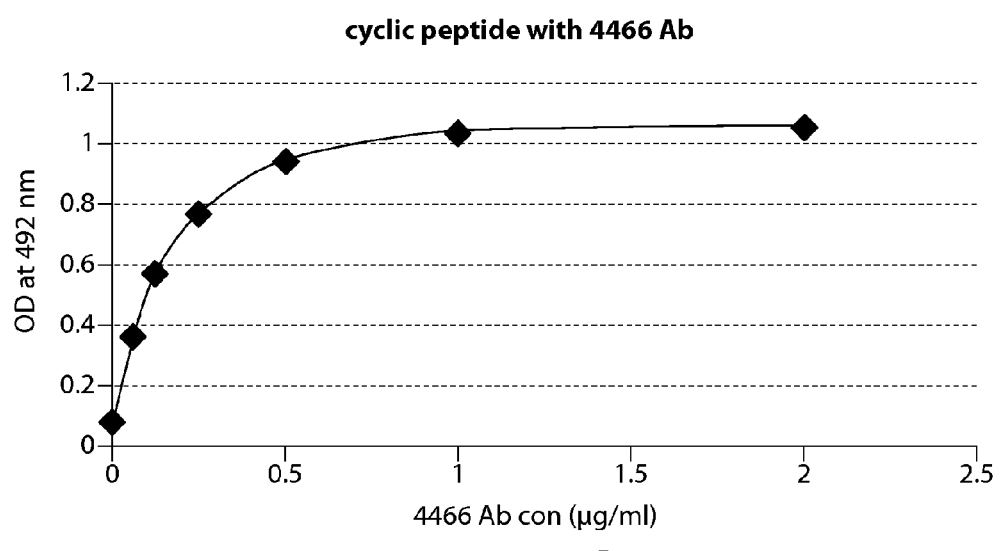

FIG. 17 depicts (A) the structure of the linker-bound hCD59[44-66] antigen and (B) the titration curve of the linker-bound hCD59[44-66] antigen in an ELISA. Coating Antigens: linker-bound hCD59[44-66] antigen (200 ng/mL solution; 0.1 mL/well=20 ng/well) coated for 1 hour at room temperature. Blocking: All wells were blocked with protein free blocking buffer (0.2 mL for 1 hour). Primary Antibody: 4466-10A7 mouse mAb (mouse anti-human CD59[44-66] mAb) (4.2 mg/mL) for 1 hour at room temperature, Ab diluent was 10% protein free blocking buffer. Detection Antibody: goat anti-mouse HRP-tagged IgG (Caltec) (1:1000) 1 hour at room temperature, Ab diluent was 10% protein free blocking buffer.

Figure 18:
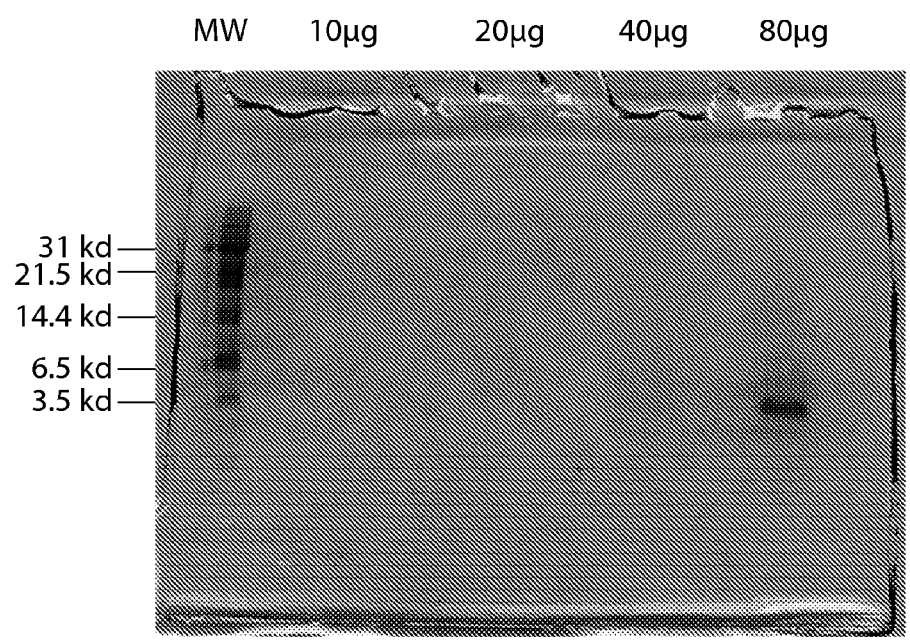

FIG. 18 depicts PAGE analysis of the glycated and reduced human CD59 surrogate (10 mg/ml in PBS) on 16.5% Tric-Tricine Ready gel (Bio-Rad #161-0989) following overnight staining with coomassie.

Figure 19A:
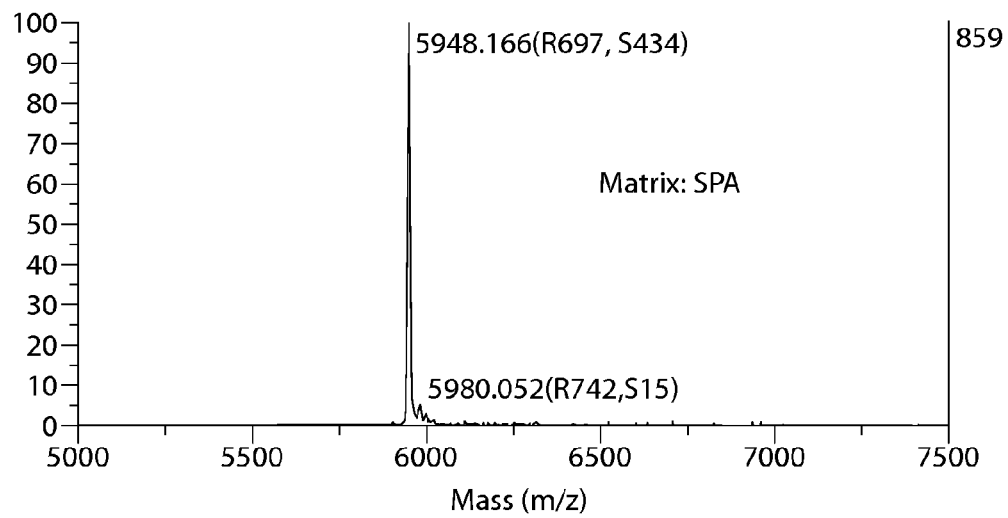
Figure 19B:
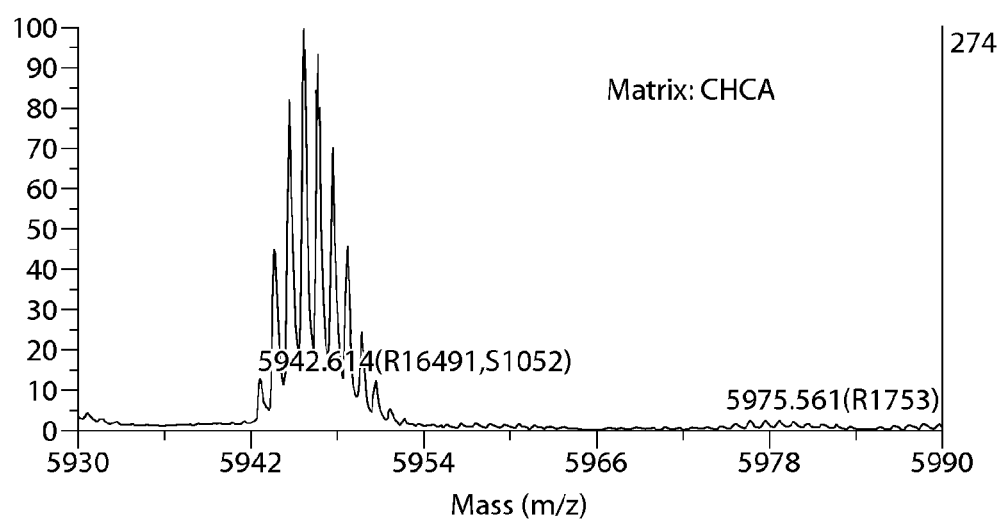

FIG. 19 depicts MALDI-MS analysis of the glycated and reduced human CD59 surrogate sampled in either SPA (sinapinic acid) matrix m/z=5948.17 [M+H]$^+$ (A) or the CHCA (α-cyano-4-hydroxycinnamic acid) matrix m/z=centered around 5948 (B).

Figure 20:
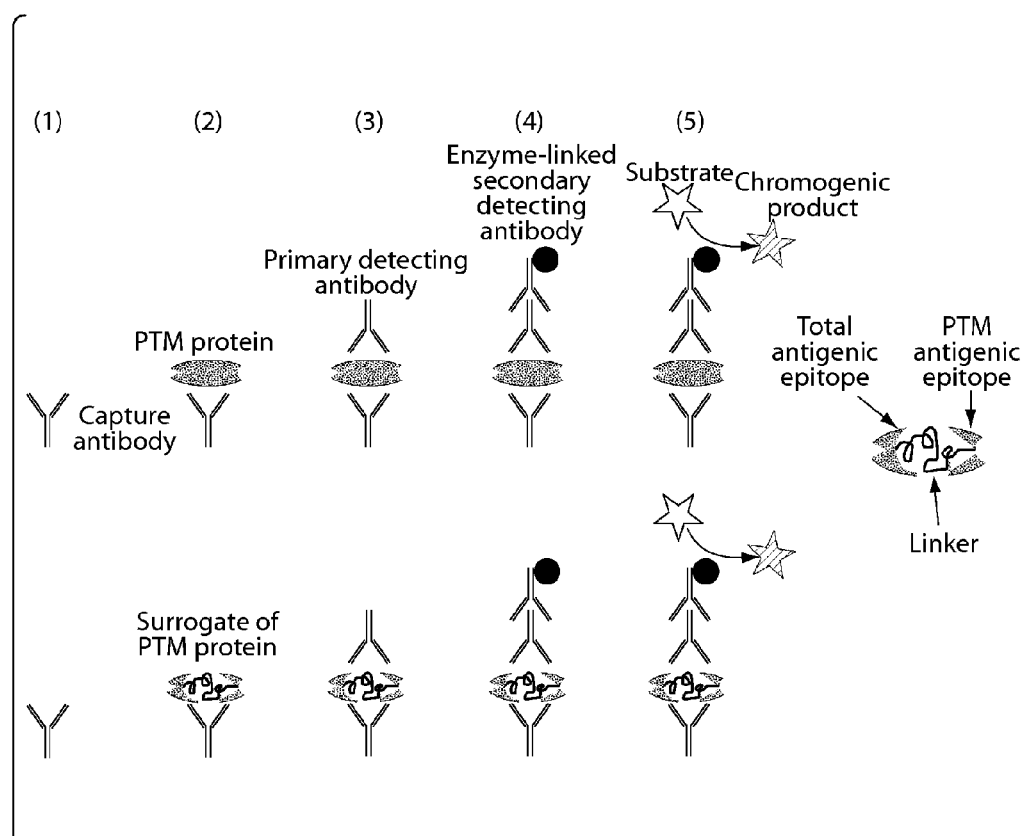

FIG. 20 depicts schematics of sandwich ELISA of PTM protein (A) and PTM protein surrogate employing the same capturing-, primary detecting- and enzyme-linked secondary detecting antibodies. The PTM protein surrogate is composed of a total antigenic epitope and a non-overlapping PTM antigenic epitope that are connected by a flexible linker.

Figure 21:
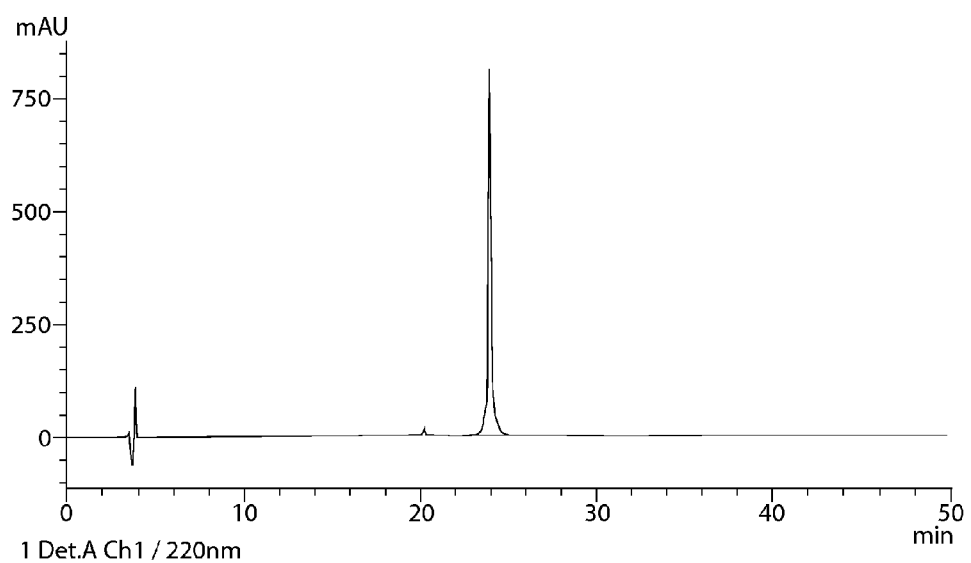

FIG. 21 depicts a HPLC trace for the hybrid peptide surrogate of post-translationally modified: glycated and reduced hCD59-surrogate. Conditions: 0.50 mg in 500 μL H$_2$O/MeOH; Injection Volume: 36 μL; Gradient: 10-60% in 50 min.; Column: Jupiter 5u, C18, 300 Å, (4.6 mm i.d., 250 mL); Buffer: A: 0.05% TFA in H$_2$O; B: 0.05% TFA in MeCN; Flow: 1 mL/min.

Figure 22:
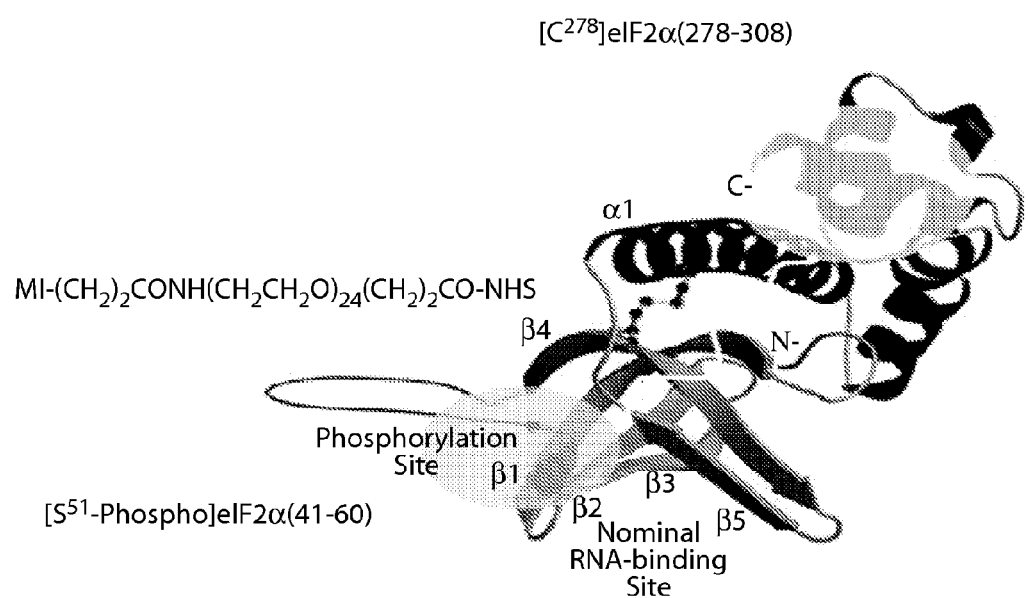

FIG. 22 depicts the design of a [S$^{51}$-phospho]eIF2α-surrogate. Shown is a heterobifunctional polyethyleneoxide linker MI-(CH$_2$)$_2$CONH(CH$_2$CH$_2$O)$_{24}$(CH$_2$)$_2$CO—NHS, where MI and NHS are a maleimido and an N-hydroxysuccinimido moieties. Also shown is human eIF2α, a subunit of the eukaryotic initiation factor 2. Highlighted on eIF2α are two non-overlapping antigenic sequences derived from human [S$^{51}$-phospho]eIF2α(41-60) and the carboxyl-terminal sequence of human [C$^{278}$]eIF2α(278-308). The MI moiety will bind specifically to the side chain of [C$^{278}$] in the carboxyl-terminal fragment and the NHS moiety will bind specifically to K$^{60}$ in the S$^{51}$-containing fragment of eIF2α.

Figure 23A:
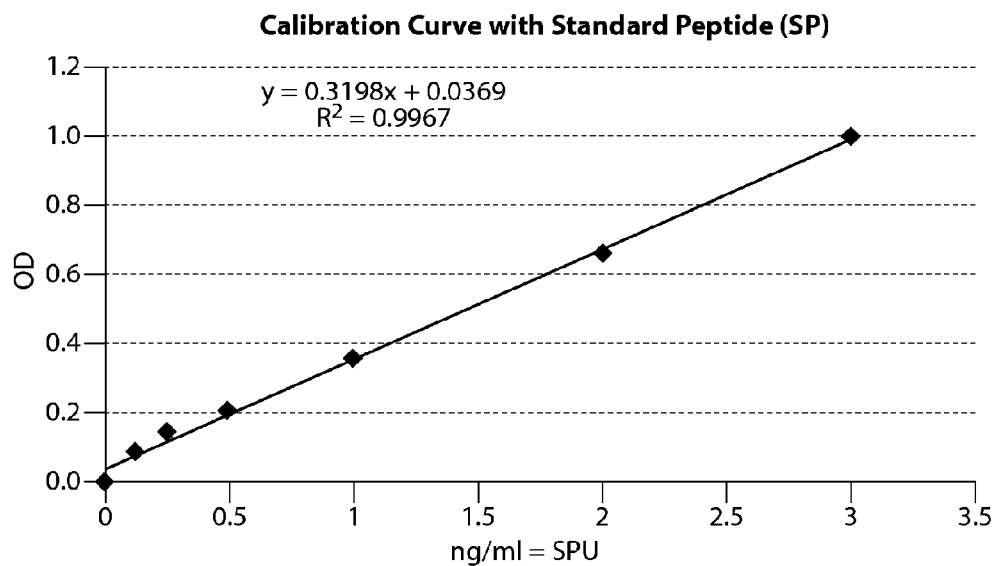
Figure 23B:
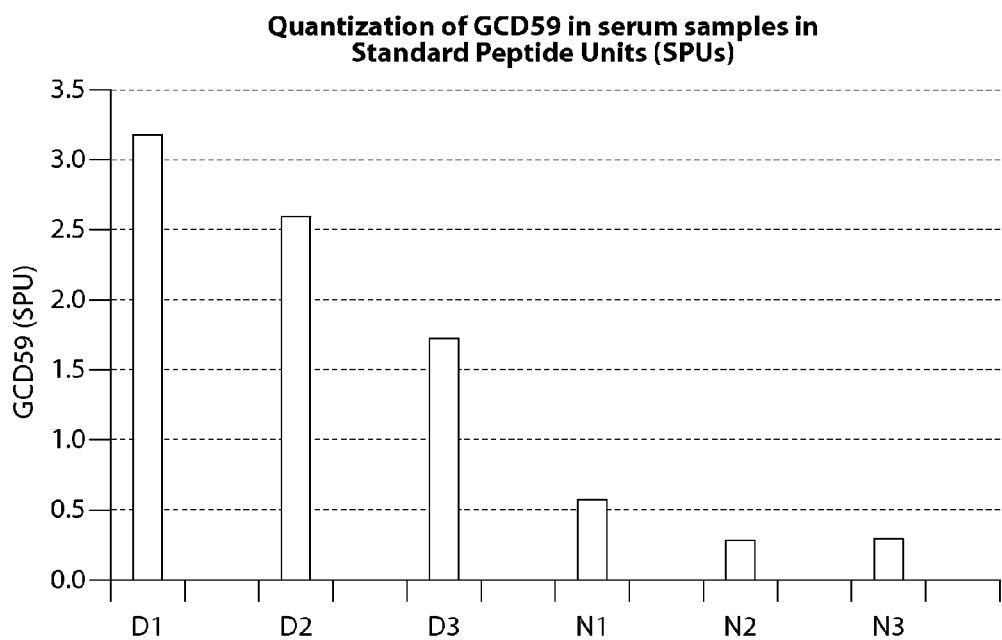

FIG. 23 illustrates the quantification of glycated hCD59 (GCD59) in human serum samples by employing a synthetic peptide (SP) standard (GCD59 Surrogate), which is a surrogate hybrid of GCD59, in SP units (SPUs). Shown in FIG. 23A is an optical density (OD) calibration curve with the SP (GCD59 Surrogate). FIG. 23B demonstrates the quantification, in SPU, of GCD59 in human serum samples.

FIG. 24 shows the HbA1c and serum glucose levels in non-diabetic (N1-N10) and diabetic (D1-D11) human subjects.

Figure 25:
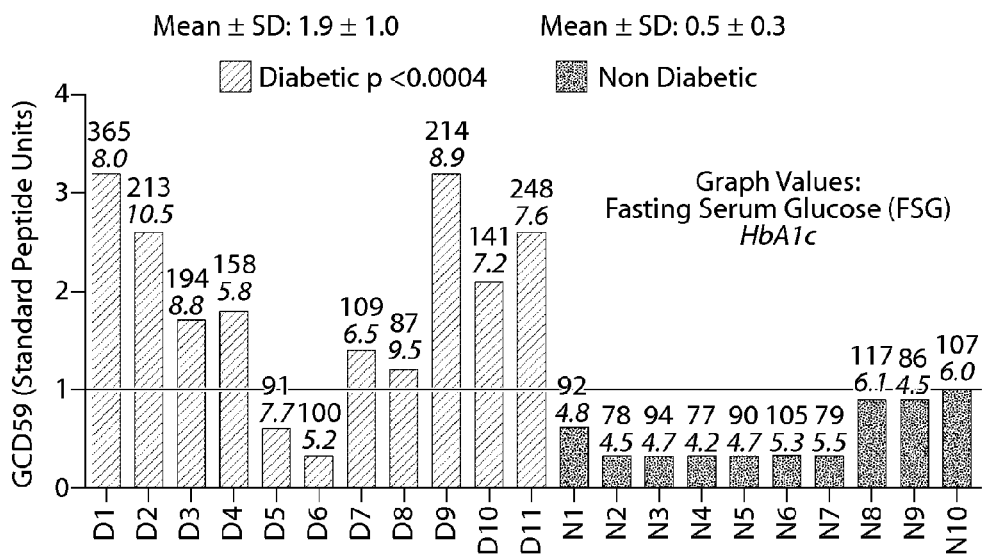

FIG. 25 depicts the diagnosis of and screening for human subjects with a diabetic condition using a surrogate of glycated and reduced hCD59 (GCD59 Surrogate) as a synthetic peptide standard. Diabetic (D1-D11) and non-diabetic (N1-N10) human subjects were tested. HbA1c and fasting serum glucose levels in these human subjects are also shown. The average coefficient of variation of the triplicate optical density (OD) values for all subjects is 3.5%.

FIG. 26 shows the ELISA results with an Amadori-modified CD59-derived peptide (AP). The structure of the AP is shown in FIG. 26A. Prior to the ELISA experiment, the AP was reduced with NaBH$_4$ in solution outside the plate, and the ELISA results are illustrated in FIG. 26B. Reduction of the AP with NaBH$_4$ was also carried out on the plate, and the ELISA results are shown in FIG. 26C. Regardless the reduction procedure, the rabbit anti-glucytollysine monoclonal antibody recognizes only the reduced AP and not the non-reduced AP. In both ELISA experiments, a glucitollysine-modified CD59-derived peptide (GP) was used as a control. The ELISA results indicate that the rabbit anti-glucytollysine monoclonal antibody also recognizes the GP (FIGS. 26B and 26C).

Figure 27:
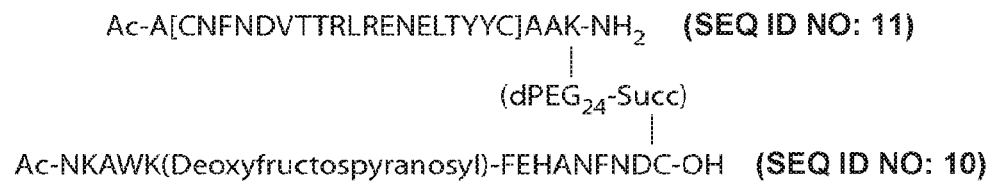

FIG. 27 depicts the structure of an Amadori peptide hybrid (Amadori CD59 surrogate).

Figure 28:
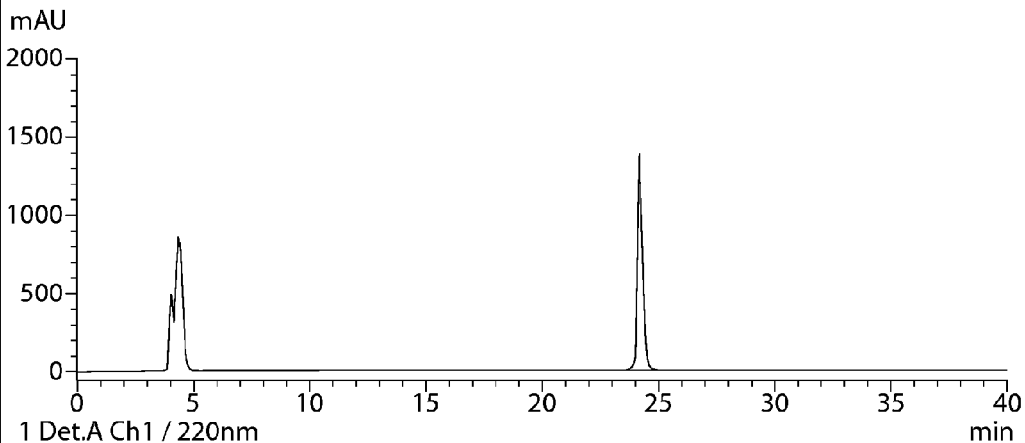

FIG. 28 is an analytical reverse-phase HPLC chromatogram of the Amadori peptide hybrid (Amadori CD59 surrogate).

Figure 29:
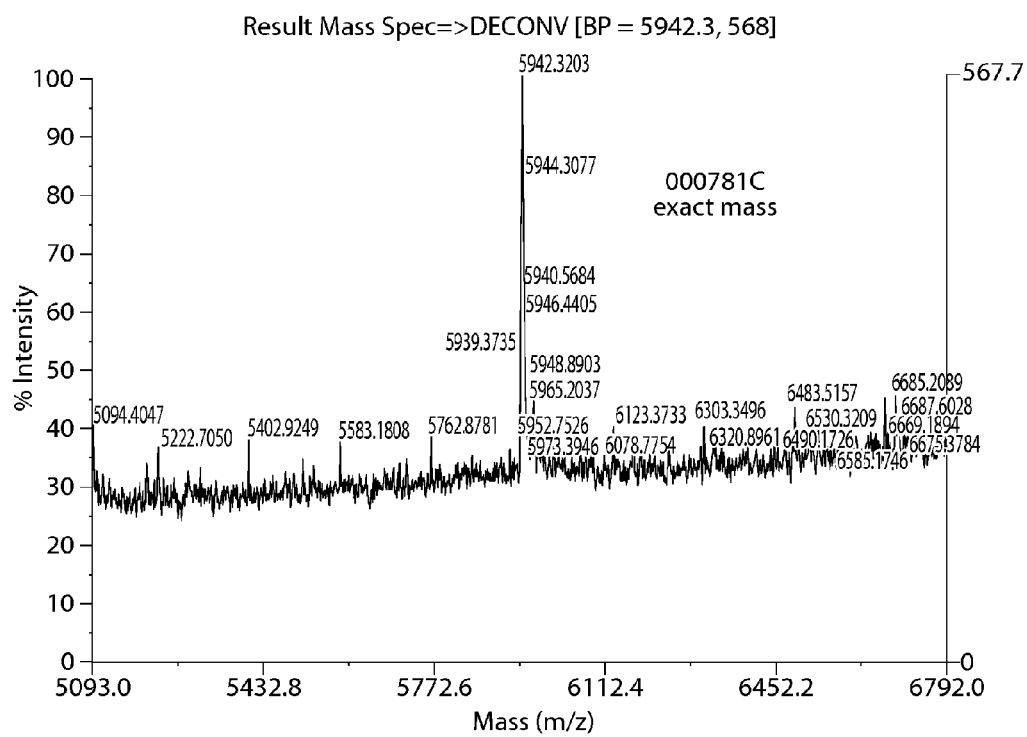

FIG. 29 illustrates a deconvoluted mass spectrum of the Amadori peptide hybrid (Amadori CD59 surrogate). The mass spectrum shows a base peak at about m/z 5942.3.

Figure 30:
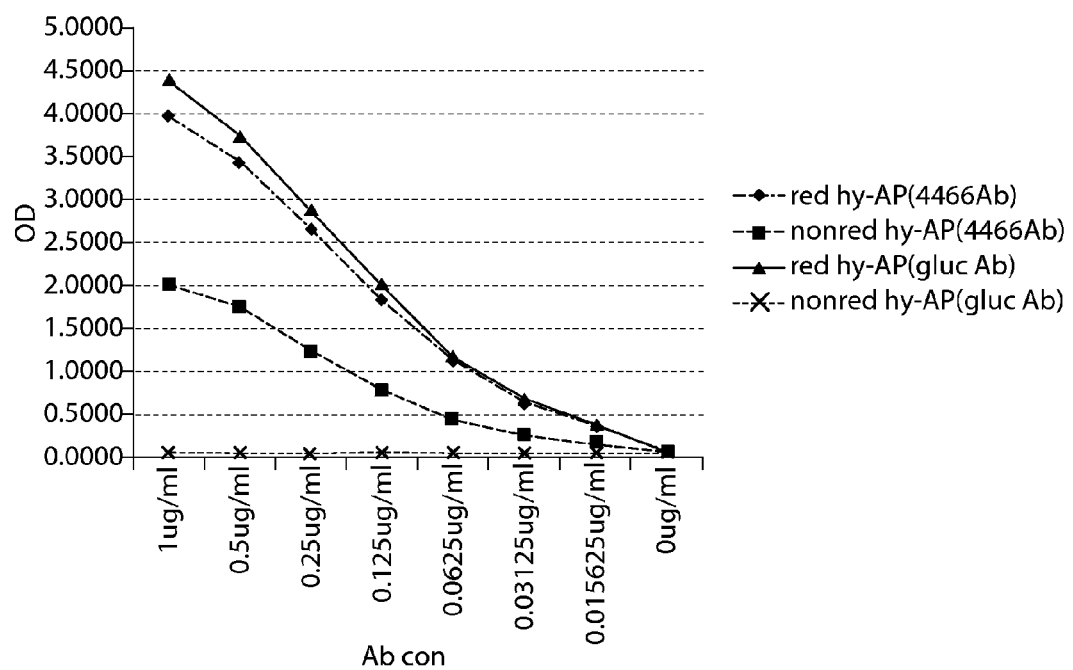

FIG. 30 shows the ELISA results with the Amadori hybrid peptide (Amadori CD59 surrogate, hy-AP, or nonred hy-AP). A reduced hy-AP (red hy-AP) was prepared by reducing a hy-AP using NaBH$_4$ prior to ELISA. The ELISA results show that the hy-AP, which is not reduced, and the reduced hy-AP are both recognized by 4466Ab, an anti-CD59 antibody. In contrast, the reduced hy-AP, and not the hy-AP, is recognized by the rabbit anti-glucytollysine mAb (gluc Ab).

DETAILED DESCRIPTION OF CERTAIN EMBODIMENTS OF THE INVENTION

In one aspect, the inventive compounds behave like a surrogate of a PTM protein by linking together distinct antigenic epitopes (at least one of which carries a post-translational modification) derived from a PTM protein. The linkers of the inventive surrogate compounds include segments that are not derived, or not solely derived, from amino acids. In preferred embodiments, the linkers of the inventive surrogate compounds are synthetic, flexible, and hydrophilic. In some aspects, the linkers of the inventive surrogate compounds comprise orthogonal functionalities, each of which is covalently bound to a distinct antigenic epitope (one of which carries the post-translational modification) derived from a single PTM protein.

The inventive surrogate compounds preserve the character of the antigenic epitopes and allow for recognition of each of the antigenic epitopes by antibodies directed to each epitope. Hence, the inventive surrogate compounds can replace an endogenous PTM protein during analysis of post-translational modifications or diseases comprising PTM proteins. For example, the inventive surrogate compounds can replace pure endogenous PTM protein in a sandwich ELISA and thereby serve as a convenient standard, calibrator, and/or reference compound to quantify the ELISA assay.

In certain embodiments, the inventive surrogate compound comprises an antigenic epitope that includes a post-translational modification ("PTM"), wherein the PTM is selected from the group consisting of a glycation; phosphorylation; lipoylation; citrullination (e.g., in rheumatoid arthritis); hypusination (e.g., in diabetic inflammation); transglutamination (e.g., in celiac disease); sumoylation (e.g., in cancer, neurodegenerative disease, and heart disease); acylation (e.g., O-acylation, N-acylation, S-acylation); acetylation; deacetylation; formylation; myristoylation; palmitoylation; alkylation; methylation; demethylation; isoprenylation (e.g., farnesylation, geranylation); lipidation; amidation (e.g., at the C-terminus); arginylation; polyglutamylation; polyglycylation; diphthamide; gamma-carboxylation; glycosylation; polysialylation; glypiation; hydroxylation; iodination; the covalent attachment of nucleotides; adenylation; ADP-ribosylation; flavin attachment; nitrosylation; oxidation; phosphopantetheinylation; pyroglutamate formation; sulfation; selenoylation; ISGylation; SUMOylation; ubiquitination; neddylation; deimination; deamidation; eliminylation; disulfide bridge formation; and racemization.

The inventive PTM protein surrogate compounds are particularly useful in diagnosing and following the progression of a disease for which PTM proteins are well associated. In certain embodiments, the disease is rheumatoid arthritis. In certain embodiments, the disease is celiac disease. In certain embodiments, the disease is cancer. In certain embodiments, the disease is neurodegenerative disease. In certain embodiments, the disease is heart disease. In certain embodiments, the disease is diabetic inflammation. In certain embodiments, the disease is diabetes or pre-diabetes. In further embodiments, as described more fully below, the invention provides a PTM protein surrogate compound is useful for the diagnosis of diabetes or pre-diabetes in a subject. In some embodiments, the surrogate compound is useful for monitoring the progression of diabetes or pre-diabetes in a subject. In certain embodiments, the compound comprises a post-translationally modified epitope of CD59. In still further embodiments, the post-translationally modified epitope of CD59 is a glycated epitope.

As used herein, "CD59" (also known as membrane inhibitor of reactive lysis [MIRL], protectin, HRF20 and H19), "human CD59," "hCD59," and "glycated CD59" are proteins having the amino acid sequence of Accession No. M95708 (Davies, A., et al., *Journal J. Exp. Med.* 170 (3), 637-654 (1989)). A nucleic acid sequence encoding CD59 also is provided by Davis, A, et al. The open reading frame encodes 128 amino acids, the full length precursor of CD59. The removal of a 25 amino acid hydrophobic signal sequence leads to the non-glycated of CD59 of 103 amino acid residues that is present in mature form in cells and tissues. Subsequent C-terminal cleavage of an hydrophobic sequence and concomitant attachment of a glycosylphosphatidylinositol (GPI) membrane anchor generates the mature 77 amino acid sequence of CD59 that undergoes additional posttranslational modifications such as N-glycosylation at N18 and glycation at K41. The soluble form of CD59 found in urine is derived from the membrane-bound CD59 following removal of the lipid part of the GPI anchor.

As used herein, the term "glycated" means that the glycating sugar is bound in either a linear or cyclic form. For example, the term "glycated CD59" means that the glycating sugar is bound to CD59 in either a linear or cyclic form, and includes the initial aldimine adduct known as the Schiff's base, the cyclized glycosylamine, tautomers of the initial Schiff's base, and the linear (keto) and cyclic (1-deoxy-fructopyranose) forms of the Amadori adduct. Compositions and methods regarding the glycated products of CD59 and peptide fragments thereof are disclosed in U.S. Pat. No. 6,835,545; U.S. Pat. No. 7,049,082; and U.S. Pat. No. 7,439,330; the entire contents of which are incorporated herein by reference. In certain preferred embodiments glycated products can include the linear and reduced $N^\epsilon$-(1-deoxy-D-glucitol-1-yl) L-lysine (glucitollysine moiety).

In other embodiments, the disease being diagnosed or followed is autoimmune disease. Non-limiting examples of autoimmune diseases include multiple sclerosis, rheumatoid arthritis, systemic lupus erythematosus, primary bilary cirrhosis, celiac disease, Crohn's disease, and other diseases associated with the presence of abberent PTM proteins. In certain embodiments, the invention provides PTM protein surrogate compound useful for the analysis or diagnosis of multiple sclerosis in a subject, wherein the compound comprises a post-translationally modified epitope of myelin basic protein (MBP) (Kim J. K., et al., Multiple Sclerosis An Important Role for Post-Translational Modifications of Myelin Basic Protein in Pathogenesis *Mol Cell Proteomics,* 2003 July; 2(7): 453-462). In certain embodiments, MBP is methylated. In further embodiments, the epitope of MBP is deiminated. In further embodiments, the epitope of MBP is phosphorylated. In certain embodiments, the invention provides PTM protein surrogate compound useful for the analysis or diagnosis of rheumatoid arthritis in a subject, wherein the compound comprises a post-translationally modified epitope of antithrombin (Ordonez A., et al., Increased levels of citrullinated antithrombin in plasma of patients with rheumatoid arthritis and colorectal adenocarcinoma determined by a newly developed ELISA using a specific monoclonal antibody *Thromb. Haemost.* 2010 Sep. 13; 104(6)). In certain embodiments, the epitope of antithrombin is citrullinated. In certain embodiments, the invention provides PTM protein surrogate compound useful for the analysis or diagnosis of systemic lupus erythematosus in a subject, wherein the compound comprises a post-translationally modified epitope of a protein selected from the group consisting of ERK1/2, SAPK/JNK, p38 MAPK, and AKT (Nakao M, et al., Gene network analysis of bone marrow mononuclear cells reveals activation of multiple kinase pathways in human systemic lupus erythematosus *PLoS One* 2010 Oct. 14; 5(10): e13351). In certain embodiments, the epitope form of ERK1/2, SAPK/JNK, p38 MAPK, or AKT is phosphorylated.

In further embodiments, the inventive surrogate compound comprises an antigenic epitope that carries a post-translational modification, PTM, wherein the PTM results from the glycation of an amino function of an amino acid residue. In still further embodiments, the PTM results from the glycation of an ε-amino function in a lysine residue. The process of glycation is a non-enzymatic addition of glucose to specific glycation sites in proteins. The non-enzymatic reaction between glucose and the free amino groups of proteins, such as the amino side chain of lysine, forms glycated, glycosylamine, and glycated Amadori adducts. Glycation has been found to modify, for example, hemoglobin and CD59. Similar glycation reactions have also been found to occur with a variety of other proteins such as lens crystallin, collagen, and nerve proteins (Bunn et al., *Biochem. Biophys. Res. Commun.* 67:103-109, 1975; Koenig et al., *J. Biol. Chem.* 252:2992-2997, 1975; Monnier and Cerami, *Maillard Reaction in Food and Nutrition*, Ed. Waller, G. A., American Chemical Society, 431-448, 1983; and Monnier and Cerami, *Clinics in Endocrinology and Metabolism* 11:431-452, 1982).

In still further embodiments, the inventive surrogate compounds comprise an antigenic epitope that carries a post-translational modification, PTM, wherein the PTM is a glycation reaction that contributes to an advanced glycation endproduct (AGE). AGEs are a hallmark of diabetic disease. AGEs develop over time as initially glycated, glycosylamine, or glycated Amadori adducts undergo secondary reactions such as oxidation, rearrangement, dehydration, or cross-linking with other protein groups, and finally accumulate as a family of complex structures referred to as AGEs. Substantial progress has been made towards the elucidation of the biological roles and clinical significance of AGEs so that it is now acknowledged that many of the conditions heretofore attributed to the aging process or to the pathological effects of diseases such as diabetes are attributable at least in part to the formation, accumulation, and/or activity of AGEs in vivo.

As discussed, glycation has been shown to modify human CD59. Glycation of human CD59, including, but not limited to, K41 glycation of human CD59, is correlated to abnormal blood sugar levels, and glycation of CD59 has been shown to interfere with the normal activity of CD59. Human CD59 functions normally by binding to the terminal components of the membrane attack complex of complement (MAC), thereby interfering with membrane insertion and polymerization of the C9 component of complement. Glycation at K41 of CD59 interferes with CD59's ability to prevent the assembly of the MAC. While not wishing to be bound by any theory, it is believed that, as a result of glycation of CD59, the MAC is permitted to form more readily which leads to the development of proliferative chronic diabetic complications. Indeed, the membrane attack complex has been shown to stimulate proliferation of fibroblasts, smooth muscle, mesangial and other cells, in part by releasing growth factors such as FGF and PDGF from MAC-targeted endothelium. The MAC also induces increased synthesis of extracellular matrix proteins by mesangial cells. Thus, increased MAC deposition in diabetic tissues is believed to induce growth factor release from endothelium, which stimulates cell proliferation in the vascular wall and contributes to the expansion of the extracellular matrix and to the glomerulosclerosis that characterizes diabetic nephropathy. Glycation of human CD59 is believed to be involved in the pathogenesis of the vascular complications of pre-diabetes and diabetes. Accordingly, the clinical evaluation of glycated, glycosylamine, or glycated Amadori adducts of CD59 is a more direct indication of the vascular complications of pre-diabetes and diabetes.

Normally, CD59 limits activation and restricts deposition of the membrane attack complex of complement (MAC) in blood vessels and the kidneys. Thus, glycation of CD59 disrupts its regulatory function and effectively enables the unregulated activation of complement and excessive and accelerated deposition of MAC. Reports of increased deposition of the membrane attack complex of complement (MAC) in blood vessels and kidneys of diabetic patients suggest that there may be a link between complement activation and the development of diabetic complications (Weiss, J. S., et al. (1990) *Cornea* 9, 131-138; Falk, R. J., et al. (1987) *Am. J. Kidney Dis.* 9, 121-128). Indeed, the MAC stimulates proliferation of fibroblasts and smooth muscle, mesangial, and other cells, in part by releasing growth factors such as basic fibroblast growth factor and platelet-derived growth factor from MAC-targeted endothelium (Benzaquen, L. R., et al. (1994) *J. Exp. Med.* 179, 985-992). The MAC also induces increased synthesis of extracellular matrix proteins by mesangial cells (Wagner, C., et al. (1994) *Exp. Nephrol.* 2, 51-56). Thus, glycation of CD59 may increase MAC deposition in diabetic tissues which may induce the release of growth factors that would stimulate cell proliferation in the vascular wall and contribute to the development of vascular proliferative disease. Glycated CD59 has been found in human urine, indicating that CD59 is glycated in vivo (Acosta, J., et al. (2000) *PNAS* 97, 5450-5455).

Certain aspects of the invention relate to compositions and methods of preparing and using surrogate compounds comprising lysine-41-glycated products of human CD59 and fragments thereof. According to the NMR structure of human CD59, lysine-41 (K41) appears particularly susceptible to glycation because of its proximity to histidine, histidine-44 (H44), in the protein (Fletcher, C. M., et al. (1994) *Structure* 2, 185-199) and forms a glyction motif. Furthermore, the fact that K41 is adjacent to tryptophan-40 (W40), a conserved amino acid that is essential for CD59 function, suggests that glycation of K41 may hinder the activity of CD59 (Bodian, D. L., et al. (1997) *J. Exp. Med.* 185, 507-516; Yu, J., et al. (1997) *J. Exp. Med.* 185, 745-753). Replacement by site-directed mutagenesis of either K41 or H44 abolishes the sensitivity of human CD59 to glycation-mediated inactivation.

In one aspect, the invention provides two antigenic epitopes derived from glycated human CD59 which are recognized by two distinct and specific monoclonal antibodies. In certain embodiments, the two antigens, representing a C-terminal epitope and the glycated epitope of glycated human CD59, are linked through a hetero-bifunctional polyethylene glycol linker to generate a surrogate compound of glycated CD59. This surrogate compound was captured on an ELISA plate coated with a mouse mAb targeting the C-terminal antigen and detected by the rabbit mAb targeting the glycated epitope. HRP-labeled polyclonal goat-anti-rabbit Ab was used to quantify the amount of glycated CD59 surrogate attached to the plate. The quantification was linear, sensitive, highly reproducible, and provided the means to quantify the levels of glycated CD59 in the serum obtained from normal individuals and from subjects presenting different stages of diabetes.

Compounds

Compounds of the present invention include surrogates of post-translationally modified proteins. Compounds of this invention and salts thereof include those, as set forth above and described herein, and are illustrated in part by the various classes, subclasses, subgenera, and species disclosed herein. In certain embodiments, the compound is water-soluble.

The inventive compounds may be useful in diagnosing a condition or disease, or monitoring the regression, progression, or onset of a condition or disease (e.g., monitoring the efficacy of a therapeutic treatment) in a subject. Exemplary conditions or diseases include, but are not limited to, multiple sclerosis, lupus erythematosus (e.g., systemic lupus erythematosus), primary bilary cirrhosis, celiac disease, Crohn's disease, rheumatoid arthritis, cancer, neurodegenerative disease, heart disease, diabetic inflammation, diabetes, pre-diabetes, autoimmune diseases, inflammatory diseases, rheumatoid arthritis, and other diseases associated with the presence of abberent PTM proteins. In certain embodiments, the compounds are useful in diagnosing or following the progression of multiple sclerosis in a subject and complications thereof. In certain embodiments, the compounds are useful in diagnosing or following the progression of systemic lupus in a subject and complications thereof. In certain embodiments, the compounds are useful in diagnosing or following the progression of lupus erythematosus in a subject and complications thereof. In certain embodiments, the compounds are useful in diagnosing or following the progression of primary bilary cirrhosis in a subject and complications thereof. In certain embodiments, the compounds are useful in diagnosing or following the progression of celiac disease in a subject and complications thereof. In certain embodiments, the compounds are useful in diagnosing or following the progression of Crohn's disease in a subject and complications thereof. In certain embodiments, the compounds are useful in diagnosing or following the progression of rheumatoid arthritis in a subject and complications thereof. In certain embodiments, the compounds are useful in diagnosing or following the progression of cancer in a subject and complications thereof. In certain embodiments, the compounds are useful in diagnosing or following the progression of neurodegenerative disease in a subject and complications thereof. In certain embodiments, the compounds are useful in diagnosing or following the progression of heart disease in a subject and complications thereof. In certain embodiments, the compounds are useful in diagnosing or following the progression of diabetic inflammation in a subject and complications thereof. In certain embodiments, the compounds are useful in diagnosing or following the progression of diabetes in a subject and complications thereof. In certain embodiments, the compounds are useful in diagnosing or following the progression of a pre-diabetic subject. In certain embodiments, the compounds are useful in diagnosing or following the progression of multiple sclerosis. In other embodiments, the compounds are useful in diagnosing or following the progression of autoimmune diseases or inflammatory diseases. In certain embodiments, compounds are useful in diagnosing or following the progression of autoimmune diseases. In other embodiments, the compounds are useful in diagnosing rheumatoid arthritis. In other embodiments, the compounds are useful in diagnosing or following the progression of systemic lupus erythematosus. In other embodiments, the compounds are useful in diagnosing primary bilary cirrhosis. In other embodiments, the compounds are useful in diagnosing or following the progression of celiac disease. In other embodiments, the compounds are useful in diagnosing or following the progression of Crohn's disease. In other embodiments, the compounds are useful in diagnosing or following the progression of other diseases associated with the presence of abberent PTM proteins.

Thus, in one aspect, the present invention provides a compound comprising two or more antigenic epitopes of a native protein joined by one or more linkers wherein:

each epitope is, independently, 1-100 amino acids in length;

at least one epitope comprises a post-translational modification;

each of the compounds optionally comprises a label, wherein the label is a fluorogenic, phosphoregenic, chemiluminogenic, chromogenic, affinity-based, or radioactive;

each of the linkers is independently selected from the group consisting of cyclic or acyclic, substituted or unsubstituted, branched or unbranched aliphatic moiety; or a cyclic or acyclic, substituted or unsubstituted, branched or unbranched heteroaliphatic moiety; substituted or unsubstituted, branched or unbranched acyl; substituted or unsubstituted, branched or unbranched aryl; substituted or unsubstituted, branched or unbranched heteroaryl; wherein each substituent is independently selected from the group consisting of branched and unbranched alkyl, branched and unbranched alkenyl, branched and unbranched alkynyl, heterocyclic, —$OR^A$; —$C(=O)R^A$; —$CO_2R^A$; —$SR^A$; —$SOR^A$; —$SO_2R^A$; =O; =N($R^A$); =S; —N($R^A$)$_2$; —NHC(=O)$R^A$; —$NR^AC(=O)N(R^A)_2$; —OC(=O)O$R^A$; —OC(=O)$R^A$; —OC(=O)N($R^A$)$_2$; or —$NR^AC(=O)OR^A$; wherein each occurrence of $R^A$ is independently a hydrogen, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In certain embodiments, the compound comprises a label. In further embodiments, the compound does not comprise a label. In still further embodiments, the linker is, independently, a cyclic or acyclic, substituted or unsubstituted, branched or unbranched heteroaliphatic moiety. In further embodiments, the linker is 1 to 500 atoms in length. In still further embodiments, the linker comprises a polymeric region. In certain embodiments, the polymeric region comprises 1-100 monomers. In further embodiments, the polymeric region comprises 10-60 monomers. In still further embodiments, the polymeric region comprises 20-40 monomers. In certain embodiments, the polymeric region comprises ethylene glycol monomers. In further embodiments, the polymeric region comprises propylene glycol monomers. In still further embodiments, the linker is not charged.

In one embodiment each linker is, independently, of the formula:

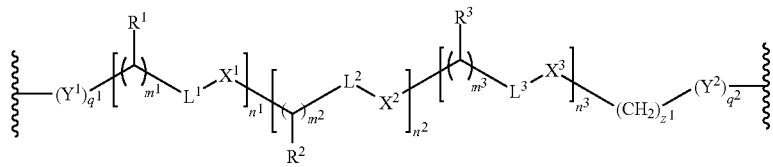

wherein each $R^1$, $R^2$, and $R^3$ is, independently, hydrogen; cyclic or acyclic, substituted or unsubstituted, branched or unbranched aliphatic moiety; or a cyclic or acyclic, substituted or unsubstituted, branched or unbranched heteroaliphatic moiety; substituted or unsubstituted, branched or unbranched acyl; substituted or unsubstituted, branched or unbranched aryl; substituted or unsubstituted, branched or unbranched heteroaryl; wherein each substituent is independently selected from the group consisting of a halogen; branched and unbranched alkyl; branched and unbranched alkenyl; branched and unbranched alkynyl; heterocyclic; —$OR^A$; —$C(=O)R^A$; —$CO_2R^A$; —$SR^A$; —$SOR^A$; —$SO_2R^A$; =O; =$N(R^A)$; =S; —$N(R^A)_2$; —$NHC(=O)R^A$; —$NR^AC(=O)N(R^A)_2$; —$OC(=O)OR^A$; —$OC(=O)R^A$; —$OC(=O)N(R^A)_2$; or —$NR^AC(=O)OR^A$; wherein each occurrence of $R^A$ is independently a hydrogen; a label; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or a heteroarylthio moiety;

each $R^4$, $R^5$, $R^6$, $R^7$, $R^8$, and $R^9$ is, independently, a substituted or unsubstituted, branched or unbranched, cyclic or acyclic $C_{1-10}$ alkyl; a substituted or unsubstituted, branched or unbranched, cyclic or acyclic $C_{1-10}$ haloalkyl; a substituted or unsubstituted aryl; or a substituted or unsubstituted haloaryl;

each $L^1$, $L^2$, and $L^3$ is, independently, cyclic or acyclic, substituted or unsubstituted, branched or unbranched aliphatic moiety; or a cyclic or acyclic, substituted or unsubstituted, branched or unbranched heteroaliphatic moiety; substituted or unsubstituted, branched or unbranched arylene; substituted or unsubstituted, branched or unbranched heteroarylene; wherein each substituent is independently selected from the group consisting of a halogen; branched and unbranched alkyl; branched and unbranched alkenyl; branched and unbranched alkynyl; heterocyclic; —$OR^B$; —$C(=O)R^B$; —$CO_2R^B$; —$SR^B$; —$SOR^B$; —$SO_2R^B$; =O; =$N(R^B)$; =S; —$N(R^B)_2$; —$NHC(=O)R^B$; —$NR^BC(=O)N(R^B)_2$; —$OC(=O)OR^B$; —$OC(=O)R^B$; —$OC(=O)N(R^B)_2$; or —$NR^BC(=O)OR^B$; wherein each occurrence of $R^B$ is independently a hydrogen; a label; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or a heteroarylthio moiety;

each $X^1$, $X^2$, $X^3$, $X^4$, $X^5$, and $X^6$ is, independently, —O—, —S—, —$N(R^4)$—, or —$N(R^4)_2$—;

each $m^1$, $m^2$, and $m^3$ is, independently, 0 or an integer between 1 and 10, inclusive;

each $n^1$, $n^2$, and $n^3$ is, independently, 0 or an integer between 1 and 100, inclusive;

each $q^1$ and $q^2$ is, independently, 0 or 1;

$z^1$ is 0 or an integer between 1 and 10, inclusive;

each $Y^1$ and $Y^2$ is selected from the group consisting of:

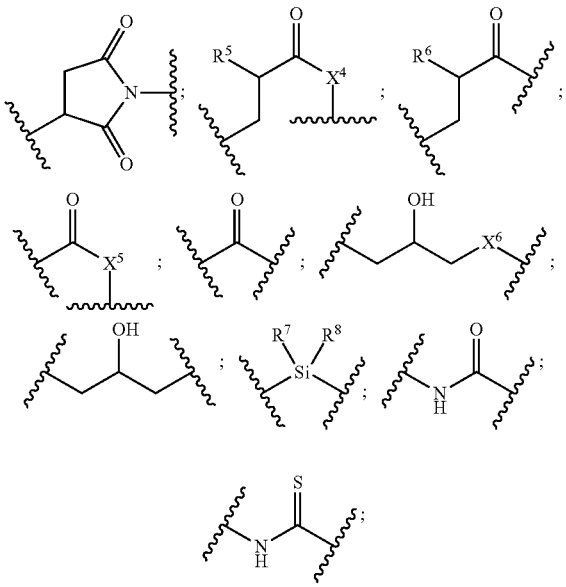

—$NR^9$—; —S—; and —O—.

In further embodiments, each $L^1$, $L^2$, and $L^3$ is, independently, —$CH_2$—; —$CH(R^C)$—; —$C(=O)$—; —$OC(=O)$—; —$N(R^C)C(=O)$—; —SO—; —$OS(=O)$—; $N(R^C)S(=O)$—; —$S(=O)_2$—; —$OS(=O)_2$—; —$N(R^C)S(=O)_2$—; —$C(=O)$—; —$OC(=O)$—; —$N(R^C)C(=O)$—; —$C(=NR^C)$—; —$C(=S)$—; —$N(R^C)C(=S)$—; wherein each occurrence of $R^C$ is independently a hydrogen; a label; an aliphatic moiety; a heteroaliphatic moiety; an acyl moiety; an aryl moiety; or a heteroaryl moiety.

In still further embodiments, each $L^2$ can join with $X^1$ and $X^2$ and, independently, each $L^3$ can join with $X^2$ and $X^3$ to form a moiety selected from the group consisting of a label; —$OR^DO$—; —$OR^DS$—; —$OR^DN(R^4)$—; —$OR^DN(R^4)_2$—; —$SR^DO$—; —$SR^DS$—; —$SR^DN(R^4)$—; —$SR^DN(R^4)_2$—; —$N(R^4)R^DO$—; —$N(R^4)R^DS$—; —$N(R^4)R^DN(R^4)$—; —$N(R^4)R^DN(R^4)_2$—; —$N(R^4)_2R^DO$—; —$N(R^4)_2R^DS$—; —$N(R^4)_2R^DN(R^4)$—; or —$N(R^4)_2R^DN(R^4)_2$—; wherein each occurrence of $R^D$ is independently a substituted or unsubstituted, branched or unbranched alkylene; substituted or unsubstituted, branched or unbranched cycloalkylene; a substituted or unsubstituted, branched or unbranched alkenylene; substituted or unsubstituted, branched or unbranched cycloalkenylene; a substituted or unsubstituted, branched or unbranched arylene; or substituted or unsubstituted, branched or unbranched heteroarylene.

In certain embodiments, $Y^1$ or $Y^2$ is

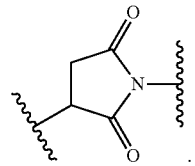 [SMILES: *C1CC(=O)N(*)C1=O]

In further embodiments, $Y^1$ or $Y^2$ is

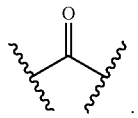

In still further embodiments, $Y^1$ is

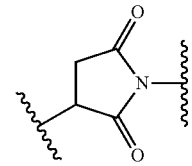 [SMILES: *C1CC(=O)N(*)C1=O]

and $Y^2$ is

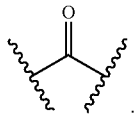

In certain embodiments, the linker comprises

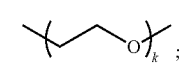

wherein k is an integer between 1 and 100, inclusive. In further embodiments, the linker comprises

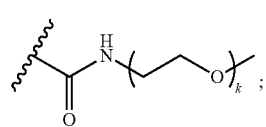

wherein k is an integer between 1 and 100, inclusive. In still further embodiments, the linker comprises

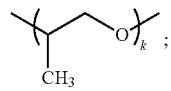

wherein k is an integer between 1 and 100, inclusive. In certain embodiments, the linker comprises

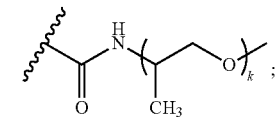

and wherein k is an integer between 1 and 100, inclusive.

In still further embodiments, the linker is of the formula:

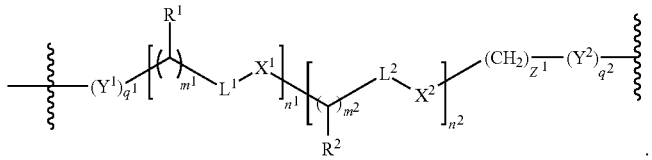

In further embodiments, the linker is of the formula:

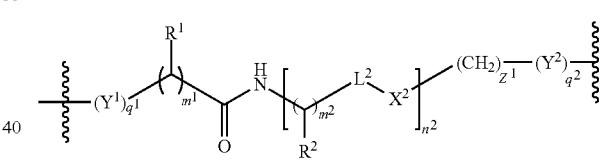

In still further embodiments, the linker is of the formula:

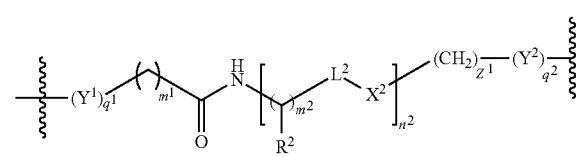

In further embodiments, the linker is of the formula:

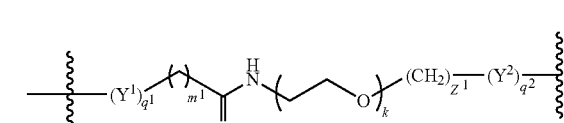

wherein k is 0 or an integer from 1 to 100, inclusive.

In still further embodiments, the linker is of the formula:

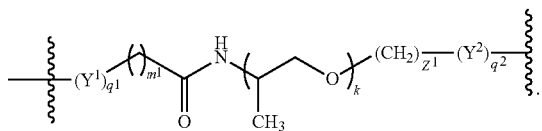

wherein k is 0 or an integer from 1 to 100, inclusive.

In further embodiments, the linker is of the formula:

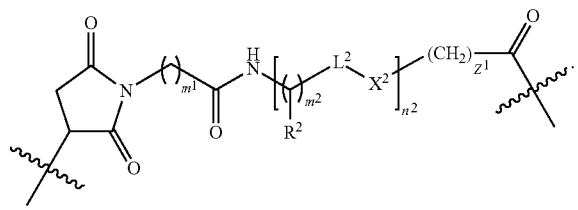

In still further embodiments, the linker is of the formula:

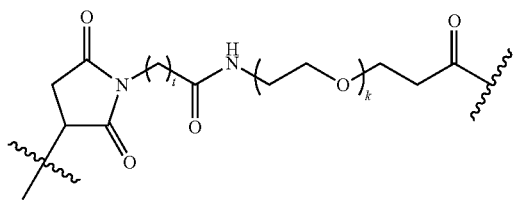

wherein
 t is an integer from 1 to 12, inclusive, and
 k is 0 or an integer from 1 to 100, inclusive.

In further embodiments, the linker is of the formula:

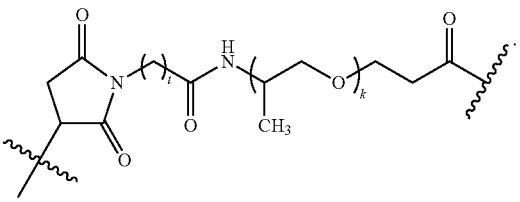

wherein
 t is an integer from 1 to 12, inclusive, and
 k is 0 or an integer from 1 to 100, inclusive.

In still further embodiments, the linker is the formula:

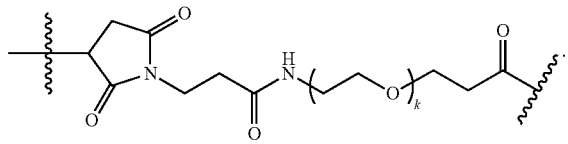

wherein k is 0 or an integer from 1 to 100, inclusive.

In further embodiments, the linker is the formula:

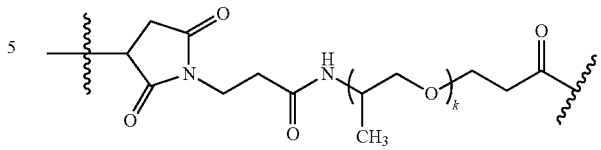

wherein k is 0 or an integer from 1 to 100, inclusive.

In still further embodiments, the linker is the formula:

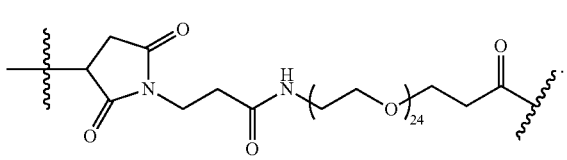

In further embodiments, the linker is the formula:

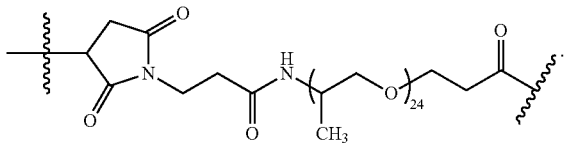

In still further embodiments, the linker is covalently bound to each antigenic epitope, independently, at either the C-terminus, N-terminus, or a side chain of an amino acid or an amino acid derivative of each antigenic epitope. In certain embodiments, the linker is bound to the N-terminus of an epitope. In further embodiments, the linker is bound to the C-terminus of an epitope.

In certain embodiments, the linker is covalently bound to the C-terminus of an antigenic epitope. In further embodiments, the linker is covalently bound to the N-terminus of an antigenic epitope. In still further embodiments, the linker is covalently bound to a side chain of an amino acid of an antigenic epitope. In certain embodiments, the linker is covalently bound to a side chain of an amino acid of all the antigenic epitopes. In further embodiments, the amino acid attached to the linker is independently selected from the group consisting of cysteine, lysine, serine, threonine, tyrosine, histidine, arginine, tryptophan, asparagine, glutamine, aspartic acid, and glutamic acid. In certain embodiments, the amino acid attached to the linker is cysteine. In further embodiments, the amino acid attached to the linker is lysine. In still further embodiments, the amino acid attached to the linker of one epitope is lysine, and the amino acid of another epitope is cysteine. In certain embodiments, the amino acid derivative is independently selected from the group consisting of selenocysteine, 3-hydroxyproline, 3-hydroxyproline, carnitine, γ-aminobutyric acid (GABA), or L-3,4-dihydroxyphenylalanine (L-DOPA).

In certain embodiments, the present invention provides compounds prepared from a precursor of the linker of the formula:

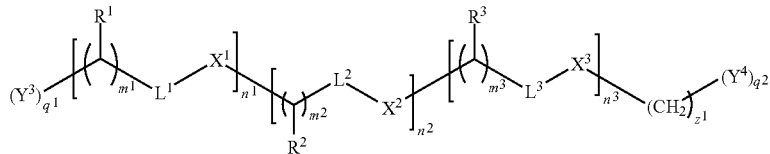

wherein each $R^1$, $R^2$, and $R^3$ is, independently, hydrogen; a label; cyclic or acyclic, substituted or unsubstituted, branched or unbranched aliphatic moiety; or a cyclic or acyclic, substituted or unsubstituted, branched or unbranched heteroaliphatic moiety; substituted or unsubstituted, branched or unbranched acyl; substituted or unsubstituted, branched or unbranched aryl; substituted or unsubstituted, branched or unbranched heteroaryl; wherein each substituent is independently selected from the group consisting of a halogen; branched and unbranched alkyl, branched and unbranched alkenyl, branched and unbranched alkynyl, heterocyclic, $-OR^A$; $-C(=O)R^A$; $-CO_2R^A$; $-SR^A$; $-SOR^A$; $-SO_2R^A$; $=O$; $=N(R^A)$; $=S$; $-N(R^A)_2$; $-NHC(=O)R^A$; $-NR^AC(=O)N(R^A)_2$; $-OC(=O)OR^A$; $-OC(=O)R^A$; $-OC(=O)N(R^A)_2$; or $-NR^AC(=O)OR^A$; wherein each occurrence of $R^A$ is independently a hydrogen; a label; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or a heteroarylthio moiety;

$R^4$ is a substituted or unsubstituted, branched or unbranched, cyclic or acyclic $C_{1\text{-}20}$ alkyl, or a substituted or unsubstituted aryl;

each $L^1$, $L^2$, and $L^3$ is, independently, cyclic or acyclic, substituted or unsubstituted, branched or unbranched aliphatic moiety; or a cyclic or acyclic, substituted or unsubstituted, branched or unbranched heteroaliphatic moiety; substituted or unsubstituted, branched or unbranched arylene; substituted or unsubstituted, branched or unbranched heteroarylene; wherein each substituent is independently selected from the group consisting of branched and unbranched alkyl, branched and unbranched alkenyl, branched and unbranched alkynyl, heterocyclic, $-OR^B$; $-C(=O)R^B$; $-CO_2R^B$; $-SR^B$; $-SOR^B$; $-SO_2R^B$; $=O$; $=N(R^B)$; $=S$; $-N(R^B)_2$; $-NHC(=O)R^B$; $-NR^BC(=O)N(R^B)_2$; $-OC(=O)OR^B$; $-OC(=O)R^B$; $-OC(=O)N(R^B)_2$; or $-NR^BC(=O)OR^B$; wherein each occurrence of $R^B$ is independently a hydrogen; a label; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or a heteroarylthio moiety;

each $X^1$, $X^2$, $X^3$, $X^4$, $X^5$, and $X^6$ is, independently, $-O-$, $-S-$, $-N(R^4)-$, or $-N(R^4)_2-$;

each $m^1$, $m^2$, and $m^3$ is, independently, 0 or an integer between 1 and 10, inclusive;

each $n^1$, $n^2$, and $n^3$ is, independently, 0 or an integer between 1 and 100, inclusive;

each $q^1$ and $q^2$ is, independently, 0 or 1;

$z^1$ is 0 or an integer between 1 and 10, inclusive; and each $Y^1$ and $Y^2$ is, independently, an electrophilic reactive group or a nucleophilic reactive group.

In certain embodiments, each $L^1$, $L^2$, and $L^3$ is, independently, $-CH_2-$; $-CH(R^C)-$; $-C(=O)-$; $-OC(=O)-$; $-N(R^C)C(=O)-$; $-SO-$; $-OS(=O)-$; $N(R^C)S(=O)-$; $-S(=O)_2-$; $-OS(=O)_2-$; $-N(R^C)S(=O)_2-$; $-C(=O)-$; $-OC(=O)-$; $-N(R^C)C(=O)-$; $-C(=NR^C)-$; $-C(=S)-$; $-N(R^C)C(=S)-$; wherein each occurrence of $R^C$ is independently a hydrogen; a label; an aliphatic moiety; a heteroaliphatic moiety; an acyl moiety; an aryl moiety; or a heteroaryl moiety.

In further embodiments, each $L^2$ can join with $X^1$ and $X^2$ and, independently, each $L^3$ can join with $X^2$ and $X^3$ to form a moiety selected from the group consisting of a label; $-OR^DO-$; $-OR^DS-$; $-OR^DN(R^4)-$; $-OR^DN(R^4)_2-$; $-SR^DO-$; $-SR^DS-$; $-SR^DN(R^4)-$; $-SR^DN(R^4)_2-$; $-N(R^4)R^DO-$; $-N(R^4)R^DS-$; $-N(R^4)R^DN(R^4)-$; $-N(R^4)R^DN(R^4)_2-$; $-N(R^4)_2R^DO-$; $-N(R^4)_2R^DS-$; $-N(R^4)_2R^DN(R^4)-$; or $-N(R^4)_2R^DN(R^4)_2-$; wherein each occurrence of $R^D$ is independently a substituted or unsubstituted, branched or unbranched alkylene; substituted or unsubstituted, branched or unbranched cycloalkylene; a substituted or unsubstituted, branched or unbranched alkenylene; substituted or unsubstituted, branched or unbranched cycloalkenylene; a substituted or unsubstituted, branched or unbranched arylene; or substituted or unsubstituted, branched or unbranched heteroarylene.

In certain embodiments, $Y^1$ and $Y^2$ are both electrophilic reactive groups. In further embodiments, $Y^1$ and $Y^2$ are both nucleophilic reactive groups. In still further embodiments, $Y^1$ is an electrophilic reactive group and $Y^2$ is a nucleophilic reactive group. In certain embodiments, $Y^1$ is a nucleophilic reactive group, and $Y^2$ is an electrophilic reactive group. In further embodiments, each electrophilic reactive group is, independently,

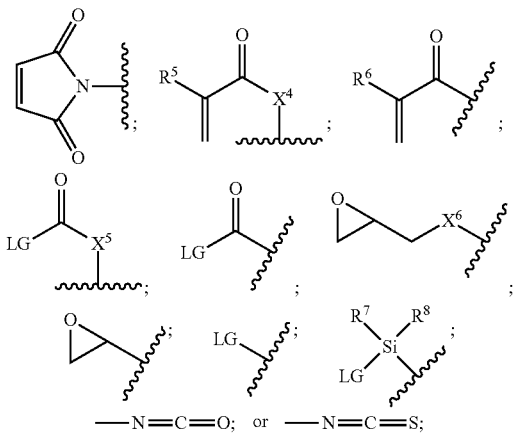

wherein each LG is a leaving group independently selected from the group consisting of a halo; $OR^9$; $SR^{10}$; $O(CO)R^{11}$; $S(CO)R^{12}$; and $O(SO_2)R^{13}$;

wherein each $R^5$, $R^6$, $R^7$, $R^8$, $R^9$, $R^{10}$, $R^{11}$, $R^{12}$, and $R^{13}$ is, independently, hydrogen, a substituted or unsubstituted, branched or unbranched, cyclic or acyclic $C_{1\text{-}10}$ alkyl; a substituted or unsubstituted, branched or unbranched, cyclic or acyclic $C_{1-10}$ haloalkyl; a substituted or unsubstituted aryl; or a substituted or unsubstituted haloaryl.

In certain embodiments, each LG is, independently, a chloro; bromo; iodo;

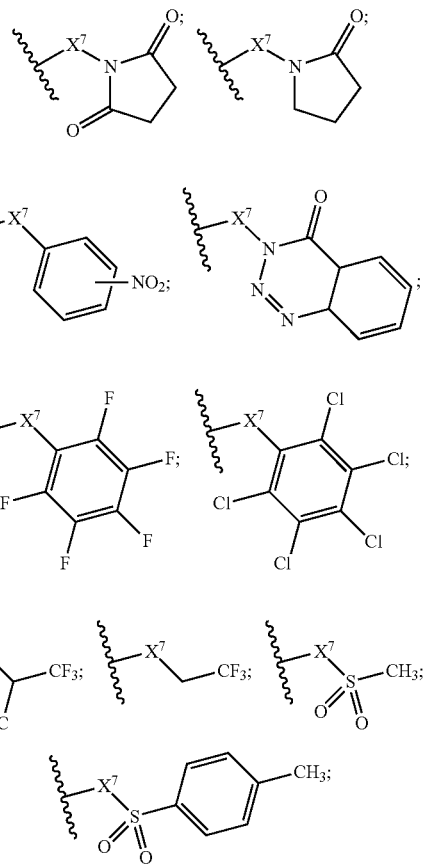

wherein each $X^7$ is, independently, O or S.

In still further embodiments, $Y^1$ or $Y^2$ is

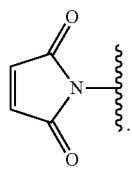

In certain embodiments, $Y^1$ or $Y^2$ is

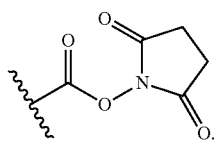 [SMILES: *C(=O)ON1C(=O)CCC1=O]

In further embodiments, $Y^1$ is

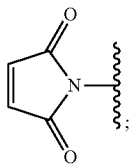 [SMILES: *N1C(=O)C=CC1=O]

and $Y^2$ is

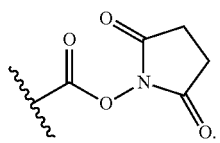 [SMILES: *C(=O)ON1C(=O)CCC1=O]

In still further embodiments, each nucleophilic reactive group is, independently, —$NHR^6$; —SH; or —OH.

In certain embodiments, the compound comprises one epitope comprising a post-translational modification. In further embodiments, the post-translational modification is selected from the group consisting of glycation; phosphorylation; lipoylation; citrullination (e.g., in rheumatoid arthritis); hypusination (e.g., in diabetic inflammation); transglutamination (e.g., in celiac disease); sumoylation (e.g., in cancer, neurodegenerative disease, and heart disease); acylation (e.g., O-acylation, N-acylation, S-acylation); acetylation; deacetylation; formylation; lipoylation; myristoylation; palmitoylation, alkylation; methylation; demethylation; isoprenylation (e.g., farnesylation, geranylation); lipidation; amidation (e.g., at the C-terminus); arginylation; polyglutamylation; polyglycylation; diphthamide; gamma-carboxylation; glycosylation; polysialylation; glypiation; hydroxylation; iodination; the covalent attachment of nucleotides; adenylation; ADP-ribosylation; flavin attachment; nitrosylation; oxidation; phosphopantetheinylation; pyroglutamate formation; sulfation; selenoylation; ISGylation; SUMOylation; ubiquitination; neddylation; deimination; deamidation; eliminylation; disulfide bridge formation; and racemization.

In certain embodiments, the epitopes are derived from human CD59. In still further embodiments, the epitopes correspond to non-overlapping regions of human CD59. In certain embodiments, the epitopes correspond to overlapping regions of human CD59. In still certain embodiments, the compound comprises two epitopes from human CD59 joined by a linker. In further embodiments, the compound comprises three epitopes from human CD59 joined by one or more linkers. In further embodiments, the epitopes are at least 99%, 98%, 97%, 96%, 95%, 94%, 93%, 92%, 91%, 90%, 89%, 88%, 87%, 85%, 86%, 85%, 84%, 83%, 82%, 81%, or 80% homologous to a peptide segments from human CD59.

In certain embodiments, the compound comprises an epitope derived from human CD59, wherein the epitope comprises a post-translational modification. In further embodiments, the post-translational modification is a glycated amino acid residue. In certain embodiments, the epitope is [$A^{39,44}$, $C^{50}$]hCD59(37-50). In further embodiments, the epitope is $N^\alpha$-Ac[$A^{44,64,65}$]hCD59(44-66)$NH_2$.

In further embodiments, the glycated amino acid residue is lysine. In further embodiments, the glycated amino acid residue results in an epitope with a glycation motif. In still further embodiments, the glycation motif is $R^{15}$—$K_{41}$—$R^{16}$, wherein $R^{15}$ is absent, an amino acid, or a peptide sequence which is identical or homologous to a peptide sequence selected from residues 30-40 of human CD59; $R^{16}$ is absent, an amino acid, or a peptide sequence which is identical or homologous to a peptide sequence selected from residues 42-60 of human CD59. In further embodiments, $R^{15}$ has one or more amino acid deletions, insertions, or substitutions relative to a peptide segment selected from residues 30-40 of human CD59. In still further embodiments, $R^{16}$ has one or more amino acid deletions, insertions, or substitutions relative to a peptide segment selected from residues 42-60 of human CD59. In further embodiments, the glycation motif is at least 99%, 98%, 97%, 96%, 95%, 94%, 93%, 92%, 91%, 90%, 89%, 88%, 87%, 85%, 86%, 85%, 84%, 83%, 82%, 81%, or 80% homologous to $R^{15}$—$K_{41}$—$R^{16}$ of human CD59. In certain embodiments, the glycation motif is $WK_{41}FEH$. In certain embodiments, the glycation motif is $NKAWK_{41}FEHANFNDC$. In certain embodiments, $K_{41}$ is glycated. In certain embodiments, $K_{41}$ is glycated with a linear and reduced glucitollysine moiety, as shown below.

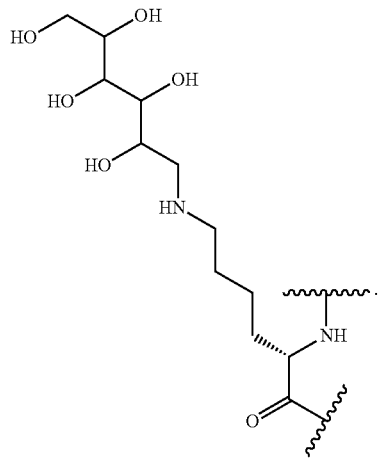 [SMILES: *N[C@@H](CCCCNCC(O)C(O)C(O)C(O)CO)C(*)=O]

The linear and reduced glucitollysine moiety is prepared by a reduction of the corresponding Schiff's base, as shown below.

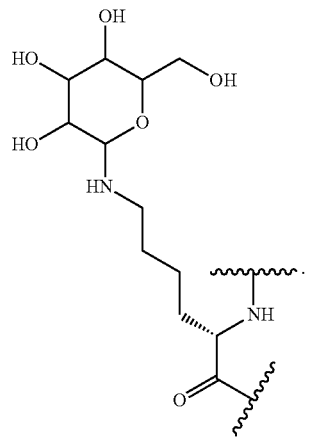

In certain embodiments, $K_{41}$ is glycated with an Amadori product, as shown below.

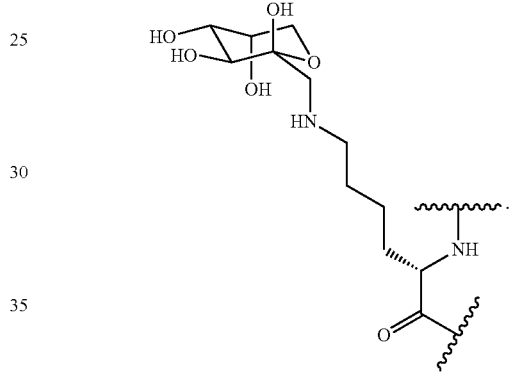

In further embodiments, the compound comprises a second epitope. In certain embodiments, the second epitope is a peptide segment selected from residues 44-66 of human CD59. In still further embodiments, the second epitope is at least 99%, 98%, 97%, 96%, 95%, 94%, 93%, 92%, 91%, 90%, 89%, 88%, 87%, 85%, 86%, 85%, 84%, 83%, 82%, 81%, or 80% homologous to a peptide segment selected from residues 44-66 of human CD59.

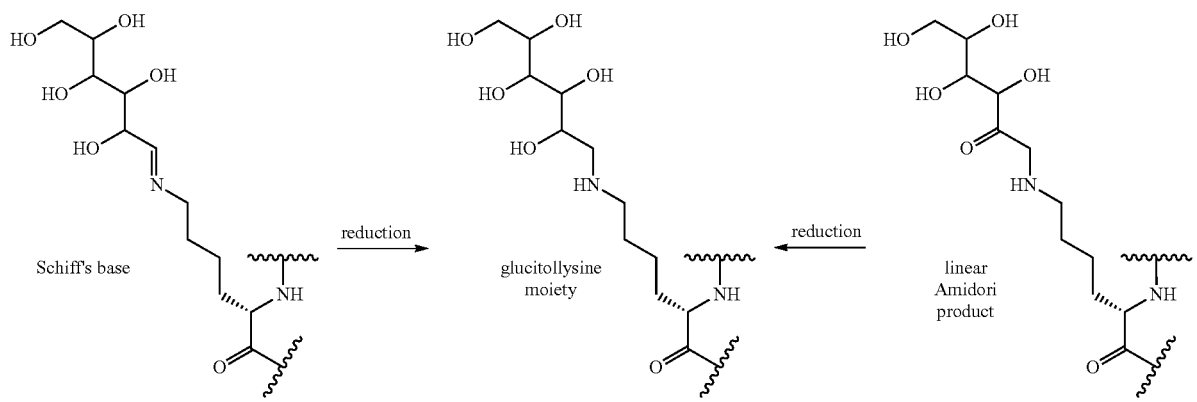 [SMILES: *N[C@@H](CCCC/N=C/C(O)C(O)C(O)C(O)CO)C(*)=O ; *N[C@@H](CCCCNCC(O)C(O)C(O)C(O)CO)C(*)=O ; *N[C@@H](CCCCNCC(=O)C(O)C(O)C(O)CO)C(*)=O]

In certain embodiments, $K_{41}$ is glycated with a cyclized glycosylamine moiety, as shown below.

In further embodiments, the compound comprises an additional epitope. In certain embodiments, the additional epitope is a peptide segment selected from residues of human CD59. In still further embodiments, the second epitope is at least 99%, 98%, 97%, 96%, 95%, 94%, 93%, 92%, 91%, 90%, 89%, 88%, 87%, 85%, 86%, 85%, 84%, 83%, 82%, 81%, or 80% homologous to a peptide segment selected from residues of human Uses In certain aspects, surrogate compounds of the invention have diagnostic utilities. For example, these surrogate compounds can be used as calibration standards in diagnosing and monitoring the response to treatment of a variety of diseases or disorders associated with the post-translational modification of proteins. In certain aspects, the invention includes methods to determine the levels of post-translationally modified proteins (e.g., glycated human CD59) in cells, tissues, or samples from subjects by using the surrogate compounds of the invention as calibration standards. The methods of the invention may be used to monitor the levels of a post-translationally modified protein in a subject over time.

In one aspect, the present invention relates to the use of the antibodies and/or antigen-binding fragments for detecting in samples both the surrogate compounds of the invention and/or the endogenous post-translationally modified proteins from which the surrogate compounds were designed. Samples include histological or cytological specimens, tissue and body fluid samples, biopsies, and the like. The inventive methods can be used to distinguish, in a sample or a subject, the level of endogenous proteins that have a post-translational modification associated with a disease or disorder from the level of endogenous proteins that do not have the post-translational modification. This method involves providing a known concentration of surrogate compound in a sample, and an antibody or an antigen-binding binding fragment thereof, which specifically binds to an epitope in the surrogate compound. This method further involves using a known concentration of the surrogate compound to "calibrate the antibody" by measuring the extent to which the antibody binds the epitope in the surrogate compound. This method further involves using the "calibrated antibody" to quantify the amount of endogenous post-translationally modified protein in a sample which carries the same epitope as that found in the surrogate compound.

In certain embodiments, diagnostic methods comprising the surrogate compounds of the invention are performed in conjunction with a therapeutic regimen. It will be understood that a therapeutic regimen may be either prophylactic or for the treatment of a subject with an existing condition associated with a post-translational modification (e.g., diabetes). Thus, the methods of the invention may be used to monitor a subject's response to prophylactic therapy and/or treatment of an existing condition. The methods of the invention may also be useful to monitor the progression or regression of a condition in a subject. In certain embodiments, the condition is a diabetic or pre-diabetic condition. In further embodiments, surrogates comprising epitopes of CD59 are used to diagnose or monitor a diabetic or pre-diabetic condition in a subject.

Subjects to which the present invention can be applied are pre-diabetic or diabetic subjects. The term "diabetic" as used herein, means an individual who, at the time the sample is taken, has a primary deficiency of insulin and/or an abnormal (e.g., reduced) ability to metabolize glucose as compared with a normal subject, including conditions such as impaired glucose tolerance or impaired fasting glucose, generally termed "pre-diabetes." A pre-diabetic condition can be determined by an oral glucose tolerance test (OGTT). Thus, diabetic patients suffer from a disease in which the levels of blood glucose, also called blood sugar, are above normal. The term diabetic includes, but is not limited to, individuals with juvenile pre-diabetes and diabetes (Type 1 diabetes), adult-onset pre-diabetes and diabetes (Type 2 diabetes), gestational pre-diabetes and diabetes, and any other conditions of insulin deficiency or reduction in the ability to metabolize glucose. The terms "diabetic" and "pre-diabetic" are terms of art, known and understood by those practicing in the medical profession, a formal definition of which can be found in *Harrison's Principles of Medicine* (Harrisons, Vol. 14, *Principles of Internal Medicine*, Eds. Fauci, A. S., E. Braunwald, K. J. Isselbacher, J. D. Wilson, J. B. Martin, D. L. Kasper, S. L. Hauser, D. L. Longo, McGraw-Hill, New York, 1999).

In certain embodiments, the methods of the invention may be used to examine changes in the condition of a subject over time. In further embodiments, the subject is a pre-diabetic or diabetic. In still further embodiments, the methods of the invention may be used to examine changes in the levels of glycated human CD59 in a pre-diabetic or diabetic subject over time. This allows monitoring of the levels of glycated human CD59 in a subject who is believed to be at risk of developing a diabetic condition and also enables monitoring of the levels of glycated human CD59 in a subject who is known to have a diabetic condition. Thus, the methods of the invention may be used to assess the efficacy of a therapeutic treatment of diabetis or pre-diabetis associated with the glycation of CD59. In certain embodiments, the disorder is a diabetic condition that is monitored by assessing the level of glycated K41 human CD59 in a subject at various time points. For example, a level of a subject's glycated K41 human CD59 can be obtained prior to the start of a therapeutic regimen (either prophylactic or as a treatment of an existing diabetic condition), during the treatment regimen, and/or after a treatment regimen, thus providing information on the effectiveness of the regimen in the patient.

In further embodiments, the method is performed in conjunction with a therapeutic treatment regime comprising an anti-diabetic therapy or drug therapy. Drug therapies for regulating blood sugar levels include oral therapies with hypoglycemic agents an/oral anti-diabetic agents, injectable therapies, and the like. Non-drug therapies for regulating blood sugar level include, but are not limited to, dietetic and/or exercise control measures. Diet and exercise alterations include, but are not limited to, reducing caloric intake, and/or increasing fiber intake, and/or decreasing fat intake, and/or increasing exercise level.

Oral drug therapies for regulating blood sugar levels include hypoglycemic agents that may include, but are not limited to, Acarbose; Acetohexamide; Chlorpropamide; Darglitazone Sodium Glimepiride; Glipizide; Glyburide, Repaglinide; Troglitazone; Tolazamide; and Tolbutamide.

Injectable therapies for regulating blood sugar levels include, but are not limited to, Fast-Acting Insulin; Insulin Injection; regular insulin; Prompt Insulin Zinc Suspension; Semilente® insulin. Insulin preparations including, but not limited to, Humalog® Injection; Humulin® R; Iletin II; Novolin R, Purified Pork Regular Insulin; Velosulin BR Human Insulin; Intermediate-acting Insulin; Isophane Insulin Suspension; NPH insulin; isophane insulin; Insulin Zinc Suspension Lente® Insulin; Humulin® L; Humulin® R; Humulin® N NPH; Iletin® II; Lente®; Iletin® II; NPH; Novolin® L; Novolin® N; Purified Pork Lente® insulin; Purified Pork NPH isophane insulin; Intermediate and Rapid-acting Insulin Combinations; Human Insulin; Isophane Suspension/Human Insulin Injection; Humulin® 50/50; Humulin®70/30; Novolin®70/30; Long-acting Insulin; Protamine Zinc Insulin Suspension; Extended Insulin Zinc Suspension; Ultralente® Insulin; and Humulin® U.

Reducing the risk of a disorder associated with abnormally high levels of glycated human CD59 means using treatments and/or medications to reduce glycated human CD59 levels, therein reducing, for example, the subject's risk of vascular complications including but not limited to, diabetic nephropathy, diabetic retinopathy, macro-vascular disease, micro-vascular disease, and diabetic neuropathy.

In certain embodiments, the present invention provides a method for detecting in a sample the presence of a protein with a post-translational modification, said method comprising preparing a reference sample that contains an amount of a reference compound of the invention; obtaining a biological sample from a subject; measuring the amount of the reference compound in the reference sample using an antibody that detects the post-translational modification; measuring the amount of post-translationally modified protein in the biological sample using the antibody; comparing the amount of the reference compound in the reference sample with the amount of the PTM protein in the biological sample.

The present invention provides a method for determining in a subject the regression, progression, or onset of a condition characterized by abnormal levels of a post-translationally modified protein with a post-translationally modified epitope by preparing a reference sample that contains an amount of a reference compound of the invention; obtaining a biological sample from the subject; measuring the amount of the reference compound in the reference sample using an antibody; measuring the amount, if any, of the post-translationally modified protein in the biological sample using the antibody; comparing the amount of the reference compound in the reference sample with the amount of the PTM protein in the biological sample. In certain embodiments, the biological sample is a fluid. In further embodiments, the biological sample is blood. In still further embodiments, the biological sample is urine. In further embodiments, the biological sample is saliva. In still further embodiments, the biological sample is sweat.

In further embodiments, the subject is free of symptoms calling for a therapy with a sugar-regulating therapy. In still further embodiments, the subject is undergoing therapy for regulating blood sugar levels. In further embodiments, the therapy is a non-drug therapy. In still further embodiments, the therapy is a drug therapy. In further embodiments, the drug therapy is an oral blood sugar regulating agent therapy. In still further embodiments, the drug therapy is an injectable drug therapy. In further embodiments, the drug therapy is insulin therapy or an insulin analog therapy. In still further embodiments, the subject is at increased risk of becoming diabetic. In further embodiments, the subject has not received treatment for regulating blood sugar levels.

The amount of the reference compound in the reference sample can be determined by the use of one or more antibodies. In certain embodiments, a first capture antibody is used. The first capture antibody targets and binds an epitope other than the post-translationally modified epitope and thereby captures the reference compound comprising the targeted epitope. In certain embodiments, the capture antibody is mouse anti-human CD59[44-66] mAb 4466-10A7. The first capture antibody can, for example, be immobilized to a surface. In certain embodiments, the surface is a multi-well plate. The surface may also be a Western blot.

A primary detection antibody can also be used. In certain embodiments, the primary detection antibody targets the post-translationally modified epitope of the reference compound that is bound to the first capture antibody. In further embodiments, the primary detection antibody is specific for rabbit anti-glucytollysine mAb.

A secondary detecting/quantifying antibody can be used, wherein the secondary detecting/quantifying antibody targets said primary detecting antibody. In certain embodiments, the secondary detecting/quantifying antibody is goat anti-rabbit HRP-tagged polyclonal Ab.

In certain embodiments, the step of measuring the amount of the reference compound in a reference sample is determined by contacting a first capture antibody immobilized to a surface with the reference sample, said capture antibody targeting an epitope other than the post-translationally modified epitope of the reference compound in the reference sample; contacting the reference compound that is immobilized on the surface by the capture antibody with a primary detecting antibody, said primary detection antibody targeting the post-translationally modified epitope of the reference compound; and contacting the reference compound that is immobilized on the surface by the capture antibody with a secondary detecting/quantifying antibody, said quantifying antibody targeting said primary detecting antibody.

Each of the antibodies of the invention is optionally attached to a detectable label. A detectable label is independently selected from the group consisting of fluorescent label, phosphorescent label, enzyme label, radioactive label, chemiluminescent label, luminescent label, and chromophore label. Each of the antibodies is, independently, a monoclonal or polyclonal antibody.

As noted above, the present invention provides a method for diagnosing a condition or monitoring the regression, progression, or onset of a condition in a subject. The condition being diagnosed or monitored is selected from the group consisting of diabetes, an autoimmune disease, multiple sclerosis, rheumatoid arthritis, systemic lupus erythematosus, primary bilary cirrhosis, celiac disease, and Crohn's disease. In certain embodiments, the condition is diabetes. In further embodiments, the condition is pre-diabetes. In further embodiments, the condition is an autoimmune disease. In still further embodiments, the condition is multiple sclerosis. In further embodiments, the condition is rheumatoid arthritis. In still further embodiments, the condition is systemic lupus erythematosus. In further embodiments, the condition is primary bilary cirrhosis. In still further embodiments, the condition is celiac disease. In further embodiments, the condition is Crohn's disease. In other embodiments, the compounds are useful in diagnosing or following the progression of other diseases associated with the presence of abberent PTM proteins.

Antibodies and Methods of Producing Antibodies

In one aspect, the invention provides an isolated antibody or antigen-binding fragment thereof that binds specifically to an epitope of a compound of the invention. In certain embodiments, the invention provides an isolated antibody or antigen-binding fragment thereof that binds specifically to the post-translationally modified epitope of a compound of the invention. In further embodiments, the post-translational modification of the post-translationally modified epitope is selected from the group consisting of glycation; phosphorylation; lipoylation; citrullination; hypusination; transglutamination; sumoylation; acylation; acetylation; deacetylation; formylation; myristoylation; palmitoylation, alkylation; methylation; demethylation; isoprenylation; lipidation; amidation; arginylation; polyglutamylation; polyglycylation; diphthamide; gamma-carboxylation; glycosylation; polysialylation; glypiation; hydroxylation; iodination; the covalent attachment of nucleotides; adenylation; ADP-ribosylation; flavin attachment; nitrosylation; oxidation; phosphopantetheinylation; pyroglutamate formation; sulfation; selenoylation; ISGylation; SUMOylation; ubiquitination; neddylation; deimination; deamidation; eliminylation; disulfide bridge formation; and racemization. In certain embodiments, the post-translational modification is selected from the group consisting of glycation; phosphorylation; lipoylation; citrullination; hypusination; transglutamination; and sumoylation. In certain embodiments, the post-translationally modification is a glycated lysine residue. In certain embodiments, the post-translationally modification is a glycated lysine residue of human CD59. In certain embodiments, the glycated lysine residue is $K_{41}$ of human CD59. In certain embodiments, lysine is glycated with the linear and reduced glucitollysine moiety to yield a lysine residue of the formula:

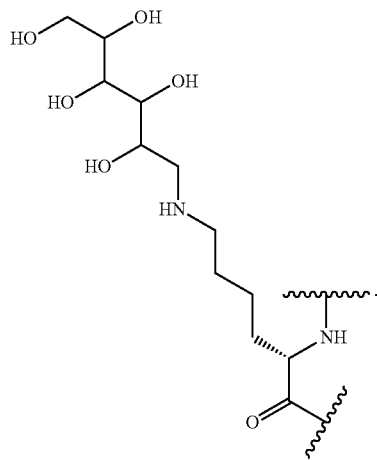

In further embodiments, the post-translational modification is phosphorylation. In certain embodiments, the post-translational modification is a phosphorylation of $S^{51}$ of human eIF2α. In certain embodiments, the post-translational modification is lipoylation. In certain embodiments, the post-translational modification is a lipoylation of the ε-NH$_2$ of $K^{173}$ of human PDC-E$_2$.

In another aspect, the invention provides an isolated antibody or antigen-binding fragment thereof that binds specifically to an epitope other than the post-translationally modified epitope of a compound of the invention. In certain embodiments, the epitope comprises a C-terminus or N-terminus. In certain embodiments, the epitope is a peptide segment of human CD59 selected from residues other than residues 37-50 of human CD59. In certain embodiments, the epitope is a peptide segment selected from residues 44-66 of human CD59. In certain embodiments, the epitope is a peptide segment of the carboxyl-terminal sequence comprising $C^{278}$ of human eIF2α. In certain embodiments, the epitope is a peptide segment comprising a peptide segment $G^{475}$ through $A^{499}$ of human PDC-E$_2$. In certain embodiments, the antibody is monoclonal, polyclonal, recombinant, or humanized.

In another aspect, the invention provides a method of making an antibody that specifically binds to the post-translationally modified epitope of the compound of the invention but not to a corresponding epitope that is not post-translationally modified in another compound or in the native protein, comprising: preparing an immunogenic composition comprising the post-translationally modified epitope of the compound of the invention, and immunizing an animal with the immunogenic composition.

In yet another aspect, the invention provides a method of making an antibody that binds specifically to an epitope other than the post-translationally modified epitope of the compound of the invention, comprising: preparing an immunogenic composition comprising an epitope other than the post-translationally modified epitope of the compound of the invention, and immunizing an animal with the immunogenic composition. In certain embodiments, the inventive methods further comprise: removing a lymph node from the immunized animal, harvesting cells from the removed lymph node, fusing the harvested cells with mouse myeloma cells to make hybridomas, expanding the hybridomas, identifying a hybridoma that produces an antibody that specifically binds to the immunogenic polypeptide, and collecting the antibody produced by the hybridoma. In certain embodiments, the animal is selected from the group consisting of a mouse, rabbit, hamster, sheep, or goat.

As used herein, the term "antibody" refers to a glycoprotein comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antigen-binding fragment" of an antibody or "antibody fragment" as used herein, refers to one or more portions of an antibody that retain the ability to specifically bind to an antigen (e.g., a post-translationally modified epitope, such as glycated CD59, of the compounds of the invention). In some embodiments, the glycated CD59 epitope is a K41-glycated CD59 epitope. It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546) which consists of a $V_H$ domain; and (vi) an isolated complementarity determining region (CDR). Furthermore, although the two domains of the Fv fragment, V and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference as well as by other techniques known to those with skill in the art. The fragments are screened for utility in the same manner as are intact antibodies.

As used herein, "specific binding" refers to antibody binding to a predetermined antigen with a preference that enables the antibody to be used to distinguish the antigen from others to an extent that permits the diagnostic assays described herein. Specific binding to compounds of the invention comprising a post-translationally modified epitope (e.g., glycated CD59 epitope) means that the antibody preferentially binds a compound comprising a post-translationally modification versus a compound or protein that without the same post-translational modification. Typically, the antibody binds with an affinity that is at least two-fold greater than its affinity for binding to an antigens other than the predetermined antigen. In some embodiments, an antibody or antigen-binding fragment thereof of the invention specifically binds to post-translationally modified epitopes (e.g., K41-glycated CD59 epitope) of the inventive compounds.

The isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g. IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA1, IgA2, IgAsec, IgD or IgE or could consist of a Fab fragment, a F(ab')$_2$ fragment, and a Fv fragment.

The antibodies of the present invention can be polyclonal, monoclonal, or a mixture of polyclonal and monoclonal antibodies. The antibodies can be produced by a variety of techniques well known in the art. Example of methods to produce a monoclonal antibody that specifically binds to post-translationally modified epitopes (e.g., K41-glycated CD59 epitope) of the inventive compounds and to non-post-translationally modified epitopes of the inventive compounds are commonly known to those of ordinary skill in the art.

Monoclonal antibody production may be effected by techniques that are known in the art. The term "monoclonal antibody," as used herein, refers to a preparation of antibody molecules of single molecular composition. A monoclonal antibody displays a single binding specificity and affinity for a particular epitope. The process of monoclonal antibody production involves obtaining immune somatic cells with the potential for producing antibody, in particular B lymphocytes, which have been previously immunized with the antigen of interest either in vivo or in vitro and that are suitable for fusion with a B-cell myeloma line.

Mammalian lymphocytes typically are immunized by in vivo immunization of the animal (e.g., a mouse) with the desired protein or polypeptide, or with a compound of the invention or a fragment thereof. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse is preferred. However, other mouse strains, rabbit, hamster, sheep and frog may also be used as hosts for preparing antibody-producing cells. See; Goding (in Monoclonal Antibodies: Principles and Practice, 2d ed., pp. 60-61, Orlando, Fla., Academic Press, 1986). Mouse strains that have human immunoglobulin genes inserted in the genome (and which cannot produce mouse immunoglobulins) can also be used. Examples include the HuMAb mouse strains produced by Medarex/GenPharm International, and the XenoMouse strains produced by Abgenix. Such mice produce fully human immunoglobulin molecules in response to immunization.

Those antibody-producing cells that are in the dividing plasmablast stage fuse preferentially. Somatic cells may be obtained from the lymph nodes, spleens and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature* 256:495 (1975), which is hereby incorporated by reference.

In another aspect, the invention provides a hybridoma cell line that produces any one of the antibodies of the invention. Myeloma cell lines suited for use in hybridoma-producing fusion procedures preferably are non-antibody-producing, have high fusion efficiency, and enzyme deficiencies that render them incapable of growing in certain selective media which support the growth of the desired hybridomas. Examples of such myeloma cell lines that may be used for the production of fused cell lines include Ag8, P3-X63/Ag8, X63-Ag8.653, NS1/1.Ag 4.1, Sp2/0-Ag14, FO, NSO/U, MPC-11, MPC11-X45-GTG 1.7, S194/5XX0 Bul, all derived from mice; R210.RCY3, Y3-Ag 1.2.3, IR983F and 4B210 derived from rats and U-266, GM1500-GRG2, LICR-LON-HMy2, UC729-6, all derived from humans (Goding, in *Monoclonal Antibodies: Principles and Practice*, 2d ed., pp. 65-66, Orlando, Fla., Academic Press, 1986; Campbell, in *Monoclonal Antibody Technology, Laboratory Techniques in Biochemistry and Molecular Biology*, vol. 13, Burden and Von Knippenberg, eds. pp. 75-83, Amsterdam, Elsevier, 1984).

Fusion with mammalian myeloma cells or other fusion partners capable of replicating indefinitely in cell culture is effected by standard and well-known techniques, for example, by using polyethylene glycol ("PEG") or other fusing agents (See Milstein and Kohler, *Eur. J. Immunol.* 6:511 (1976), which is hereby incorporated by reference).

Procedures for raising polyclonal antibodies are well known to those of ordinary skill in the art. For example anti-(post translational modification (e.g., glycated CD59) surrogate) polyclonal antibodies may be raised by administering a compound of the invention or fragment thereof comprising an epitope with the post translational modification (e.g., glycated CD59) subcutaneously to New Zealand white rabbits which have first been bled to obtain pre-immune serum. A compound of the invention or fragment thereof can be injected at a total volume of 100 µl per site at six different sites, typically with one or more adjustments. The rabbits are then bled two weeks after the first injection and periodically boosted with the same antigen three times every six weeks. A sample of serum is collected 10 days after each boost. Polyclonal antibodies are recovered from the serum, preferably by affinity chromatography using a compound of the invention or fragment thereof to capture the antibody. This and other procedures for raising polyclonal antibodies are disclosed in E. Harlow, et al., editors, Antibodies: A Laboratory Manual (1988), which is hereby incorporated by reference. In some embodiments, the epitope of the inventive compounds that is recognized by the polyclonal antibody includes glycated lysine that corresponds to the K41 in mature CD59 polypeptide.

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In yet another aspect, the invention provides an isolated antibody of the invention, wherein the antibody is attached to a detectible label. In certain embodiments, the detectable label is selected from the group consisting of a fluorescent label, enzyme label, radioactive label, phosphorescent label, chemiluminescent label, luminescent label, affinity label, and chromophore label. Detectible labels useful in the invention include, but are not limited to: a fluorescent label, an enzyme label, a radioactive label, a nuclear magnetic resonance active label, a luminescent label, and a chromophore label. The detectible labels of the invention can be attached to the antibodies or antigen-binding fragments thereof by standard protocols known in the art. In some embodiments, the detectible labels may be covalently attached to an antibody or antigen-binding fragment of the invention. The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In some embodiments, it is contemplated that one may wish to first derivatize the antibody, and then attach the detectible label to the derivatized product. Suitable cross-linking agents for use in this manner include, for example, SPDP (N-succinimidyl-3-(2-pyridyldithio) propionate), and SMPT, 4-succinimidyl-oxycarbonyl-methyl-(2-pyridyldithio)toluene. In some embodiments, a radionuclide may be coupled to an antibody or antigen-binding fragment thereof by chelation.

Kits

In certain embodiments, the present invention relates to a kit for carrying out the methods in accordance with the present invention. In general, the kit comprises one or more containers filled with one or more of the compounds of the inventive methods. The kit may include these compounds packaged conveniently for performing the inventive method.

The present invention provides kits for detecting the presence of a post-translationally modified protein in a biological sample. The kit may include a first container with a reference sample comprising a reference compound, (i.e., a surrogate of the post-translationally modified protein) and instructional material for use of the kit. The post-translationally modified protein is optionally attached to a detectable label. In certain embodiments, the detectable label is selected from the group consisting of fluorescent labels, enzyme labels, radioactive labels, phosphorescent labels, chemiluminescent labels, luminescent labels, affinity labels, and chromophore labels. The kits may further include a second container containing a capture antibody, said capture antibody binding to an epitope other than the post-translationally modified epitope of the reference compound in the reference sample; a third container containing a primary detecting antibody, said detection antibody directed to the post-translationally modified epitope of the reference compound; and/or a fourth container containing a secondary detecting/quantifying antibody, said quantifying antibody binding to said primary detecting antibody. In still further embodiments, each of the antibodies is optionally attached to a detectable label. In certain embodiments, the detectable label is selected from the group consisting of fluorescent labels, enzyme labels, radioactive labels, phosphorescent labels, chemiluminescent labels, luminescent labels, affinity labels, and chromophore labels. The antibodies of kit may be monoclonal or polyclonal antibodies. The antibodies may be provided in lyophilized form or in an aqueous medium.

A kit may comprise any of a number of additional reagents, buffering agents, containers, and/or controls in any combination. All of the various combinations are not set forth explicitly but each combination is included in the scope of the invention.

The Preparation of Surrogates of Post-Translationally Modified Proteins

The invention also includes methods of preparing surrogates of post-translationally modified proteins as described herein. In certain embodiments, the compounds are prepared in solution. In further embodiments, the compounds are prepared in the solid-phase. In still further embodiments, the compounds are prepared in the solid-phase and in solution. The general principles of solid-phase peptide synthesis are described in *Solid-Phase Synthesis: A Practical Guide*, Fernando Albericio, CRC Press: 2000, the entire contents of which are incorporated herein by reference.

The surrogate compounds comprise more than one epitope and at least one linker, wherein at least one epitope is post-translationally modified. In certain embodiments, the linker and epitopes are joined (i.e., covalently bound) in solution. In certain embodiments, the linker and epitopes are joined in the solid phase. In certain embodiments, the post-translational modification is installed into an epitope by incorporating individual amino acids comprising the desired post-translational modification, or a protected form thereof, into a growing polypeptide chain using a stepwise solid-phase synthetic strategy, as described in the U.S. provisional patent application, U.S. Ser. No. 61/377,060 ("the '060 application"), the entirety of which is incorporated herein by reference. In further embodiments, the post-translational modification is installed into a polypeptide by incorporating individual amino acids comprising the post-translational modification, or protected forms thereof, into a growing polypeptide chain using a solution-phase synthetic strategy. In still further embodiments, the post-translational modification is installed into an polypeptide by incorporating individual amino acids comprising the post-translational modification, or protected forms thereof, into a growing polypeptide chain using a combination of solution-phase and stepwise solid-phase synthetic strategies.

In certain embodiments, the post-translational modification is installed into an epitope that has already been synthesized. In certain embodiments, the sidechains of the epitope are not protected. In further embodiments, some or all of the sidechains of the epitope are protected. In certain embodiments, the post-translational modification is added to a polypeptide in solution. In further embodiments, the post-translational modification is added to a polypeptide in the solid-phase.

The invention further utilizes methods described in the '060 application for the solid phase synthesis of a peptide of the sequence,

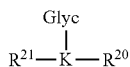

or a protected form thereof, comprising a lysine derivative (K-Glyc) that is selected from the group of the formulae consisting of:

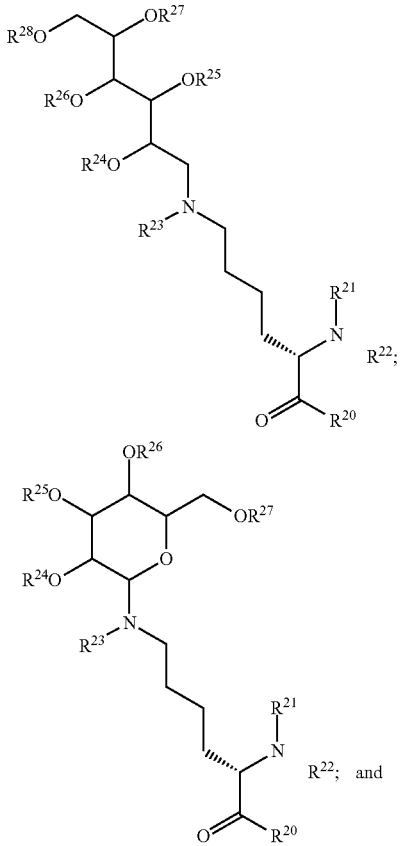

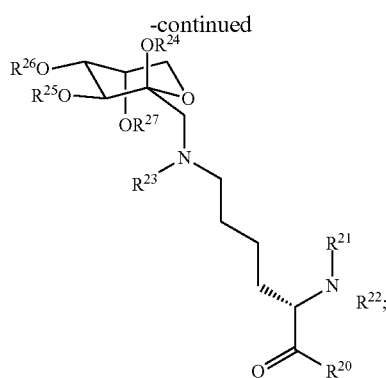

or a protected form thereof;

wherein each $R^{20}$ is, independently, OH, $OPg^3$, or a peptide sequence which is identical or homologous to a peptide sequence selected from residues 42-103 of human CD59;

wherein each $R^{21}$, $R^{22}$, and $R^{23}$ is, independently, hydrogen, $Pg^2$, or a peptide sequence which is identical or homologous to a peptide sequence selected from residues 1-40 of human CD59; and wherein each $R^{24}$, $R^{25}$, $R^{26}$, $R^{27}$, and $R^{28}$ is, independently, hydrogen or $Pg^1$, wherein two $Pg^1$ groups may combine to form a heterocyclic ring; and wherein each sidechain of each peptide sequence may comprise

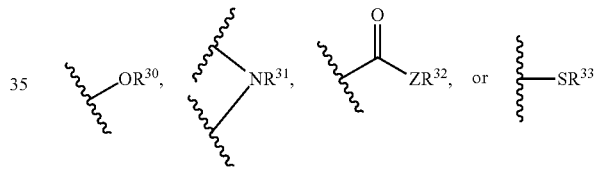

groups; and each $R^{30}$ is hydrogen or $Pg^1$;
each $R^{31}$ is hydrogen or $Pg^2$;
each Z is O or NH;
each $R^{32}$ is hydrogen, $Pg^2$, or $Pg^3$;
each $R^{33}$ is hydrogen or $Pg^4$;
each $Pg^1$ is an independently selected hydroxyl protecting group;
each $Pg^2$ is an independently selected amino protecting group;
each $Pg^3$ is an independently selected carboxyl protecting group; and
each $Pg^4$ is an independently selected thiol protecting group.

In certain embodiments, $R^{20}$ is a peptide sequence which is identical or homologous to a peptide sequence selected from residues 37-40 of human CD59. In further embodiments, $R^{20}$ is residue 37 of human CD59. In still further embodiments, $R^{20}$ is a peptide sequence which is identical or homologous to a peptide sequence selected from residues 42-50 of human CD59. In further embodiments, $R^{20}$ is residues 42-44 of human CD59.

In certain embodiments, $R^{21}$ is hydrogen.

In certain embodiments, the invention provides methods of preparing

(SEQ ID NO: 1) or a protected form thereof, wherein "Glyc" is a 1-deoxy-D-glucitol-1-yl moiety, the cyclized glycosylamine, or the Amadori adduct, as described above. In certain preferred embodiments "Glyc" is the 1-deoxy-D-glucitol-1-yl moiety.

In further embodiments, the invention provides methods of preparing

(SEQ ID NO: 10) or a protected form thereof.

In certain embodiments, the invention provides methods of preparing

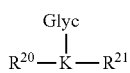

by stepwise synthesis from a protected derivative of glycated lysine, wherein the glycated lysine before protection is selected from the group consisting of:

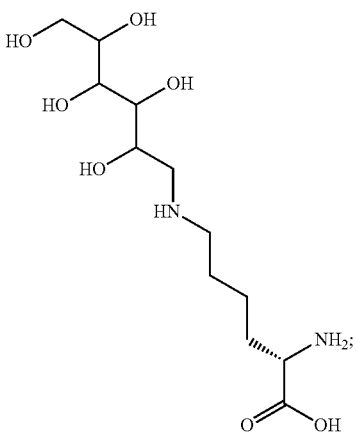

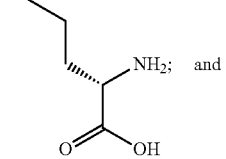

In certain embodiments, the invention provides methods wherein each $Pg^1$ is an independently selected hydroxyl protecting group as defined herein, each $Pg^2$ is an independently selected amino protecting group as defined herein, and wherein two $Pg^1$ groups may combine to form a heterocyclic ring. In certain embodiments, two $Pg^1$ groups may combine to form an acetonide protecting group. In certain embodiments, two $Pg^1$ groups may combine to form a 4,5-di-O-isopropylidene protecting group. In certain embodiments, each $Pg^1$ group is independently selected from the group consisting of (tert-butyl)ether, methyl ether, benzyl ether, 4-methoxybenzyl ether, allyl ether, methoxymethyl ether, triphenylmethyl (Trt), and acetate ester protecting groups. In certain embodiments, each $Pg^2$ group is independently selected from the group consisting of t-butyl carbamate (BOC), carboxybenzyl carbamate (Cbz), (9-fluorenylmethyl) carbamate (FMOC), (trichloroethyl) carbamate (TROC), triphenylmethyl (Trt), and N-[1-(4,4-dimethyl-2,6-dioxocyclohex-1-ylidene)ethyl] (Dde) protecting groups.

In certain embodiments, the invention provides methods wherein the glycation step is performed on a resin. In further embodiments, the invention provides methods wherein the glycation step is performed in solution. In certain embodiments, the invention provides methods comprising a 2-fold to 100-fold molar excess of D-glucose. In further embodiments, the invention provides methods wherein the glycation step is performed at temperatures above 50° C. In still further embodiments, the invention provides methods wherein the glycation step is performed at temperatures above 25° C., 30° C., 35° C., 40° C., or 45° C. In some embodiments, the invention provides methods wherein the glycation step is performed at temperatures above 55° C., 60° C., 65° C., 70° C., 75° C., 80° C., 85° C., 90° C., 95° C., or 100° C.

The linkers of the invention can be purchased from a commercial source or prepared according to the standard techniques of synthetic organic chemistry as described in *Organic Chemistry*, Thomas Sorrell, University Science Books, Sausalito, 1999; Smith and March, *March's Advanced Organic Chemistry*, 5th Edition, John Wiley & Sons, Inc., New York, 2001; and Larock, *Comprehensive Organic Transformations*, VCH Publishers, Inc., New York, 1989. Likewise, the linkers and epitopes can be joined according to the standard techniques of synthetic organic chemistry and as described in U.S. patent publication U.S.S.N., 2010/0112708, the entirety of which is incorporated herein by reference.

These and other aspects of the present invention will be further appreciated upon consideration of the following Examples, which are intended to illustrate certain particular embodiments of the invention but are not intended to limit its scope, as defined by the claims.

EXAMPLES

General Methods

Unless otherwise noted, all the materials were obtained from commercial suppliers and used without further purification. All solvents were commercially available and of polypeptide synthesis grade. Protected amino acids were purchased from Novabiochem. Polypeptide synthesis was performed both manually on an Advanced ChemTech PLS and automatically on a Prelude Protein Technologies synthesizer. Analytical HPLC analysis was done on XTerra MS $C_{18}$ column, 5 µm, 3×100 mm in a linear gradient at 1 mL/min of A in B where A=0.1% AcOH in acetonitrile and B=0.1% AcOH in water).

Example 1

General peptide coupling procedures for the stepwise solid-phase polypeptide synthesis of derivatives of such as $N^\alpha$-Ac[Lys$^{41}$($N^\epsilon$-1-deoxyfructosyl)]human CD59(37-50)-OH. The above-indicated polypeptide was manually synthesized from 155 mg of Fmoc-Cys(Trt)-Rink resin starting material (0.41 meq/g, 0.0633 mmol) using PyBOP, HOBt, and DIEA coupling reagents in 5/5/10-fold molar excess. Successive $N^\alpha$-Fmoc protected amino acids were added in a 5-fold molar excess and stirred 2-3 hours at ambient temperature in the dark. Side-chain protecting groups of the $N^\alpha$-Fmoc protected amino acids included: Asn(Trt), Asp(OtBu), Glu (OtBu), His($N^{im}$-Trt), Lys($N^\epsilon$-Boc) and Trp($N^{im}$-Boc).

Example 2A

Synthesis of 2-(9H-Fluoren-9-ylmethoxycarbonylamino)-6-(2,3,4,5,6-pentahydroxy-hexylamino)-hexanoic acid [Fmoc-Lys(gluc)-OH]:[$N^\alpha$-Fmoc-$N^\epsilon$-(1-deoxy-D-glucitol-1-yl)-L-lysine] (1)

A solution of $N^\alpha$-Fmoc-L-lysine (1.84 g, 5 mmol) and sodium cyanoborohydride (378 mg, 6 mmol), in THF/H$_2$O (50/50 v/v, 30 mL) at pH 7.0 (adjusted with 0.1N HCl) was mixed with an aqueous solution (2.5 mL) of D-glucose (2.7 g, 15 mmol). The mixture was stirred for 72 h at 37° C., then concentrated under vacuum. The pure compound was obtained as a powder (2.29 g, 55%) after purification by RP C-18 silica gel chromatography using a gradient of 0-30% of solvent A in B (A=0.1% AcOH in acetonitrile; B=0.1% AcOH in H$_2$O; Flow rate=15 mL/min). Rt=10.10 min (gradient 10% to 60% in 25 min). MS$^+$(ESI) m/z 533.29 ([M+H]$^+$), calcd. 532.24 (M$^+$). m.p.: 90-92° C. $^1$H-NMR (DM-SOd$_6$, 400 MHz): 7.88 (d, J=7.6, 2H), 7.69-7.71 (m, 2H), 7.41 (t, J=7.6, 2H), 7.32 (t, J=7.6, 2H), 4.19-4.28 (m, 5H), 3.84-3.94 (m, 2H), 3.58 (m, 1H), 3.38-3.47 (m, 3H), 3.87 (m, 2H), 3.05 (m, 1H), 2.87-2.93 (m, 3H), 1.58-1.71 (m, 4H), 1.32-1.35 (m, 2H). Elemental analysis ($C_{27}H_{36}N_2O_9$) C, 58.47% (calcd 60.89%); H, 7.29% (calcd 6.81%); N, 5.00 (calcd 5.26%).

Example 2B

Synthesis of 6-[tert-Butoxycarbonyl-(2,3,4,5,6-pentahydroxy-hexyl)-amino]-2-(9H-fluoren-9-yl-methoxycarbonylamino)-hexanoic acid: {$N^\alpha$-Fmoc-Lys[$N^\epsilon$-Boc-$N^\epsilon$-(1-deoxy-D-glucitol-1-yl)]} (2)

A solution of (1) (1.34 g, 2.5 mmol) in 10% TEA in methanol was treated with di-tert-butyl-dicarbonate (1.15 mL, 5 mmol), in presence of few drops of H$_2$O to achieve complete solubility, was stirred at room temperature for 16 h. The residue obtained after concentration under vacuum was purified by RP C-18 silica gel chromatography using a gradient of 0-50% of solvent A in B (A=acetonitrile; B=H$_2$O; Flow rate=15 mL/min). The pure product was obtained after lyophilization as a white powder (1.49 g, 95%). Rt=20.05 min (gradient 10% to 60% in 25 min). MS$^+$(ESI) m/z 632.92 ([M+H]$^+$), calcd. 632.29 (M$^+$). m.p.: 78-80° C. $^1$H-NMR 7.86 (d, J=7.5, 2H), 7.69 (d, J=7.2, 2H), 7.40 (t, J=7.2, 2H), 7.30 (t, J=7.5, 2H), 4.18-4.26 (m, 3H), 3.31-3.56 (m's, 9H), 3.09-3.27 (m, 4H), 1.40 (m, 2H), 1.33 (s, 9H), 1.20-1.26 (m, 2H). Elemental analysis ($C_{32}H_{44}N_2O_{11}$) C, % 58.10 (calcd 60.75%); H, 6.77% (calcd 7.01%); N, 4.08% (calcd 4.43%).

Example 3

Synthesis of the Ac-{Ala$^{39,45}$,Lys$^{41}$[$N^\epsilon$-(1-deoxy-D-glucitol-1-yl)],Cys$^{50}$}hCD59(37-50) antigen: Ac-Asn-Lys-Ala-Trp-Lys[$N^\epsilon$-(1-deoxy-D-glucitol-1-yl)]-Phe-Glu-His-Ala-Asn-Phe-Asn-Asp-Cys-OH (SEQ ID NO: 21) (3)

Figure 1:
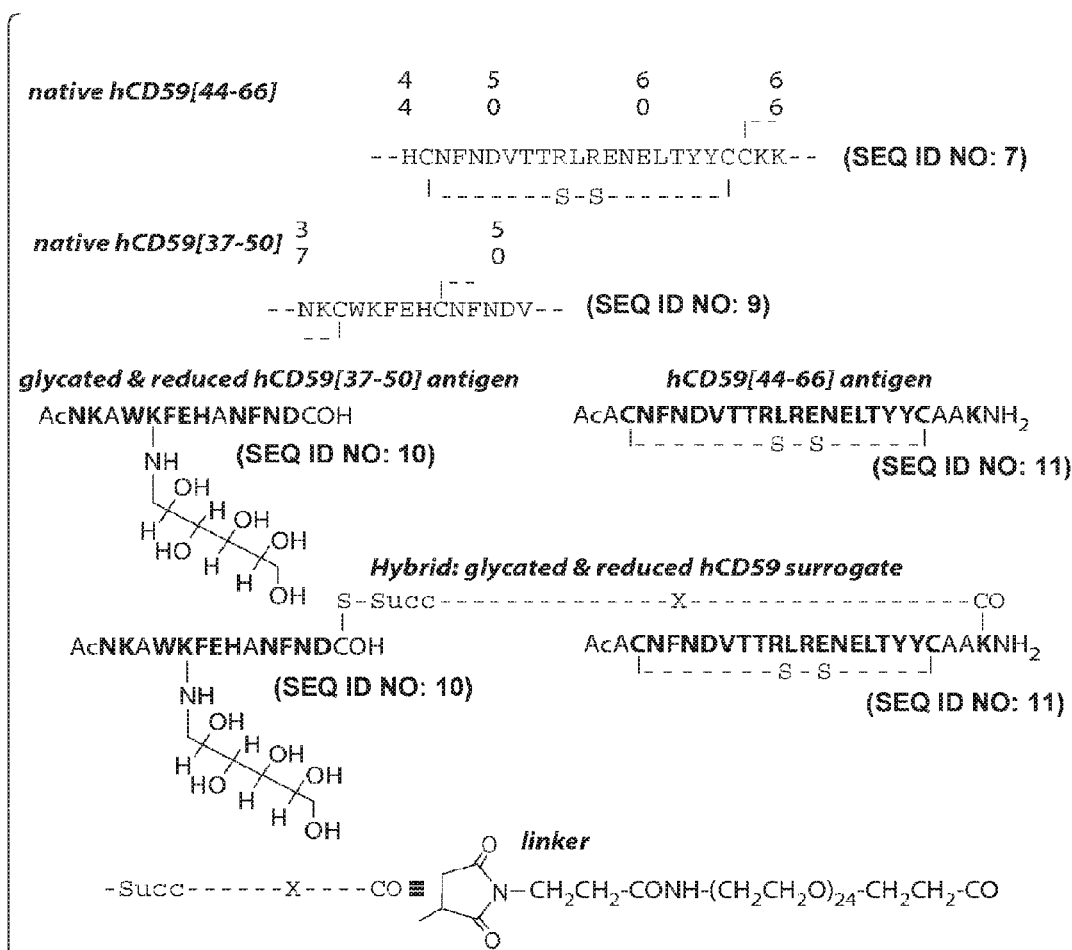
FIG. 1 depicts native human CD59[37-50] (SEQ ID NO:9) and human CD59[44-66] (SEQ ID NO:7); glycated and reduced human CD59[37-50] (SEQ ID NO:10) antigen and human CD59[44-66] (SEQ ID NO:11) antigen; the corresponding glycated and reduced human CD59 surrogate and the comprised linker.
Figure 2:
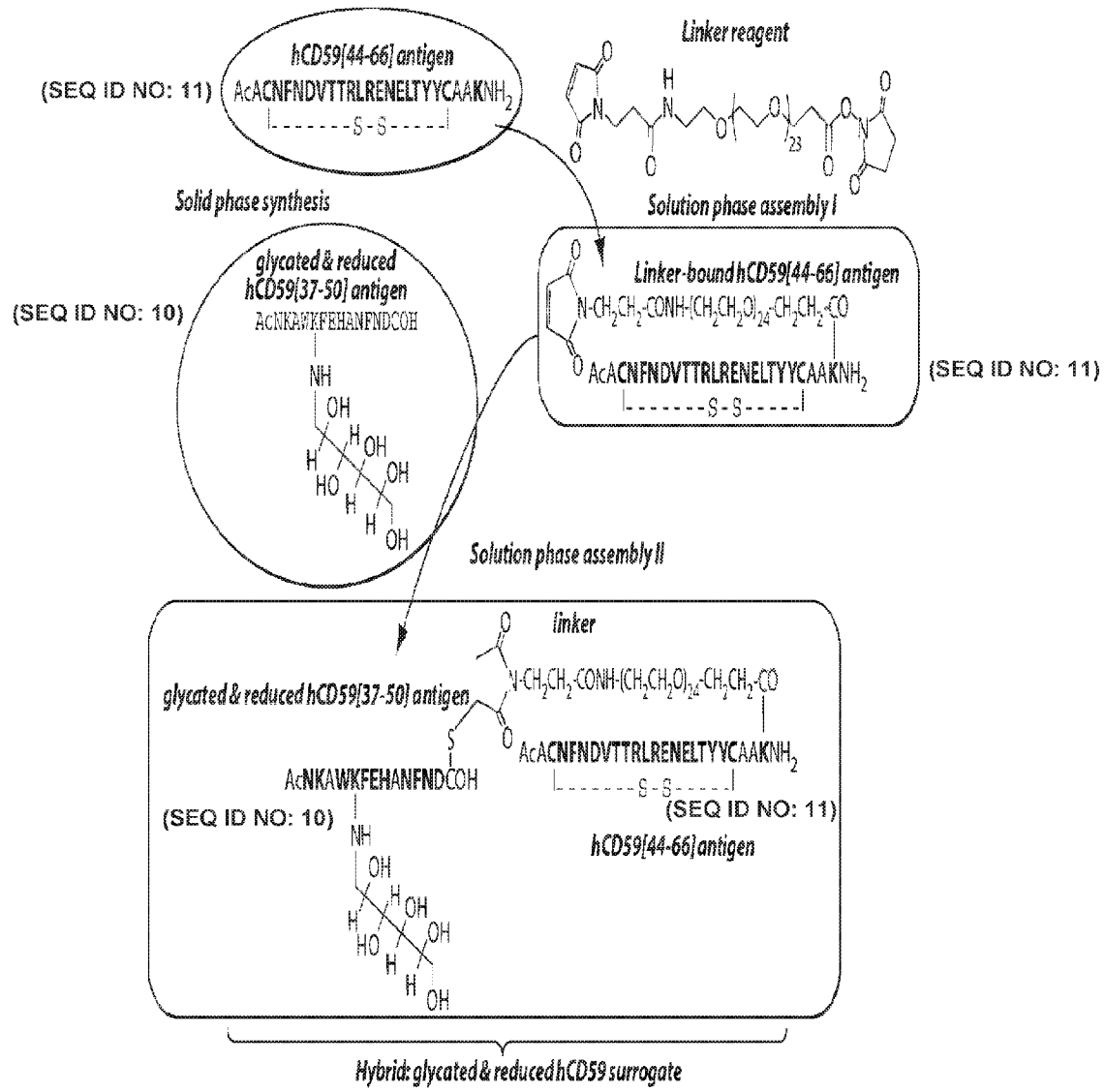
FIG. 2 depicts the solution phase assembly of glycated and reduced human CD59 surrogate from the glycated and reduced human CD59[37-50] antigen and the human CD59 [44-66] antigen linked through the bifunctional PEG linker.
Figure 3:
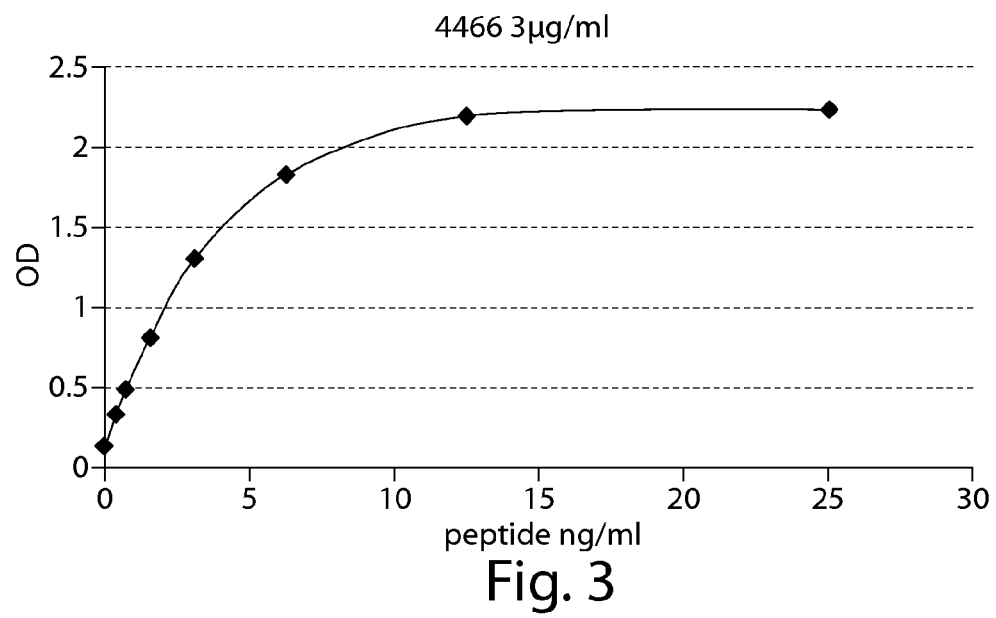
FIG. 3 depicts the titration curve obtained in a sandwich ELISA assay in which glycated and reduced human CD59 surrogate was captured with 4466-10A7 (3 µg/mL, mouse anti-human CD59[44-66] mAb), treated with secondary rabbit anti-glucytollysine mAb (0.7 µg/mL) and detected with goat anti-rabbit HRP-tagged polyclonal IgG (1:5000).
Figure 4:
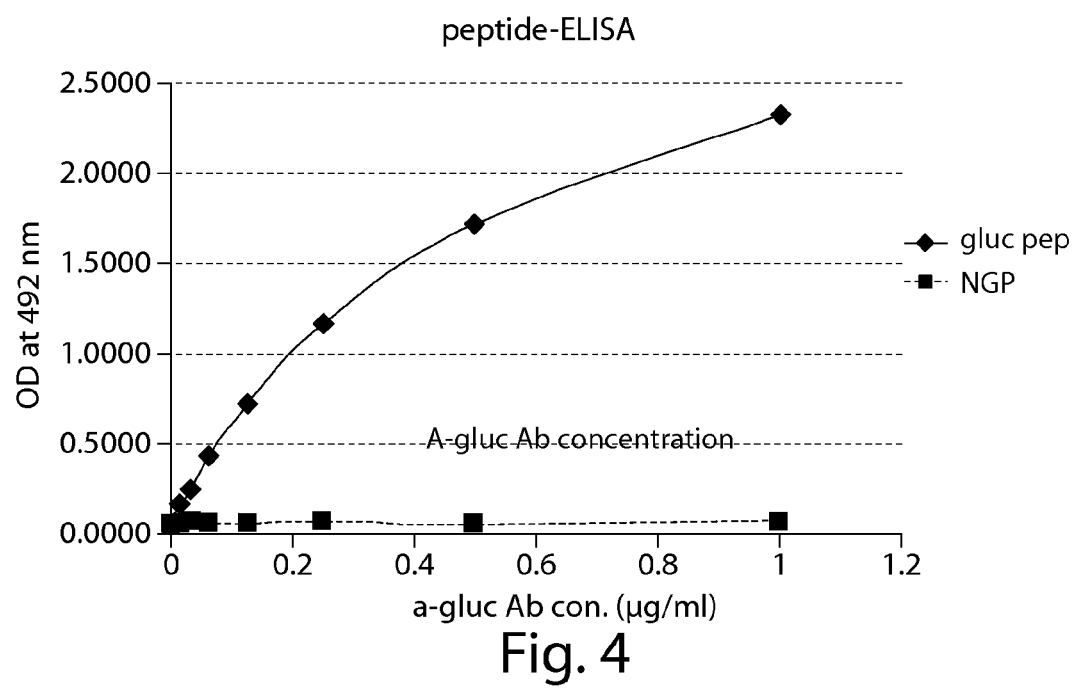
FIG. 4 depicts the titration curve of the glycated+reduced and non-glycated human CD59[37-50] peptides in an ELISA. Coating antigens: glycated+reduced or non-glycated human CD59[37-50] antigens (200 ng/mL solution; 0.1 mL/well=20 ng/well) coated for 1 hour at room temperature. Blocking: All wells were blocked with protein free blocking buffer (0.2 mL for 1 hour). Primary Antibody: rabbit anti-glucytollysine mAb for 1 hr at room temperature, Ab diluent was 10% protein free blocking buffer. Detection Antibody: goat anti-rabbit HRP-tagged polyclonal IgG (Bethyl) 1:10000 1 hour at room temperature, Ab diluent was 10% protein-free blocking buffer. "gluc pep"=glycated and reduced human CD59[37-50]; "NGP"=non-glycated human CD59[37-50] peptide.
Figure 5:
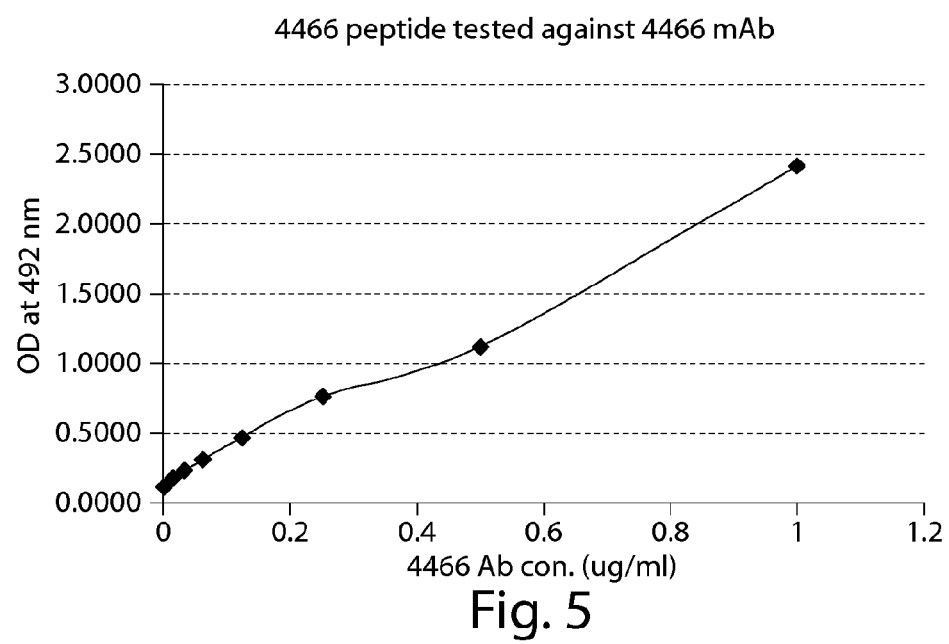
FIG. 5 depicts the titration curve of the human CD59[44-66] antigen in an ELISA. Coating Antigens: human CD59 [44-66] antigen (200 ng/mL solution; 0.1 mL/well=20 ng/well) coated for 1 hour at room temperature. Blocking: All wells were blocked with protein free blocking buffer (0.2 mL for 1 hour). Primary Antibody: 4466-10A7 mouse mAb (mouse anti-human CD59[44-66] mAb) (4.2 mg/mL) for 1 hour at room temperature, Ab diluent was 10% protein free blocking buffer. Detection Antibody: goat anti-mouse HRP-tagged IgG (Caltec) 1:1000 1 hour at room temperature, Ab diluent was 10% protein free blocking buffer.
Figure 6:
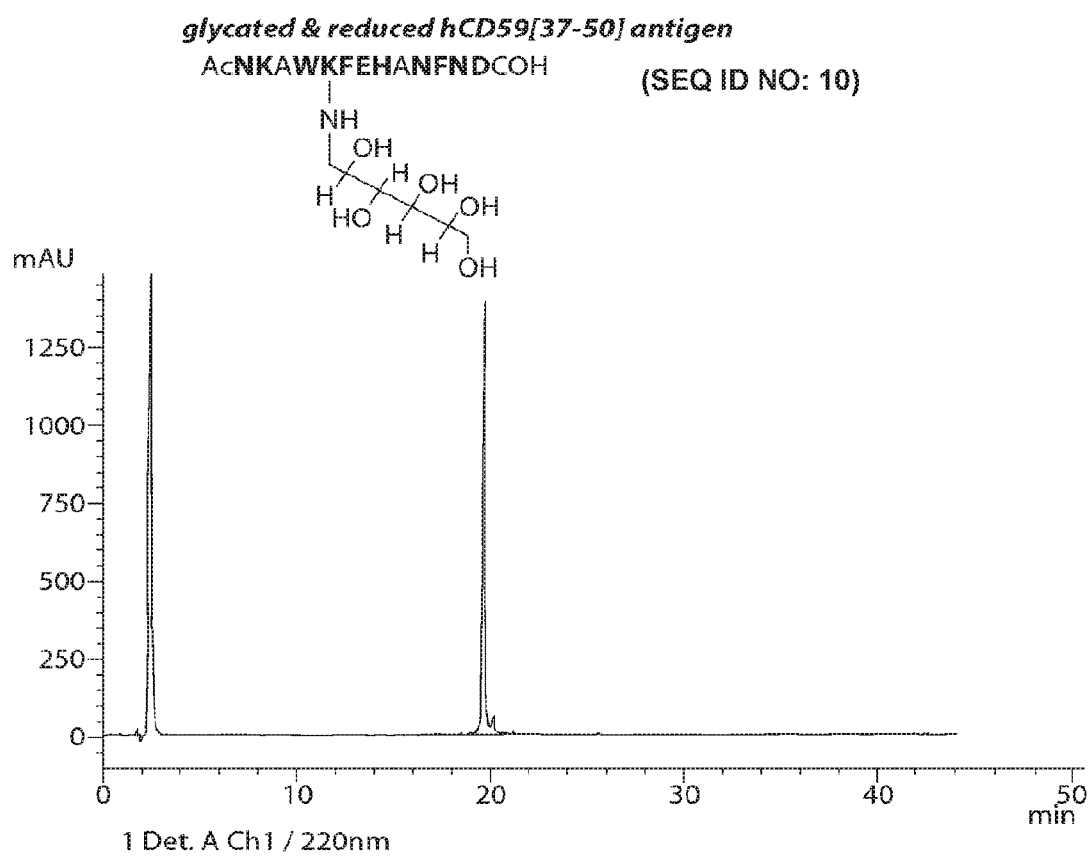
FIG. 6 depicts a HPLC trace for the glycated and reduced human CD59[37-50] antigen. Conditions: 0.20 mg in 10 µL AcOH+40 µL MeCN/TFA/H$_2$O degassed; Injection Volume: 5 µL; Gradient: 5-55% in 50 min.; Column: Vydac C18, 218TP54 (4.6 mm i.d., 250 mL); Buffer: A: 0.05% TFA in H$_2$O; B: 0.05% TFA in MeCN; Flow: 1 mL/min.
Figure 7:
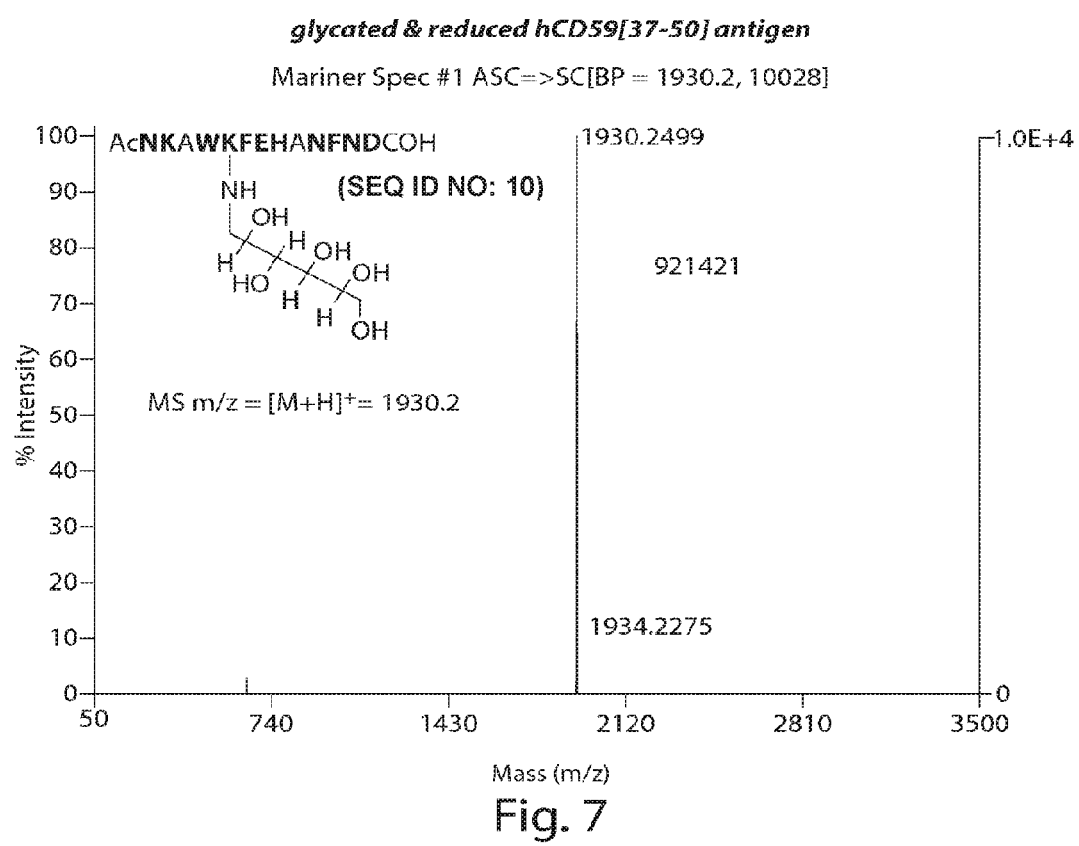
FIG. 7 depicts an electrospray ionization mass spectrum m/z=1930.2 [M+H]$^+$ molecular ion peak associated with glycated and reduced human CD59[37-50] antigen.
Figure 8:
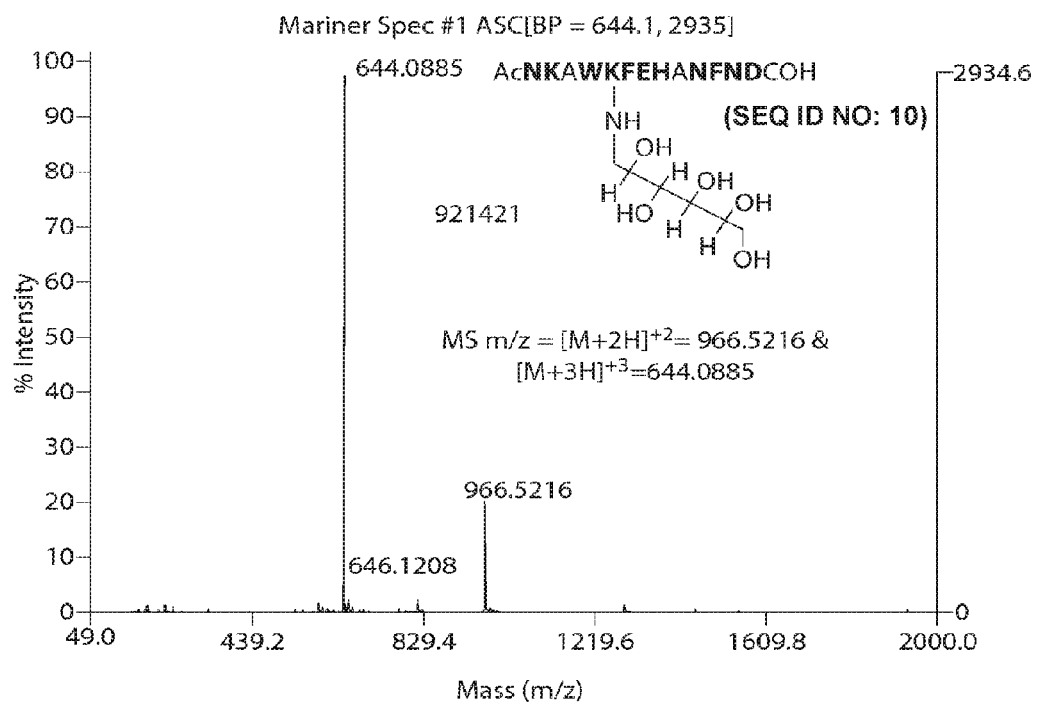
FIG. 8 depicts an electrospray ionization mass spectrum m/z=966.52 and 644.09 for the respective [M+2H]$^{+2}$.

Stepwise manual solid phase peptide synthesis: The peptide was prepared using $N^\alpha$-Fmoc protected amino acids and 2-chlorotrityl-Cys(S-Trt) preloaded resin. Side chain protection included: Asn(Trt), Asp(OtBu), Glu(OtBu), His($N^{im}$-Trt), Lys($N^\epsilon$-Boc) and Trp($N^{im}$-Boc). The preloaded resin was suspended in DCM for 45 min, then washed 3× with DMF and treated with the $N^\alpha$-Fmoc-aa-OH (3 eq.), HCTU (3 eq.) and NMM (5 eq.) for 4 hr at room temperature. The completion of the coupling reaction was monitored by Kaiser Test (E. Kaiser et al., *Anal. Biochem.*, 1970, 34, 595). The resin was drained and washed with DMF. Fmoc deprotection was carried out by treating the resin-bound peptide with 20% piperidine in DMF (v/v) for 1×5 min then 1×20 min. The N-terminus acetylation of the N-terminus was accomplished by exposing the resin-bound peptide to a mixture of acetylimidazole in DCM (4 eq) for 45 min. Simultaneous deprotection of side chains and cleavage of peptide from resin was accomplished in a solution TFA:Anisole:H$_2$O:TIPS:DODT (85:5:5:2.5:2.5 v/v) for 2 h. The filtrate was concentrated under reduced pressure and the resulting residue was precipitated in cold ether to yield the crude solid product. The product was purified by HPLC with a LC-60 Luna Prep $C_{18}$ column, 10 µm, 60×300 mm, using a linear gradient of 10-35% A in B in 50 min, where A=0.05% TFA in acetonitrile and B=0.05% TFA in water) at a flow rate=100 mL/min. The desired product was obtained at purity>95%. MS$^+$(ESI) m/z 965.8 ([M+2H]$^+$/2), calcd: 965.4 confirmed. See FIGS. 7 and 8.

Example 4

Synthesis of Ac-{Ala$^{39,45}$,Lys$^{38}$($N^\epsilon$-ivDde), Cys$^{50}$}hCD59(37-50) (4)

Peptide 4 was synthesized by solid-phase method using Fmoc/tBu Chemistry on an automated (Applied Biosystems, Model 431A) synthesizer. A chlorotrityl resin, preloaded with side chain protected (Trityl) cysteine was used. The activation was performed with HBTU/HOBt/DIEA. Following the assembly of the peptide, the resin was cleaved and deprotected with reagent K (82.5% TFA, 5% Phenol, 5% water and 2.5% ethanedithiol). Purification was performed on a Waters delta-prep system equipped with a Delta-Pak C-18 column. Buffer A consisted of 0.1% TFA in Water and B was 0.1% TFA in Acetonitrile. The column was eluted at a flow rate of 40 ml/min with a linear gradient of 35% to 75% in 20 minutes. Peptide 4 was obtained in >95% purity. RT=8.76 min (10% to 70% in 25 min); MS$^+$(ESI) m/z 986.8 ([M+2H]$^+$/2), calcd: 986.5. The amino acid analysis gave the following (calcd.): Ala 2.4 (2); Asp 4.0 (4); Glu 1.2 (1); His 1.2 (1); Lys 1.8 (2); Phe 2.0 (2).

Example 5

Synthesis of Ac-{Ala$^{39,45}$,Lys$^{38}$($N^\epsilon$-ivDde),Lys$^{41}$ [$N^\epsilon$-(1-deoxy-D-glucitol-1-yl)],Cys$^{50}$} (SEQ ID NO: 22) hCD59(37-50) (5)

Glycation of Lys$^{41}$ in solution: To a solution of peptide 4 in DMF/10% AcOH (5 mg in 500 uL, 0.5 mM), is added 10 mg of D-glucose (final concentration=0.1M) and 2.5 mg of NaBH$_3$CN (final concentration=75 mM). and the reaction is maintained under agitation at RT for 4 days. Then the solution is lyophilized and the product was purified by HPLC-MS, with a X-Terra Prep MSC$_{18}$ column, 5 μm, 30*100 mm, using gradient eluting solvents: 0.1% AcOH in acetonitrile:0.1% AcOH in water (5 to 50% of ACN in 30 min) to give the desired product in high purity (>95%) (Yield=70%). RT=13.45 min (0% to 50% in 25 min); MS$^+$(ESI) m/z 1068.9 ([M+2H]$^+$/2), calcd: 1068.5.

Example 6

Alternative Synthesis of Ac-{Ala$^{39,45}$,Lys$^{41}$[N$^\epsilon$-(1-deoxy-D-glucitol-1-yl)],Cys$^{50}$}hCD59(37-50) (3)

Deprotection of Lys$^{38}$:

To a solution of peptide (5) in MeOH 5% EDT (0.5 mg in 500 uL, 0.5 mM), is added 10 μL of hydrazine hydrate (2%, 0.4M) and the reaction is maintained under agitation at RT for 2 h. Then the solution is neutralized with acetic acid and lyophilized in a large excess of water (5 ml) (crude purity at 214 nm=70%). It was coeluted with the peptide 3 issued from the building block strategy, and had an identical LC/MS profile.

Example 7

Synthesis of Ac-{Asn$^{37,46,48}$,Lys$^{38}$(N$^\epsilon$-Boc),Ala$^{39,45}$, Trp$^{40}$(N$^{in}$-Boc),Lys$^{41}$(N$^\epsilon$-ivDde),Glu$^{43}$(OtBu), His$^{44}$ (N$^{in}$-Trt),Asp$^{49}$(OtBu),Cys$^{50}$(Trt)} (SEQ ID NO: 23) hCD59-(37-50)-2-Cl trityl resin (6)

The glycation of a partially protected resin-bound peptide was carried out following the protocol described in method I above. The only changes were the incorporation of N$^\alpha$-Fmoc-Lys(N$^\epsilon$-ivDde)-OH in position 41 instead of N$^\alpha$-Fmoc-Lys (N$^\epsilon$-Boc)-OH used in Method I and the deprotection of Fmoc group from the N-terminal N$^\alpha$-Fmoc-Lys(N$^\epsilon$-ivDde) was done by treatment with morpholine/DMF (1:1 v/v, 2×15 min), followed by the standard washes. Acidolytic deprotection and cleavage of an aliquot and analysis by LC-ESI-MS validated the anticipated structure that included the ivDde side chain protecting group. RT=10.05 min (10% to 70% in 25 min); MS$^+$(ESI) m/z 986.8 ([M+2H]$^+$/2), calcd: 986.5.

Selective Removal of ivDde from Lys$^{41}$ Side Chain Protection:

The protected resin-bound peptide (1 g, 0.2 mmol) was treated with 2% hydrazine monohydrate in DMF (25 mL) 3×20 min at RT. Then the resin is washed with DMF and DCM (purity at 214 nm of the crude after cleavage of an aliquot of resin=61%); RT=9.72 min (0% to 35% in 25 min); MS$^+$(ESI) m/z 883.7 ([M+2H]$^+$/2), calcd: 883.4.

Selective on-Resin Glycation of Lys$^{41}$:

The partially protected resin-bound peptide (0.02 mmol) was suspended in DMF 5% AcOH. Then, glucose (19 mg, 5 eq) and NaBH$_3$CN (7 mg, 5 eq) are added and the mixture is stirred at RT for 2 days. The completion of glycation was assessed by acidolytic cleavage and deprotection of an aliquot of the resin-bound peptide followed by LC-ESI-MS analysis.

Cleavage, Deprotection and Purification:

These were carried out as described in Method I above to yield the glycated peptide 3 (purity at 214 nm of the crude after cleavage of an aliquot of resin=58%). It was coeluted with the peptide 3 issued from the building block strategy, and had an identical LC/MS profile.

Example 8

Synthesis of Ac-{Ala$^{39,45}$,Cys$^{50}$}hCD59(37-50) (7)

The synthesis of this peptide was carried out in a similar manner as described for glycated peptide (3) and was obtained with the same yield. RT=9.76 min (5% to 35 in 20 min); MS$^+$(ESI) m/z 883.7 ([M+2H]$^+$/2), calcd: 883.4; MALDI MS-MS: The amino acid analysis gave the following (calcd.): Ala 2.4 (2); Asp 4.1 (4); Glu 1.0 (1); His 1.1 (1); Lys 1.9 (1); Phe 2.0 (2).

Example 9

Synthesis of the hCD59[44-66] antigen: Ac-Ala-Cys-Asn-Phe-Asn-Asp-Val-Thr-Thr-Arg-Leu-Arg-Glu-Asn-Glu-Leu-Thr-Tyr-Tyr-Cys-Ala-Ala-Lys-NH$_2$ (SEQ ID NO: 11) (Cys$^2$-Cys$^{20}$-disulfide)(8)

Automated solid phase peptide synthesis: The peptide was prepared using N$^\alpha$-Fmoc protected amino acids starting from Rink Amide ChemMatrix resin (PCAS-BIOMATRIX) and using a Prelude automated peptide synthesizer (Protein Tech), all six channels loaded at 0.5 mmol scale. Side chain protection included: Asn(Trt), Arg(Pbf), Asp(OtBu), Cys (Trt), Glu(OtBu), Lys(N$^\epsilon$-Boc), Thr(tBu) and Tyr(tBu). The starting resin was suspended in DCM for 45 min, then washed 3× with DMF and treated with the N$^\alpha$-Fmoc-aa-OH (3 eq.), HCTU (3 eq.) and NMM (5 eq.) for 4 hr at room temperature. The completion of the coupling reaction was monitored by Kaiser Test (E. Kaiser et al., *Anal. Biochem.*, 1970, 34, 595). The resin was drained and washed with DMF. Fmoc deprotection was carried out by treating the resin-bound peptide with 20% piperidine in DMF (v/v) for 1×5 min then 1×20 min. The N-terminus acetylation of the N-terminus was accomplished by exposing the resin-bound peptide to a mixture of acetylimidazole in DCM (4 eq) for 45 min. Simultaneous deprotection of side chains and cleavage of peptide from resin was accomplished in a solution TFA: Anisole: H$_2$O:TIPS (85:5:5:2.5 v/v) for 2 h. The filtrate was concentrated under reduced pressure and the resulting residue was precipitated in cold ether to yield the crude solid product. The linear peptide was converted to the cyclic disulfide by the use of polymer bound oxidizing agent CLEAR-OX™ (Peptides International, Inc.), according to published procedures [K. Darlak, D. W. Long, A. Czerwinski, M. Darlak, F. Valenzuela, A. F. Spatola, and G. Barany, J. Peptide Res., 63, 303-312 (2004)]. The product was purified by HPLC with a LC-60 Luna Prep C$_{18}$ column, 10 μm, 60×300 mm, using a linear gradient of 10-35% A in B in 50 min, where A=0.05% TFA in acetonitrile and B=0.05% TFA in water) at a flow rate=100 mL/min. The desired product was obtained at purity>93%. MS$^+$(ESI) m/z 2733.26 ([M+H]$^+$), calcd: 2733.4 confirmed.

Example 10

Synthesis of a Hybrid Peptide Surrogate of Glycated and Reduced hCD59

Equimolar amounts of Ac-Ala-Cys-Asn-Phe-Asn-Asp-Val-Thr-Thr-Arg-Leu-Arg-Glu-Asn-Glu-Leu-Thr-Tyr-Tyr-Cys-Ala-Ala-Lys-NH$_2$ (Cys$^2$-Cys$^{20}$-disulfide) (SEQ ID NO: 11) (8) and MAL-dPEG$_{24}$-NHS ester [Mol. Wt.: 1394.55; single compound dPEG Spacer is 82 atoms and 95.2 Å; Quanta Biodesign] were dissolved in DMSO. Triethylamine was added portion wise to reach the pH to 7.0 and the reaction mixture was stirred at room temperature for 1 hour. Analytical HPLC monitoring indicated the completion of reaction. To the above reaction mixture was then added one equivalent of Ac-Asn-Lys-Ala-Trp-Lys[N$^\epsilon$-(1-deoxy-D-glucitol-1-yl)]-Phe-Glu-His-Ala-Asn-Phe-Asn-Asp-Cys-OH (SEQ ID NO: 10) (3) and stirring was continued for one hour. Analytical HPLC monitoring indicated the disappearance of the reactants and formation of new peak. The product was purified by HPLC with a LC-60 Luna Prep 018 column, 10 μm, 60×300 mm, using isocratic conditions to load compound (5% B for 10 min, then 15% for 5 min), then a linear gradient of 15-45% A in B in 60 min, where A=0.05% TFA in acetonitrile and B=0.05% TFA in water) at a flow rate=100 mL/min. The desired product was obtained at purity >97%. The amino acid analysis gave the following results (calcd.): Ala 5.2 (5); Arg 1.8 (2); Asp 8.1 (8); Glu 3.2 (3); His 0.82 (1); Leu(1.9 (2); Lys 2.1 (2); Phe 3.0 (3); Thr 2.9 (3); Tyr 2.0 (2); Val 1.0 (1). See FIG. 21.

Example 11

Purification and Characterization of Urine CD59 by Western Blotting

CD59 from 400 ml of normal human urine was immunopurified over a BRIC-229 antibody column and concentrated by lyophilyzation. The protein concentration was determined by BCA assay (Thermo Scientific) and 2 and 4 micrograms of purified urine CD59 was loaded on 15% SDS-PAGE gel followed by blotting onto PVDF membrane. The blot was removed and quickly dipped into a 50 ml solution of 10 mM sodium borohydride freshly prepared in PBS and allowed to shake for 1 hr. The blot was then washed three times with water and stained with SYPRO Ruby Protein Blot Stain (Invitrogen) following the protocol of manufacturer. The staining was documented on a regular UV Transilluminator. For control, a similar membrane, not reduced with sodium borohydride was used. The reversible Sypro ruby stain was washed away with three washings in TBST (10 mM tris buffered saline containing 0.05% Tween-20, pH 7.4) for 5 min each and the free sites on the membrane were blocked with 3% milk prepared in TBST. The membranes were first exposed to donkey anti-rabbit labeled with IRDye 800 from Rockland Inc at a dilution of 1:1000 to make sure that we are not getting any signal form secondary antibody and then the blots were exposed to rabbit monoclonal at a concentration of 1 μg/ml for 2 hours followed by the same secondary antibody. The signals were documented on Odyssey scanner from Licor.

Example 12

Characterization of Rabbit mAbs by ELISA

Preparation of glycated BSA: An 80 mg/ml solution of BSA was prepared in phosphate buffer saline containing glucose and sodium cyanoborohydride to a final concentration of 400 mM and 150 mM respectively and incubated at 37 deg Celsius. After 22 days the glycated BSA was passed over a desalting column and the protein concentration was adjusted to 50 mg/ml. This preparation was stored frozen at −80 deg Celsius till further use. For control, a similar preparation not carrying any glucose or sodium cyanoborohydride was used.

ELISA: ELISA plates (Maxisorp; Nunc) were coated with 100 μl/well of 6 μg/ml solution of glycated BSA prepared in 0.05 mM carbonate-bicarbonate buffer pH 9.6. After subsequent washing plates were blocked with protein free T20 blocking buffer (Thermo Scientific). For titer determination purified anti-glucitolysine rabbit monoclonal antibody was diluted to a working concentration of 40 μg/ml in PBST containing 10% protein free blocking agent (vol/vol) and then serially diluted on the plate. This was allowed to incubate at room temperature for 2 hrs and then washed 4-times with PBST. HRPO conjugated goat anti rabbit IgG (H+L) was diluted 1:1000 in PBST containing 10% protein free blocking agent and 100 ml of this was added to each well and allowed to incubate at room temperature. After 1 hr the plate was washed 4-times with PBST and developed by addition of Sigmafast OPD (Sigma-Aldrich, St Louis). For control, preserum diluted to a working concentration of 1:100 was used. Other controls were wells not coated with glycated BSA and coated wells probed with anti-rabbit antibody.

Competition ELISA: Plates were coated with glycated-BSA as described above. Glycated or non-glycated peptides was diluted to a working concentration of 2 μg/ml in PBST containing 10% protein free blocking agent and then further diluted serially on ELISA plate. To this a rabbit monoclonal antibody 10 μg/ml was added giving a final concentration of 5 μg/ml. The plates were incubated for 2 hrs at room temperature and then further processed as described above.

Example 13

Capture, Detection, and Quantification of the Surrogate Compound

Reagents: Protein Free T20 (PBS) Blocking Buffer (Thermo Scientific catalog #37573); IMMULON 4HBX plates (Thermo Electron Corporation catalog #3855); Goat Anti Rabbit IgG HRP (Bethyl Laboratories Inc. catalog #A120-201P); 4466 (10A7; mouse mAb) (custom made by Genscript; Lot #A29090242); Glucocytolysine Ab (Clone 42; Rb-mAb; purified by ourselves); Sigma Fast OPD (Sigma catalog #P9187-50SET); and 10% v/v Sulfuric acid (VWR catalog #BDH3258-4).

Protocol: 4466 (mouse mAb) and anti glucocytolysine Ab (Rb mAb) SW ELISA with Hybrid peptide:

1. Hybrid peptide surrogate of glycated and reduced hCD59 is usually diluted (with 3% protein-free blocking buffer in PBST)/10 mM EDTA/1% NP40) to 25 ng/mL; subsequently, 2-fold serial dilutions are made on the plate.

2. 4466 (10A7-3 μg/mL*) coated and already blocked (with protein-free blocking buffer) plates (Immulon 4HBX) are kept at −20° C. After plating the hybrid peptide, plate is incubated for 1 hour at room temperature while shaking.

3. The plate is then washed thoroughly four times with PBST.

4. The plate is then incubated with 0.7 μg/mL*anti glucocytolysine Ab (in 10% protein-free blocking buffer in PBST) for 2 hours at room temperature while shaking.

5. Repeat step 3.

6. The plate is now incubated with goat anti rabbit (Bethyl) HRP (1:5000) Ab (in 10% protein-free blocking buffer in PBST) for one hour at room temperature while shaking.

7. Repeat step 3.

8. 100 μL of freshly prepared Sigma OPD solution is added onto the plate and the plate is allowed to develop for 7 minutes at 37° C. and thereafter the reaction is stopped with 10% v/v H$_2$SO$_4$ (100 μL/well). The plate is read with the ELISA reader at 492 nm.

* The 4466-10A7 coating concentration and the anti-glucocytolysine Ab concentration need to be reestablished for new batches of Antibodies.

The Serum Dilution Buffer was a 3% protein-free blocking buffer in PBST/10 mM EDTA/1% NP40.

Example 14

A [K173(N$^\epsilon$-lipoyl)]PDC-E$_2$-Surrogate as a Standard and Calibrator for Diagnostic Testing to Assess Levels of Anti-Mitochondrial Antibodies (AMA) in Primary Biliary Cirrhosis (PBC)

Lipoylated enzymes such as the E$_2$ component of mitochondrial pyruvate dehydrogenase complex (PDC-E$_2$) are targets for autoreactive immune response in primary biliary cirrhosis (PBC). The lipoic acid binding domain together with the acylated $K^{173}$ forms the immunodominant autoantigen in PBC. Moreover, acylation by xenobiotics that are structurally related to lipoic acid on the $\epsilon$-$NH_2$ in $K^{173}$, which is part of a key structural and functional motif in the inner lipoyl domain of PDC-$E_2$, represents a mechanism for the breakdown of tolerance to lipoic acid-carrying autoantigens in PBC. Detection and monitoring treatment efficacy will be markedly helped by a diagnostic tool that will help in quantization of the routinely conducted ELISA assay.

Design Strategy for the [$K^{173}N^\epsilon$-Lipoyl]PDC-$E_2$-Surrogate

```
                                                      (SEQ ID NO: 12)
  -1 mwrvcarraq nvapwaglea rwtalqevpg tprvtsrsgp aparrnsvtt gyggvralcg -86/1 wtpssgatpr nrlllqllgs pgrryyslpp hqkvplpsls ptmqagtiar wekkegdkin 35 egdliaevet dkatvgfesl eecymakilv aegtrdvpig aiicitvgkp edieafknyt 95 ldssaaptpq aapaptpaat aspptpsaqa pgssypphmq vllpalsptm tmgtvqrwek 155 kvgeklsegd llaeietdka tigfevqeeq ylakilvpeg trdvplgtpl ciivekeadi 215 safadyrpte vtdlkpqvpp ptpppvaavp ptpqplaptp sapcpatpag pkgrvfvspl 275 akklavekgi dltqvkgtgp dgritkkdid sfvpskvapa paavvpptgp gmapvptgvf 335 tdipisnirr viaqrlmqsk qtiphyylsi dvnmgevllv rkelnkileg rskisvndfi 395 ikasalaclk vpeansswmd tvirqnhvvd vsvaystpag litpivfnah ikgvetiand 455 vvslatkare gklqphefqg qtftisnlqm fqiknfsaii nppqacilai gasedklvpa 515 dnekgfdvas mmsvtlscdh rvvdgavgaq wlaefrkyle kpitmll
```

(SEQ ID NO: 13)
AcAEIETDK(N$^\epsilon$-Lipoyl)ATIGFEVQEEGK (SEQ ID NO: 14)
HS(CH$_2$)$_3$CO-
GTFTISNLGMFGIKNFSAIINPPQANH$_2$ Spacer:

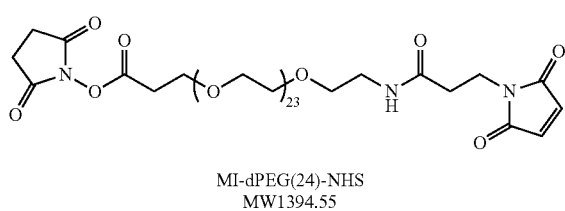

MI-dPEG(24)-NHS
MW1394.55

Resulting [$K^{173}N^\epsilon$-Lipoyl]PDC-$E_2$-Surrogate:

Example 15

A [$S^{51}$-Phospho]eIF2α-Surrogate as a Standard and Calibrator for Diagnostic Test to Assess Susceptibility to Drugs Targeting Translation Initiation for Treatment of Cancer and Other Proliferative Diseases Phosphorylation of eIF2α, a subunit of the eukaryotic initiation factor 2, by eIF2α kinases is an important inhibitory step in the translation mechanism. As such, measuring changes in the phosphorylation level of eIF2α in target tissues following treatment with drugs targeting translation initiation could serve as a test for assessing the sensitivity to and efficacy of treatment of cancer and other proliferative diseases. In the absence of a scalable, reproducible and easily accessible source of [$S^{51}$-Phospho]eIF2α that can serve as a standard and calibrator in a [$S^{51}$-Phospho]eIF2α-based diagnostic assay a synthetic, easily accessible and scalable [$S^{51}$-Phospho]eIF2α-surrogate is an important component in such an assay.

The [$S^{51}$-Phospho]eIF2α-surrogate is a hybrid construct that includes two non-overlapping antigenic sequences derived from human [$S^{51}$-Phospho]eIF2α(41-60) and the carboxyl-terminal sequence of human [$C^{278}$]eIF2α(278-308) that are linked by a heterobifunctional polyethyleneoxide linker MI-(CH$_2$)$_2$CONH(CH$_2$CH$_2$O)$_{24}$(CH$_2$)$_2$CO—NHS, where MI and NHS are a maleimido and an N-hydroxysuccinimido moieties. The MI binds specifically to the side chain of [$C^{278}$] in the carboxyl-terminal fragment and the NHS binds specifically to $\epsilon$-$NH_2$ on $K^\alpha$ in the $S^{51}$-containing fragment of eIF2α. See FIG. 22.

AcAEIETDK(N$^\epsilon$-Lipoyl)ATIGFEVQEEGK
(SEQ ID NO: 13)

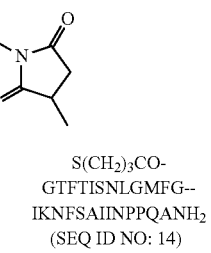

S(CH$_2$)$_3$CO-
GTFTISNLGMFG--
IKNFSAIINPPQANH$_2$
(SEQ ID NO: 14)

Example 16

Use of a Hybrid Peptide Surrogate of Glycated and Reduced hCD59 (GCD59 Surrogate) as a Synthetic Peptide Standard in Determining Levels of GCD59 in Serum Samples of Diabetic and Non-Diabetic Human Subjects The hybrid peptide surrogate of glycated and reduced hCD59 (GCD59 Surrogate) of Example 10 was employed as a synthetic peptide (SP) standard. Solutions of the SP at different concentrations (0.125, 0.25, 0.5, 1, 2, and 3 ng/ml) were prepared. The optical density (OD) values of the SP solutions ($OD_{SP}$) and of a blank solution ($OD_{blank}$) were determined in a Sandwich ELISA assay using 4466 (10A7; mouse mAb) as the capture antibody and anti-glucocytolysine Ab (Rb mAb) as the detection antibody (Table 1). A calibration curve was obtained by plotting the net optical density values ($OD_{SP}$–$OD_{blank}$) against the concentrations of the SP solutions (FIG. 23A). The calibration curve may be linearly fitted (y=0.3198x+0.0369, $R^2$=0.9967).

TABLE 1

Optical density (OD) values of solutions of the synthetic peptide (SP) standard

| [SP] (ng/ml) | Mean $OD_{SP}$ | Mean ($OD_{SP}$ - $OD_{blank}$) |
|---|---|---|
| 3 | 1.4 | 1.0 |
| 2 | 1.1 | 0.7 |
| 1 | 0.7 | 0.4 |
| 0.5 | 0.6 | 0.2 |
| 0.25 | 0.5 | 0.1 |
| 0.125 | 0.5 | 0.1 |
| 0 | 0.4 | 0.0 |

Using the calibration curve in FIG. 23A, GCD59 in serum samples can be quantified in standard peptide units (SPUs). Net OD values of serum samples of diabetic (D1-D3) and non-diabetic (N1-N3) human subjects were determined as described above (Table 2). The levels of GCD59 in SPU were obtained by using the calibration curve (FIG. 23B and Table 2).

TABLE 2

Quantification of GCD59 in human serum samples using the calibration curve in FIG. 23A

| Experimental code (SPU) | Mean ($OD_{SP}$ - $OD_{blank}$) | SD | GCD59 level (SPU) |
|---|---|---|---|
| D1 | 1.1 | 0.14 | 3.2 |
| D2 | 0.9 | 0.04 | 2.6 |
| D3 | 0.6 | 0.02 | 1.7 |
| N1 | 0.2 | 0.01 | 0.6 |
| N2 | 0.1 | 0.04 | 0.3 |
| N3 | 0.1 | 0.04 | 0.3 |

Quantification of GCD59 in SPU were similarly performed in more serum samples of diabetic (D4-D11) and non-diabetic (N4-N10) human subjects (FIG. 25). On average, the serum samples of diabetic human subjects show higher levels of GCD59 (1.9±1.0 SPU) than samples of non-diabetic human subjects (0.5±0.3 SPU). This result suggests that a test for GCD59 levels may be performed to diagnose a human subject as having a diabetic condition and/or to screen for human subjects with a diabetic condition in a population of human subjects.

To compare with the results of the GCD59 test in diagnosing and/or screening for subjects with a diabetic condition, HbA1c levels in blood samples of human subjects N1-N10 and D1-D11 were also determined (Table 3). Assays that quantify HbA1c in blood samples are used to monitor glycemic load and response to treatment in diabetic subjects. In an HbA1c test, a blood sample of a subject is drawn, and the percentage of HbA1c in the blood sample is determined. An HbA1c level less than 6.5 (i.e., the percentage of HbA1c in the blood sample is less than 6.5%) is considered normal in human. An HbA1c level of greater than 6.5 indicates a diabetic condition. Table 3 illustrates that, on average, blood samples of diabetic human subjects show higher HbA1c levels (7.8±1.6) than samples of non-diabetic human subjects (5.0±0.7). The above results indicate that levels of GCD59 in the serum of diabetic and non-diabetic human subjects correlate to HbA1c levels in the blood of these subjects.

TABLE 3

HbA1c and Fasting Serum Glucose (FSG) levels in samples of non-diabetic (N1-N10) and diabetic (D1-D11) human subjects

| Experimental code | HbA1c level | Fasting Serum Glucose (FSG) level (mg/dl) |
|---|---|---|
| N1 | 4.8 | 92 |
| N2 | 4.5 | 78 |
| N3 | 4.7 | 94 |
| N4 | 4.2 | 77 |
| N5 | 4.7 | 90 |
| N6 | 5.3 | 105 |
| N7 | 5.5 | 79 |
| N8 | 6.1 | 117 |
| N9 | 4.5 | 86 |
| N10 | 6 | 107 |
| D1 | 8 | 365 |
| D2 | 10.5 | 213 |
| D3 | 8.8 | 194 |
| D4 | 5.8 | 158 |
| D5 | 7.7 | 91 |
| D6 | 5.2 | 100 |
| D7 | 6.5 | 109 |
| D8 | 9.5 | 87 |
| D9 | 8.9 | 214 |
| D10 | 7.2 | 141 |
| D11 | 7.6 | 248 |

A Fasting Serum Glucose (FSG) test measures the amount of glucose in a serum sample obtained from a subject after the subject has fasted for at least 6-8 hours. Typically, the FSG level of a normal human subject is less than about 110 milligrams per deciliter (mg/dl). An FSG level between about 110 mg/dl and about 126 mg/dl indicates impaired glucose tolerance, and an FSG level of more than about 126 mg/dl indicates a diabetic condition. Here, FSG levels of non-diabetic (N1-N10) and diabetic (D1-D11) human subjects were determined (Table 3 and FIG. 24). Samples of diabetic human subjects show an average FSG level of 174±84 mg/dl, higher than the average FSG level of 93±14 mg/dl in samples of non-diabetic human subjects. These results indicate that levels of GCD59 in the serum of diabetic and non-diabetic human subjects correlate to levels of fasting serum glucose in these subjects.

Example 17

Use of the Rabbit Anti-Glucytollysine mAb to Detect the Reduced Amadori-Modified CD59-Derived Peptide (Reduced AP)

ELISA experiments were performed to investigate the recognition of an Amadori-modified CD59-derived peptide (AP), before and after reduction, by the rabbit anti-glucytollysine mAb. The structure of the AP is shown in FIG. 26A.

Prior to the ELISA experiment, the AP was reduced with NaBH$_4$ outside the plate. A solution of Amadori peptide (AP) (1 mg/ml, 50 µl) was reduced with 2.5 µl of freshly prepared 1 M solution of NaBH$_4$ (38 mg of NaBH$_4$ powder dissolved in 1 ml of water; final concentration was 50 mM) for 1 hr at room temperature. After 1 hr, the reaction was quenched with 1 ml of 1% acetic acid (the peptide concentration was now 5 µg/ml). Finally, to achieve a concentration of 200 ng/ml, 800 µl of the reduced and quenched Amadori peptide was added in 20 ml of water and vortexed well. 100 µl of this solution was added to the designated wells in a 96-well ELISA plate. Peptide concentration on the plate was 20 ng/well. The subsequent steps of peptide ELISA, e.g, blocking, incubation with primary Ab followed by secondary Ab, and detection, were as described above or known in the art.

The AP was also reduced with NaBH$_4$ on the plate prior to the ELISA experiment. The Amadori peptide was plated at 20 ng/well. The designated wells to be reduced were incubated with 100 µl of 10 mM freshly prepared NaBH$_4$ solution prepared from 500 µl of 1 M NaBH$_4$ solution that was added to 50 ml of water and mixed well for 1 hr at room temperature under shaking. After 1 hr, the plate was washed with 1×PBS-0.05% T-20 and followed by the standard steps employed for coating the ELISA plate with peptide. These steps include blocking, incubation with primary Ab followed by secondary Ab, and detection.

The resulting reduced AP was then assayed in an ELISA using the rabbit anti-glucytollysine mAb. The ELISA results show that, irrespective of the reducing procedure, i.e., off-plate or on-plate, the rabbit anti-glucytollysine mAb recognizes the reduced AP but does not recognize the AP, which is not reduced (FIGS. 26B and 26C).

A glucitollysine-modified CD59-derived peptide (GP) was used in the ELISA experiments as a positive control. The ELISA results, shown in FIGS. 26B and 26C, indicate that the rabbit anti-glucytollysine mAb also recognizes the GP.

Example 18

Synthesis and Characterization of an Amadori Peptide Hybrid (Amadori CD59 Surrogate)

An Amadori peptide hybrid (Amadori CD59 surrogate) was synthesized using methods described above, e.g., in Example 10. The structure of the Amadori peptide hybrid is shown in FIG. 27.

An analytical reverse-phase HPLC was performed to determine the purity of the synthesized Amadori peptide hybrid using a Jupiter C$_{18}$ column (5 µm, 4.6×250 mm) under a gradient of 10-50% MeCN (modified with 0.05% TFA) in water (modified with 0.05% TFA) over 40 min at a flow rate of 1 mL/min. The injection volume was 5 µL. A chromatogram recorded at 220 nm shows that the Amadori peptide hybrid is pure (FIG. 28).

The molecular weight of the Amadori peptide hybrid was measured using deconvoluted mass spectroscopy. The base peak at an m/z of about 5942.3 is assigned to the [M+H]$^+$ molecular ion of the Amadori peptide hybrid.

Example 19

ELISA Assays Using the Rabbit Anti-Glucytollysine mAb (Gluc Ab) and the Anti-CD59 Antibody (4466Ab) in the Recognition of the Amadori Hybrid Peptide (Amadori CD59 Surrogate, hy-AP, or Non-red hy-AP) and the Reduced Amadori Hybrid Peptide (Red hy-AP)

Prior to ELISA, the Amadori hybrid peptide was reduced to yield the reduced Amadori hybrid peptide according to methods described above, e.g., in Example 17. ELISA experiments were performed with both the nonreduced and reduced Amadori hybrid peptides. Two different antibodies, gluc Ab and 4466Ab, were used in the assays. The ELISA results show that 4466Ab recognizes both the nonreduced and reduced Amadori hybrid peptides, while the gluc Ab recognizes the reduced Amadori hybrid peptide but not the nonreduced Amadori hybrid peptide (FIG. 30).

ABBREVIATIONS

AcOH: acetic acid, Boc: tert-Butyloxycarbonyle, Boc$_2$O: Di-tert-butyl dicarbonate, DCM: dichloromethane, DODT: 2,2'-(Ethylenedioxy)diethanethiol; DIEA: N,N diisopropylethyl amine, DMF: dimethylformamide, EDT: ethanedithiol, iPrOH: isopropanol, MeOH: Methanol, NaBH$_3$CN: Sodium cyanoborohydride, pyBOP: Benzotriazol-1-yl-oxytripyrrolidinophosphonium hexafluorophosphate, Rt: retention time, tBu: tert-Butyl, TEA, triethylamine, THF: Tetrahydrofuran, Trt: trityl.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advan- labeles and objects of the invention are not necessarily encompassed by each embodiment of the invention.

APPENDIX

Sequence Listing (SEQ ID NO: 1) WKFEH
The K-glycated pentapeptide fragment of human CD59.

(SEQ ID NO: 2) WKFEH
A non-glycated pentapeptide fragment of human CD59.

(SEQ ID NO: 3) NKAWKFEHANFND
The K-glycated polypeptide fragment of human CD59.

(SEQ ID NO: 4) NKCWKFEHCNFND
A non-glycated polypeptide fragment of human CD59.

APPENDIX-continued

Sequence Listing (SEQ ID NO: 5)
A non-glycated form of the human CD59 polypeptide of 103 amino acid residues.

```
Leu Gln Cys Tyr Asn Cys Pro Asn Pro Thr Ala Asp Cys Lys Thr Ala
1               5                   10                  15
Val Asn Cys Ser Ser Asp Phe Asp Ala Cys Leu Ile Thr Lys Ala Gly
                20                  25                  30
Leu Gln Val Tyr Asn Lys Cys Trp Lys Phe Glu His Cys Asn Phe Asn
            35                  40                  45
Asp Val Thr Thr Arg Leu Arg Glu Asn Glu Leu Thr Tyr Tyr Cys Cys
        50                  55                  60
Lys Lys Asp Leu Cys Asn Phe Asn Glu Gln Leu Glu Asn Gly Gly Thr
65                  70                  75                  80
Ser Leu Ser Glu Lys Thr Val Leu Leu Leu Val Thr Pro Phe Leu Ala
                85                  90                  95
Ala Ala Trp Ser Leu His Pro
            100
```

(SEQ ID NO: 6)
A K41-glycated (X) form of the human CD59 polypeptide of 103 amino acid residues.

```
Leu Gln Cys Tyr Asn Cys Pro Asn Pro Thr Ala Asp Cys Lys Thr Ala
1               5                   10                  15
Val Asn Cys Ser Ser Asp Phe Asp Ala Cys Leu Ile Thr Lys Ala Gly
                20                  25                  30
Leu Gln Val Tyr Asn Lys Cys Trp (X) Phe Glu His Cys Asn Phe Asn
            35                  40                  45
Asp Val Thr Thr Arg Leu Arg Glu Asn Glu Leu Thr Tyr Tyr Cys Cys
        50                  55                  60
Lys Lys Asp Leu Cys Asn Phe Asn Glu Gln Leu Glu Asn Gly Gly Thr
65                  70                  75                  80
Ser Leu Ser Glu Lys Thr Val Leu Leu Leu Val Thr Pro Phe Leu Ala
                85                  90                  95
Ala Ala Trp Ser Leu His Pro
            100
```

(SEQ ID NO: 8)
The full-length nucleic acid sequence of human CD59.

```
ctttagcacc agttggtgta ggagttgaga cctacttcac agtagttctg tggacaatca  60
caatgggaat ccaaggaggg tctgtcctgt tcgggctgct gctcgtcctg gctgtcttct 120
gccattcagg tcatagcctg cagtgctaca actgtcctaa cccaactgct gactgcaaaa 180
cagccgtcaa ttgttcatct gattttgatg cgtgtctcat taccaaagct gggttacaag 240
tgtataacaa gtgttggaag tttgagcatt gcaatttcaa cgacgtcaca acccgcttga 300
gggaaaatga gctaacgtac tactgctgca agaaggacct gtgtaacttt aacgaacagc 360
ttgaaaatgg tgggacatcc ttatcagaga aaacagttct tctgctggtg actccatttc 420
tggcagcagc ctggagcctt catccctaag tcaacaccag gagagcttct cccaaactcc 480
ccgttcctgc gtagtccgct ttctcttgct gccacattct aaaggcttga tattttccaa 540
atggatcctg ttgggaaaga ataaaattag cttgagca                         578
```

What is claimed is:

1. A compound comprising:
   a. a first epitope comprising the amino acid sequence ACN-FNDVTTRLRENELTYYCAAK (SEQ ID NO: 11);
   b. a second epitope comprising the sequence $R^1$-$K^{41}$-$R^2$, wherein
      $R^1$ is absent or a peptide sequence which is identical to or comprises one or more amino acid deletions, insertions, or substitutions relative to a peptide sequence selected from residues 30-40 of human CD59 (SEQ ID NO: 5); and
      $R^2$ is absent or a peptide sequence which is identical to or comprises one or more amino acid deletions, insertions, or substitutions relative to a peptide sequence selected from residues 42-60 of human CD59 (SEQ ID NO: 5);
   c. an optional label, wherein said label is fluoroescent, phosphorescent, chemiluminescent, chromogenic, affinity-based, enzyme based, or radioactive; and
   d. a linker that joins the first epitope to the second epitope, wherein the linker is selected from the group consisting of an aliphatic moiety, a heteroaliphatic moiety, an acyl, and an aryl,
   wherein:
      the aliphatic moiety is cyclic or acyclic, substituted or unsubstituted, and branched or unbranched,
      the heteroaliphatic moiety is cyclic or acyclic, substituted or unsubstituted, and branched or unbranched,
      the acyl is substituted or unsubstituted, and branched or unbranched, and
      the aryl is substituted or unsubstituted, and branched or unbranched;
   wherein each substituent is independently selected from the group consisting of a branched alkyl, an unbranched alkyl, a branched alkenyl, an unbranched alkenyl, a branched alkynyl, an unbranched alkynyl, heterocyclic, —$OR^A$; —C(=O)$R^A$; —$CO_2R^A$; —$SR^A$; —$SOR^A$; —$SO_2R^A$; =O; =N($R^A$); =S; —N($R^A$)$_2$; —NHC(=O)$R^A$; —$NR^A$C(=O)N($R^A$)$_2$; —OC(=O)$R^A$; —OC(=O)$R^A$; —OC(=O)N($R^A$)$_2$; and $NR^A$C(=O)$OR^A$; wherein each occurrence of $R^A$ is independently a hydrogen, an aliphatic moiety, a heteroaliphatic moiety, an acyl moiety; an aryl moiety; a heteroaryl moiety; an alkoxy moiety; aryloxy moiety; an alkylthio moiety; an arylthio moiety; an amino moiety; an alkylamino moiety; a dialkylamino moiety; a heteroaryloxy moiety; or a heteroarylthio moiety; with the proviso that the linker is not a peptide bond.

2. The compound of claim 1, wherein the linker comprises the formula:

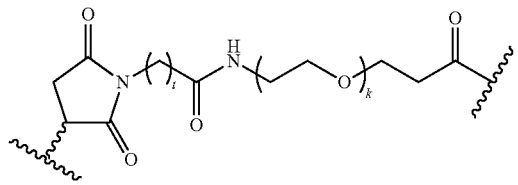

wherein;
   a. t is an integer from 1 to 12, inclusive, and
   b. k is 0 or an integer from 1 to 100, inclusive.

3. The compound of claim 2, wherein the linker comprises the formula:

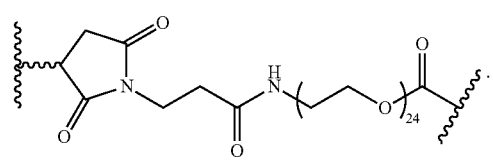

4. The compound of claim 3, wherein the linker is bound to said first epitope and said second epitope through one or more covalent bonds with one or more side chains of one or more amino acids.

5. The compound of claim 4, wherein said one or more covalent bonds are formed with one or more amino acids independently selected from the group consisting of cysteine, lysine, serine, threonine, tyrosine, histidine, arginine, tryptophan, asparagine, glutamine, aspartic acid and glutamic acid.

6. The compound of claim 5, wherein said second epitope comprises the sequence $N^{37}$KAWKFEHANFNDC$^{50}$ (SEQ ID NO:10).

7. The compound of claim 6, wherein $K^{41}$ is glycated on the ε-amino to form said glycation motif, said glycation motif comprising a moiety selected from the group consisting of:

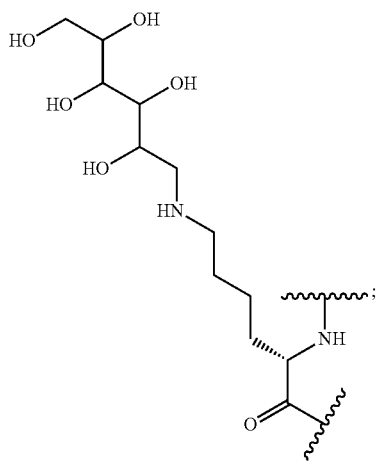

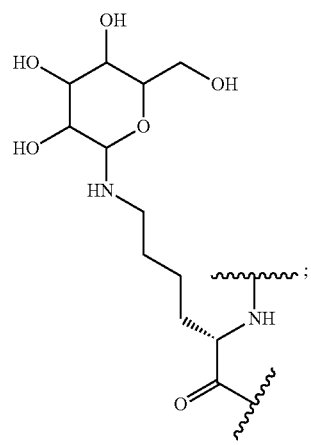

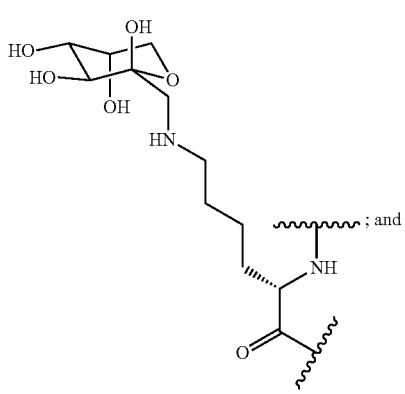

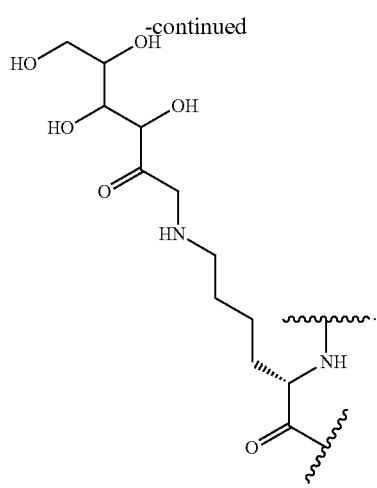

-continued

8. The compound of claim 7, wherein said first epitope comprises a disulfide bond between cysteine residues.

9. The compound of claim 2, wherein said second epitope comprises the sequence $N^{37}KAWKFEHANFNDC^{50}$ (SEQ ID NO:10), and wherein the side chain of the $C^{50}$ residue of said second epitope is joined to the succinimidyl moiety of the linker.

10. The compound of claim 2, wherein the side chain of the C-terminal lysine residue of ACNFNDVTTRLRENELTYY-CAAK (SEQ ID NO: 11) is linked with the linker.

11. A method for detecting in a sample the presence and/or level of $K^{41}$-glycated CD59, said method comprising:
   a. preparing a reference sample comprising a known amount of the compound of claim 8,
   b. obtaining a biological sample from a subject,
   c. measuring the amount of said compound in said reference sample using one or more antibodies,
   d. measuring the amount of $K^{41}$-glycated CD59 in said biological sample using one or more antibodies, and
   e. comparing the amount of said compound in said reference sample to the amount of $K^{41}$-glycated CD59 in said biological sample.

12. The method of claim 11, wherein the step of measuring the amount of said compound in said reference sample is determined by:
   a. contacting a first capture antibody, immobilized to a surface, with said compound, said first capture antibody comprising an antibody that binds specifically to the non-glycated epitope of said compound, wherein said non-glycated epitope comprises:
      (i) the amino acid sequence ACNFNDVTTRLRENEL-TYYCAAK (SEQ ID NO:11), and
      (ii) a disulfide bond between cysteine residues, and
   wherein said antibody is a monoclonal antibody of murine origin,
   b. contacting said compound with a primary detecting antibody, said primary detecting antibody targeting the glycated epitope of said compound, and c. contacting the primary detecting antibody with a secondary detecting/quantifying antibody, said secondary detecting/quantifying antibody targeting said primary detecting antibody.

13. The method of claim 12, wherein said biological sample is reduced prior to measuring the amount of $K^{41}$-glycated CD59 in said biological sample.

14. The method of claim 13, wherein said biological sample is reduced by contacting said biological sample with an effective amount of one or both of sodium cyanoborohydride and sodium borohydride.

15. The method of claim 14, wherein said biological sample is reduced by contacting said biological sample with 10 mM sodium borohydride for an effective length of time.

* * * * *

SEQUENCE LISTING

<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is a glycated Lys

<400> SEQUENCE: 1

Trp Xaa Phe Glu His
1               5

<210> SEQ ID NO 2
<211> LENGTH: 5

```
<212> TYPE: PRT
<213> ORGANISM: Homo sapiens

<400> SEQUENCE: 2

Trp Lys Phe Glu His
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is a glycated Lys

<400> SEQUENCE: 3

Asn Lys Ala Trp Xaa Phe Glu His Ala Asn Phe Asn Asp
1               5                   10

<210> SEQ ID NO 4
<211> LENGTH: 13
<212> TYPE: PRT
<213> ORGANISM: Homo sapiens

<400> SEQUENCE: 4

Asn Lys Cys Trp Lys Phe Glu His Cys Asn Phe Asn Asp
1               5                   10

<210> SEQ ID NO 5
<211> LENGTH: 103
<212> TYPE: PRT
<213> ORGANISM: Homo sapiens

<400> SEQUENCE: 5

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
                20                  25                  30

Leu Gln Val Tyr Asn Lys Cys Trp Lys Phe Glu His Cys Asn Phe Asn
            35                  40                  45

Asp Val Thr Thr Arg Leu Arg Glu Asn Glu Leu Thr Tyr Tyr Cys Cys
        50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Leu Val Thr Pro Phe Leu Ala
                85                  90                  95

Ala Ala Trp Ser Leu His Pro
            100

<210> SEQ ID NO 6
<211> LENGTH: 103
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (41)..(41)
<223> OTHER INFORMATION: Xaa is a glycated Lys

<400> SEQUENCE: 6
```

Leu Gln Cys Tyr Asn Cys Pro Asn Pro Thr Ala Asp Cys Lys Thr Ala
1               5                   10                  15

Val Asn Cys Ser Ser Asp Phe Asp Ala Cys Leu Ile Thr Lys Ala Gly
            20                  25                  30

Leu Gln Val Tyr Asn Lys Cys Trp Xaa Phe Glu His Cys Asn Phe Asn
            35                  40                  45

Asp Val Thr Thr Arg Leu Arg Glu Asn Glu Leu Thr Tyr Tyr Cys Cys
        50                  55                  60

Lys Lys Asp Leu Cys Asn Phe Asn Glu Gln Leu Glu Asn Gly Gly Thr
65                  70                  75                  80

Ser Leu Ser Glu Lys Thr Val Leu Leu Val Thr Pro Phe Leu Ala
                85                  90                  95

Ala Ala Trp Ser Leu His Pro
            100

<210> SEQ ID NO 7
<211> LENGTH: 23
<212> TYPE: PRT
<213> ORGANISM: Homo sapiens

<400> SEQUENCE: 7

His Cys Asn Phe Asn Asp Val Thr Thr Arg Leu Arg Glu Asn Glu Leu
1               5                   10                  15

Thr Tyr Tyr Cys Cys Lys Lys
            20

<210> SEQ ID NO 8
<211> LENGTH: 578
<212> TYPE: DNA
<213> ORGANISM: Homo sapiens

<400> SEQUENCE: 8
ctttagcacc agttggtgta ggagttgaga cctacttcac agtagttctg tggacaatca      60
caatgggaat ccaaggaggg tctgtcctgt tcgggctgct gctcgtcctg gctgtcttct     120
gccattcagg tcatagcctg cagtgctaca actgtcctaa cccaactgct gactgcaaaa     180
cagccgtcaa ttgttcatct gattttgatg cgtgtctcat taccaaagct gggttacaag     240
tgtataacaa gtgttggaag tttgagcatt gcaatttcaa cgacgtcaca acccgcttga     300
gggaaaatga gctaacgtac tactgctgca agaaggacct gtgtaacttt aacgaacagc     360
ttgaaaatgg tgggacatcc ttatcagaga aaacagttct tctgctggtg actccatttc     420
tggcagcagc ctggagcctt catccctaag tcaacaccag agagcttctc ccaaactcc     480 ccgttcctgc gtagtccgct ttctcttgct gccacattct aaaggcttga tattttccaa     540
atggatcctg ttgggaaaga ataaaattag cttgagca                             578

<210> SEQ ID NO 9
<211> LENGTH: 14
<212> TYPE: PRT
<213> ORGANISM: Homo sapiens

<400> SEQUENCE: 9

Asn Lys Cys Trp Lys Phe Glu His Cys Asn Phe Asn Asp Val
1               5                   10

<210> SEQ ID NO 10
<211> LENGTH: 14
<212> TYPE: PRT
<213> ORGANISM: Artificial Sequence

```
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is a glycated Lys

<400> SEQUENCE: 10

Asn Lys Ala Trp Xaa Phe Glu His Ala Asn Phe Asn Asp Cys
1               5                   10

<210> SEQ ID NO 11
<211> LENGTH: 23
<212> TYPE: PRT
<213> ORGANISM: Homo sapiens

<400> SEQUENCE: 11

Ala Cys Asn Phe Asn Asp Val Thr Thr Arg Leu Arg Glu Asn Glu Leu
1               5                   10                  15

Thr Tyr Tyr Cys Ala Ala Lys
            20

<210> SEQ ID NO 12
<211> LENGTH: 647
<212> TYPE: PRT
<213> ORGANISM: Homo sapiens

<400> SEQUENCE: 12

Met Trp Arg Val Cys Ala Arg Arg Ala Gln Asn Val Ala Pro Trp Ala
1               5                   10                  15

Gly Leu Glu Ala Arg Trp Thr Ala Leu Gln Glu Val Pro Gly Thr Pro
            20                  25                  30

Arg Val Thr Ser Arg Ser Gly Pro Ala Pro Ala Arg Arg Asn Ser Val
        35                  40                  45

Thr Thr Gly Tyr Gly Gly Val Arg Ala Leu Cys Gly Trp Thr Pro Ser
    50                  55                  60

Ser Gly Ala Thr Pro Arg Asn Arg Leu Leu Leu Gln Leu Leu Gly Ser
65                  70                  75                  80

Pro Gly Arg Arg Tyr Tyr Ser Leu Pro Pro His Gln Lys Val Pro Leu
                85                  90                  95

Pro Ser Leu Ser Pro Thr Met Gln Ala Gly Thr Ile Ala Arg Trp Glu
            100                 105                 110

Lys Lys Glu Gly Asp Lys Ile Asn Glu Gly Asp Leu Ile Ala Glu Val
        115                 120                 125

Glu Thr Asp Lys Ala Thr Val Gly Phe Glu Ser Leu Glu Glu Cys Tyr
    130                 135                 140

Met Ala Lys Ile Leu Val Ala Glu Gly Thr Arg Asp Val Pro Ile Gly
145                 150                 155                 160

Ala Ile Ile Cys Ile Thr Val Gly Lys Pro Glu Asp Ile Glu Ala Phe
                165                 170                 175

Lys Asn Tyr Thr Leu Asp Ser Ser Ala Ala Pro Thr Pro Gln Ala Ala
            180                 185                 190

Pro Ala Pro Thr Pro Ala Ala Thr Ala Ser Pro Pro Thr Pro Ser Ala
        195                 200                 205

Gln Ala Pro Gly Ser Ser Tyr Pro Pro His Met Gln Val Leu Leu Pro
    210                 215                 220

Ala Leu Ser Pro Thr Met Thr Met Gly Thr Val Gln Arg Trp Glu Lys
225                 230                 235                 240
```

-continued

```
Lys Val Gly Glu Lys Leu Ser Glu Gly Asp Leu Leu Ala Glu Ile Glu
                245                 250                 255

Thr Asp Lys Ala Thr Ile Gly Phe Glu Val Gln Glu Glu Gly Tyr Leu
            260                 265                 270

Ala Lys Ile Leu Val Pro Glu Gly Thr Arg Asp Val Pro Leu Gly Thr
        275                 280                 285

Pro Leu Cys Ile Ile Val Glu Lys Glu Ala Asp Ile Ser Ala Phe Ala
    290                 295                 300

Asp Tyr Arg Pro Thr Glu Val Thr Asp Leu Lys Pro Gln Val Pro Pro
305                 310                 315                 320

Pro Thr Pro Pro Pro Val Ala Ala Val Pro Pro Thr Pro Gln Pro Leu
                325                 330                 335

Ala Pro Thr Pro Ser Ala Pro Cys Pro Ala Thr Pro Ala Gly Pro Lys
            340                 345                 350

Gly Arg Val Phe Val Ser Pro Leu Ala Lys Lys Leu Ala Val Glu Lys
        355                 360                 365

Gly Ile Asp Leu Thr Gln Val Lys Gly Thr Gly Pro Asp Gly Arg Ile
    370                 375                 380

Thr Lys Lys Asp Ile Asp Ser Phe Val Pro Ser Lys Val Ala Pro Ala
385                 390                 395                 400

Pro Ala Ala Val Val Pro Pro Thr Gly Pro Gly Met Ala Pro Val Pro
                405                 410                 415

Thr Gly Val Phe Thr Asp Ile Pro Ile Ser Asn Ile Arg Arg Val Ile
            420                 425                 430

Ala Gln Arg Leu Met Gln Ser Lys Gln Thr Ile Pro His Tyr Tyr Leu
        435                 440                 445

Ser Ile Asp Val Asn Met Gly Glu Val Leu Leu Val Arg Lys Glu Leu
    450                 455                 460

Asn Lys Ile Leu Glu Gly Arg Ser Lys Ile Ser Val Asn Asp Phe Ile
465                 470                 475                 480

Ile Lys Ala Ser Ala Leu Ala Cys Leu Lys Val Pro Glu Ala Asn Ser
                485                 490                 495

Ser Trp Met Asp Thr Val Ile Arg Gln Asn His Val Val Asp Val Ser
            500                 505                 510

Val Ala Val Ser Thr Pro Ala Gly Leu Ile Thr Pro Ile Val Phe Asn
        515                 520                 525

Ala His Ile Lys Gly Val Glu Thr Ile Ala Asn Asp Val Val Ser Leu
    530                 535                 540

Ala Thr Lys Ala Arg Glu Gly Lys Leu Gln Pro His Glu Phe Gln Gly
545                 550                 555                 560

Gly Thr Phe Thr Ile Ser Asn Leu Gly Met Phe Gly Ile Lys Asn Phe
                565                 570                 575

Ser Ala Ile Ile Asn Pro Pro Gln Ala Cys Ile Leu Ala Ile Gly Ala
            580                 585                 590

Ser Glu Asp Lys Leu Val Pro Ala Asp Asn Glu Lys Gly Phe Asp Val
        595                 600                 605

Ala Ser Met Met Ser Val Thr Leu Ser Cys Asp His Arg Val Val Asp
    610                 615                 620

Gly Ala Val Gly Ala Gln Trp Leu Ala Glu Phe Arg Lys Tyr Leu Glu
625                 630                 635                 640

Lys Pro Ile Thr Met Leu Leu
                645
```

```
<210> SEQ ID NO 13
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is N(epsilon)-Lipoylated Lys

<400> SEQUENCE: 13

Ala Glu Ile Glu Thr Asp Xaa Ala Thr Ile Gly Phe Glu Val Gln Glu
1               5                   10                  15

Glu Gly Lys

<210> SEQ ID NO 14
<211> LENGTH: 25
<212> TYPE: PRT
<213> ORGANISM: Homo sapiens

<400> SEQUENCE: 14

Gly Thr Phe Thr Ile Ser Asn Leu Gly Met Phe Gly Ile Lys Asn Phe
1               5                   10                  15

Ser Ala Ile Ile Asn Pro Pro Gln Ala
            20                  25

<210> SEQ ID NO 15
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Lys(ivDde)

<400> SEQUENCE: 15

Asn Xaa Ala Trp Lys Phe Glu His Ala Asn Phe Asn Asp Cys
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is triphenylmethylated Asp
<220> FEATURE:
<221> NAME/KEY: MOD_RES
<222> LOCATION: (2)..(2)
<223> OTHER INFORMATION: Xaa is i-butyl carbamated Lys
<220> FEATURE:
<221> NAME/KEY: MOD_RES
<222> LOCATION: (7)..(7)
<223> OTHER INFORMATION: Xaa is tert-Butylated glutamic acid
<220> FEATURE:
<221> NAME/KEY: MOD_RES
<222> LOCATION: (8)..(8)
<223> OTHER INFORMATION: Xaa is triphenylmethylated His
<220> FEATURE:
<221> NAME/KEY: MOD_RES
<222> LOCATION: (10)..(10)
<223> OTHER INFORMATION: Xaa is triphenylmethylated Asp
<220> FEATURE:
<221> NAME/KEY: MOD_RES
<222> LOCATION: (12)..(12)
```

```
<223> OTHER INFORMATION: Xaa is triphenylmethylated Asp
<220> FEATURE:
<221> NAME/KEY: MOD_RES
<222> LOCATION: (13)..(13)
<223> OTHER INFORMATION: Xaa is tert-Butylated aspartic acid
<220> FEATURE:
<221> NAME/KEY: MOD_RES
<222> LOCATION: (14)..(14)
<223> OTHER INFORMATION: Xaa is triphenylmethylated Cys

<400> SEQUENCE: 16

Xaa Xaa Ala Trp Lys Phe Xaa Xaa Ala Xaa Phe Xaa Xaa Xaa
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is triphenylmethylated Asp
<220> FEATURE:
<221> NAME/KEY: MOD_RES
<222> LOCATION: (2)..(2)
<223> OTHER INFORMATION: Xaa is i-butyl carbamated Lys
<220> FEATURE:
<221> NAME/KEY: MOD_RES
<222> LOCATION: (5)..(5)
<223> OTHER INFORMATION: Xaa is Lys(ivDde)
<220> FEATURE:
<221> NAME/KEY: MOD_RES
<222> LOCATION: (7)..(7)
<223> OTHER INFORMATION: Xaa is tert-Butylated glutamic acid
<220> FEATURE:
<221> NAME/KEY: MOD_RES
<222> LOCATION: (8)..(8)
<223> OTHER INFORMATION: Xaa is triphenylmethylated His
<220> FEATURE:
<221> NAME/KEY: MOD_RES
<222> LOCATION: (10)..(10)
<223> OTHER INFORMATION: Xaa is triphenylmethylated Asp
<220> FEATURE:
<221> NAME/KEY: MOD_RES
<222> LOCATION: (12)..(12)
<223> OTHER INFORMATION: Xaa is triphenylmethylated Asp
<220> FEATURE:
<221> NAME/KEY: MOD_RES
<222> LOCATION: (13)..(13)
<223> OTHER INFORMATION: Xaa is tert-Butylated aspartic acid
<220> FEATURE:
<221> NAME/KEY: MOD_RES
<222> LOCATION: (14)..(14)
<223> OTHER INFORMATION: Xaa is triphenylmethylated Cys

<400> SEQUENCE: 17

Xaa Xaa Ala Trp Xaa Phe Xaa Xaa Ala Xaa Phe Xaa Xaa Xaa
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Deoxyfructospyranosylated Lys

<400> SEQUENCE: 18

Asn Lys Ala Trp Xaa Phe Glu His Ala Asn Phe Asn Asp Cys
```

<210> SEQ ID NO 19
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is tert-Butylated glutamic acid
<220> FEATURE:
<221> NAME/KEY: MOD_RES
<222> LOCATION: (3)..(3)
<223> OTHER INFORMATION: Xaa is triphenylmethylated His
<220> FEATURE:
<221> NAME/KEY: MOD_RES
<222> LOCATION: (5)..(5)
<223> OTHER INFORMATION: Xaa is triphenylmethylated Asp
<220> FEATURE:
<221> NAME/KEY: MOD_RES
<222> LOCATION: (7)..(7)
<223> OTHER INFORMATION: Xaa is triphenylmethylated Asp
<220> FEATURE:
<221> NAME/KEY: MOD_RES
<222> LOCATION: (8)..(8)
<223> OTHER INFORMATION: Xaa is tert-Butylated aspartic acid
<220> FEATURE:
<221> NAME/KEY: MOD_RES
<222> LOCATION: (9)..(9)
<223> OTHER INFORMATION: Xaa is triphenylmethylated Cys

<400> SEQUENCE: 19

Phe Xaa Xaa Ala Xaa Phe Xaa Xaa Xaa
1               5

<210> SEQ ID NO 20
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is glycated Lys
<220> FEATURE:
<221> NAME/KEY: MOD_RES
<222> LOCATION: (3)..(3)
<223> OTHER INFORMATION: Xaa is tert-Butylated glutamic acid
<220> FEATURE:
<221> NAME/KEY: MOD_RES
<222> LOCATION: (4)..(4)
<223> OTHER INFORMATION: Xaa is triphenylmethylated His
<220> FEATURE:
<221> NAME/KEY: MOD_RES
<222> LOCATION: (6)..(6)
<223> OTHER INFORMATION: Xaa is triphenylmethylated Asp
<220> FEATURE:
<221> NAME/KEY: MOD_RES
<222> LOCATION: (8)..(8)
<223> OTHER INFORMATION: Xaa is triphenylmethylated Asp
<220> FEATURE:
<221> NAME/KEY: MOD_RES
<222> LOCATION: (9)..(9)
<223> OTHER INFORMATION: Xaa is tert-Butylated aspartic acid
<220> FEATURE:
<221> NAME/KEY: MOD_RES
<222> LOCATION: (10)..(10)
<223> OTHER INFORMATION: Xaa is triphenylmethylated Cys

<400> SEQUENCE: 20

Xaa Phe Xaa Xaa Ala Xaa Phe Xaa Xaa Xaa
1               5                   10

```
<210> SEQ ID NO 21
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Lys[N(epsilon)-(1-deoxy-D-
      glucitol-1-yl)]

<400> SEQUENCE: 21

Asn Lys Ala Trp Xaa Phe Glu His Ala Asn Phe Asn Asp Cys
1               5                   10

<210> SEQ ID NO 22
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Lys(N(epsilon)-ivDde)
<220> FEATURE:
<221> NAME/KEY: MOD_RES
<222> LOCATION: (3)..(3)
<223> OTHER INFORMATION: Xaa is Lys[N(epsilon)-(1-deoxy-D-
      glucitol-1-yl)]

<400> SEQUENCE: 22

Ala Xaa Xaa Cys
1

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Lys(N(epsilon)-Boc)
<220> FEATURE:
<221> NAME/KEY: MOD_RES
<222> LOCATION: (4)..(4)
<223> OTHER INFORMATION: Xaa is Trp(N(in)-Boc)
<220> FEATURE:
<221> NAME/KEY: MOD_RES
<222> LOCATION: (5)..(5)
<223> OTHER INFORMATION: Xaa is Lys(N(epsilon)-ivDde)
<220> FEATURE:
<221> NAME/KEY: MOD_RES
<222> LOCATION: (6)..(6)
<223> OTHER INFORMATION: Xaa is Glu(OtBu)
<220> FEATURE:
<221> NAME/KEY: MOD_RES
<222> LOCATION: (7)..(7)
<223> OTHER INFORMATION: Xaa is His(N(im)-Trt)
<220> FEATURE:
<221> NAME/KEY: MOD_RES
<222> LOCATION: (8)..(8)
<223> OTHER INFORMATION: Xaa is Asp(OtBu)
<220> FEATURE:
<221> NAME/KEY: MOD_RES
<222> LOCATION: (9)..(9)
<223> OTHER INFORMATION: Xaa is triphenylmethylated Cys

<400> SEQUENCE: 23
```

```
Asn Xaa Ala Xaa Xaa Xaa Xaa Xaa Xaa
1               5

<210> SEQ ID NO 24
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Lys(ivDde)
<220> FEATURE:
<221> NAME/KEY: MOD_RES
<222> LOCATION: (5)..(5)
<223> OTHER INFORMATION: Xaa is glycated Lys

<400> SEQUENCE: 24

Asn Xaa Ala Trp Xaa Phe Glu His Ala Asn Phe Asn Asp Cys
1               5                   10
```